United States Patent
Hallén et al.

(10) Patent No.: US 12,304,949 B2
(45) Date of Patent: May 20, 2025

(54) ANTI-S100A4 HUMANIZED ANTIBODIES, USES AND METHODS

(71) Applicant: Arxx Therapeutics AS, Oslo (NO)

(72) Inventors: Jonas Hallén, Oslo (NO); Rizwan Iqbal Hussain, Oslo (NO); Jörg Klingelhöfer, Oslo (NO); Tim Buss, Carlsbad, CA (US); Darragh MacCann, Belfast (GB)

(73) Assignee: Arxx Therapeutics AS (NO)

( * ) Notice: Subject to any disclaimer, the term of this patent is extended or adjusted under 35 U.S.C. 154(b) by 0 days.

(21) Appl. No.: 18/962,263

(22) Filed: Nov. 27, 2024

(65) Prior Publication Data

US 2025/0092125 A1    Mar. 20, 2025

Related U.S. Application Data

(63) Continuation of application No. 18/264,483, filed as application No. PCT/EP2022/053095 on Feb. 9, 2022.

(60) Provisional application No. 63/147,483, filed on Feb. 9, 2021.

(51) Int. Cl.
    C07K 16/24      (2006.01)
    A61P 35/00      (2006.01)
    C12N 15/63      (2006.01)

(52) U.S. Cl.
    CPC .............. *C07K 16/24* (2013.01); *A61P 35/00* (2018.01); *C12N 15/63* (2013.01); *C07K 2317/14* (2013.01); *C07K 2317/24* (2013.01); *C07K 2317/31* (2013.01); *C07K 2317/52* (2013.01); *C07K 2317/565* (2013.01)

(58) Field of Classification Search
    None
    See application file for complete search history.

(56) References Cited

U.S. PATENT DOCUMENTS 9,683,032 B2 * 6/2017 Klingelhöfer .......... C07K 16/18
2017/0355780 A1   12/2017 Chen et al.

FOREIGN PATENT DOCUMENTS

| WO | WO-2011157724 A1 | 12/2011 |
| WO | WO-2014068300 A1 | 5/2014 |
| WO | WO-2019007075 A1 | 1/2019 |

OTHER PUBLICATIONS

Apgar, James R. et al., "Beyond CDR-grafting: Structure-guided humanization of framework and CDR regions of an anti-myostatin antibody", MABS 2016, vol. 8, No. 7, 1302-1318.

Bournazos, Stylianos et al., "Fcy Receptor Function and the Design of Vaccination Strategies", Immunity 47, 2017, 224-233.

Bournazos, Stylianos et al., "Fcy receptor pathways during active and passive immunization", Immunology Reviews 2015, v . 268: 88-103.

Grum-Schwensen, Birgitte et al., "S100A4-neutralizing antibody suppresses spontaneous tumor progression, pre-metastatic niche formation and alters T-cell polarization balance", BMC Cancer (2015) 15:44.

Hernandez, Jose Luis et al., "Therapeutic Targeting of Tumor Growth and Angiogenesis with a Novel Anti-S1 00A4 Monoclonal Antibody", Plos One, 2013, 8(9): e72480, 17 pages.

Klingelhofer, Jorg et al., "Anti-S100A4 Antibody Suppresses Metastasis Formation by Blocking Strama Cell Invasion", Neoplasia (2012), 14, 1260-1268.

Kugler, Markus et al., "Stabilization and humanization of a single-chain Fv antibody fragment specific for human lymphocyte antigen CD19 by designed point mutations and CDR-grafting onto a human framework", Protein Engineering, Design & Selection, vol. 22, No. 3, 135-147, 2009.

Lo, Benny K.C. editor, "Antibody Humanization by CDR Grafting", Methods in Molecular Biology, Antibody Engineering Methods and Protocols, vol. 248, 2004, Humana Press, 135-176, 191-200.

O'Brien, Siobhan et al., "Humanization of Monoclonal Antibodies by CDR Grafting, Methods in Molecular Biology," in Recombinant Antibodies for Cancer Therapy: Methods and Protocols, 2002, pp. 81-100.

Tomcik, M. et al., "Anti-S1 00A4 Monoclonal Antibody Treatment Ameliorates Skin Fibrosis in Inflammatory and Non-Inflammatory Pre-Clinical Models of Systemic Sclerosis", Annals of the Rheumatic Diseases, 2021, 80:150.

Yu, Jifeng et al., "How to select IgG subclasses in developing anti-tumor therapeutic antibodies", Journal of Hematology & Oncology (2020) 13:45, 10 pages.

Zhang, Jinhua et al., "S100A4 blockage alleviates agonistic anti-CD137 antibody-induced liver pathology without disruption of antitumor immunity", Oncolmmunology (2018), 7:4, e1296996, 16 pages.

Ambartsumian, et al. "The Multifaceted S100A4 Protein in Cancer and Inflammation" Method Mol Biol. 2019;1929:339-365.

Akiyama, et al. "Clinical significance of serum S100 calcium-binding protein A4 in idiopathic pulmonary fibrosis," Respirology. 2019;25(7):743-749.

Arman and Krauel, "Human platelet IgG Fc receptor FcγRIIA in immunity and thrombosis," J Thromb Haemost. 2015;13:893-908.

Boye, et al., "Nuclear S100A4 is a novel prognostic marker in colorectal cancer" European Journal of Cancer. 2010:46 (16), 2919-2925.

Cabezon, et a., "Expression of S100A4 by a variety of cell types present in the tumour microenvironment of human breast cancer," Int. J. Cancer. 2007:121(1), 1433-1444.

(Continued)

*Primary Examiner* — Sharon X Wen

(74) *Attorney, Agent, or Firm* — Dechert LLP; Andrew T. Wilkins; David M. Lee

(57) ABSTRACT

Herein are provided isolated, humanized, anti-S100A4 antibody molecules and methods of producing said antibodies. Also provided are nucleic acids, vectors, isolated host cells and pharmaceutical compositions containing the antibody, and methods of treatment comprising administering said antibody.

25 Claims, 23 Drawing Sheets

Specification includes a Sequence Listing.

(56) References Cited

OTHER PUBLICATIONS

Cerezo, et al., "The metastasis promoting protein S100A4 is increased in idiopathic inflammatory myopathies," Rheumatology (Oxford). 2011;50(10):1766-72.

Chow, et al., "S100A4 Is a Biomarker and Regulator of Glioma Stem Cells That Is Critical for Mesenchymal Transition in Glioblastoma." Cancer Res. 2017;77(19):5360-5373.

Donato, "Intracellular and extracellular roles of S100 proteins," Microscopy Research and Technique. 2003;60 (6):540-551.

Fei, et al., "Role of metastasis-induced protein S100A4 in human non-tumor pathophysiologies," Cell Biosci. 2017;7:64.

Grum-Schwensen et al., "Suppression of tumour development and metastasis formation in mice lacking the S100A4 (mtsl) gene," Cancer Research. 2005;65(9):3772-3780.

Grum-Schwensen et al., "Lung metastasis fails in MMTV-PyMT oncomice lacking S100A4 due to a T-cell deficiency in primary tumours," Cancer research. 2010;70(3):936-947.

Helfman et al., "The metastasis associated protein S100A4: role in tumour progression and metastasis," British journal of cancer, 2005;92(11):1955-1958.

Kalluri and Zeisberg, "Fibroblasts in cancer," Nat Rev Cancer. 2006;6(5):392-401.

Klingelhöfer et al. "Up-regulation of metastasis-promoting S100A4 (Mts-1) in rheumatoid arthritis: putative involvement in the pathogenesis of rheumatoid arthritis," Arthritis Rheum. 2007;56(3):779-89.

Lo et al., "The epithelial-mesenchymal transition mediator S100A4 maintains cancer-initiating cells in head and neck cancers," Cancer Research. 2011;71(5):1912-1923.

Maelandsmo et al., "Different expression and clinical role of S100A4 in serous ovarian carcinoma at different anatomic sites," Tumour biology. 2009;30(1):15-25.

Mishra et al., "S100A4 calcium-binding protein is key player in tumour progression and metastasis: preclinical and clinical evidence," Cancer Metastasis Reviews. 2011;13:163-172.

Neidhart et al., "Oligomeric S100A4 Is Associated With Monocyte Innate Immune Memory and Bypass of Tolerance to Subsequent Stimulation With Lipopolysaccharides," Front Immunol. 2019;10:791.

Schmidt-Hansen et al., "Functional significance of metastasis-inducing S100A4 (Mts1) in tumour-stroma interplay," The Journal of Biological Chemistry. 2004;275(23):24498-24504.

Sherbet, "Metastasis promoter S100A4 is a potentially valuable molecular target for cancer therapy," Cancer letters. 2009;280(1):15-30.

Sun et al., "Bacillus anthracis peptidoglycan activates human platelets through FcγRII and complement," Blood. 2013;122(4)571-579.

Tomcik et al., "S100A4 amplifies TGF-β-induced fibroblast activation in systemic sclerosis," Ann Rheum Dis. 2015;74 (9):1748-55.

Van Erp et al., "Fc-Mediated Antibody Effector Functions During Respiratory Syncytial Virus Infection and Disease," Front Immunol. 2019;10:548.

Zibert et al., "Significance of the S100A4 protein in psoriasis," J Invest Dermatol. 2010;130(1):150-60.

\* cited by examiner

```
SEQUENCE LISTING

Sequence total quantity: 59
SEQ ID NO: 1           moltype = AA  length = 6
FEATURE                Location/Qualifiers
REGION                 1..6
                       note = CDR-H1
REGION                 1..6
                       note = MISC_FEATURE - Antibody region
source                 1..6
                       mol_type = protein
                       organism = synthetic construct
SEQUENCE: 1
NDYYWN                                                                    6

SEQ ID NO: 2           moltype = AA  length = 16
FEATURE                Location/Qualifiers
REGION                 1..16
                       note = CDR-H2
REGION                 1..16
                       note = MISC_FEATURE - Antibody region
source                 1..16
                       mol_type = protein
                       organism = synthetic construct
SEQUENCE: 2
HIGYGGNINY NPSLKN                                                         16

SEQ ID NO: 3           moltype = AA  length = 11
FEATURE                Location/Qualifiers
REGION                 1..11
                       note = CDR-H3
REGION                 1..11
                       note = MISC_FEATURE - Antibody region
source                 1..11
                       mol_type = protein
                       organism = synthetic construct
SEQUENCE: 3
ESFYDGYPFD Y                                                              11

SEQ ID NO: 4           moltype = AA  length = 9
FEATURE                Location/Qualifiers
REGION                 1..9
                       note = CDR-H1
REGION                 1..9
                       note = MISC_FEATURE - Antibody region
source                 1..9
                       mol_type = protein
                       organism = synthetic construct
SEQUENCE: 4
GDSFTNDYY                                                                 9

SEQ ID NO: 5           moltype = AA  length = 7
FEATURE                Location/Qualifiers
REGION                 1..7
                       note = CDR-H2
REGION                 1..7
                       note = MISC_FEATURE - Antibody region
source                 1..7
                       mol_type = protein
                       organism = synthetic construct
SEQUENCE: 5
IGYGGNI                                                                   7

SEQ ID NO: 6           moltype = AA  length = 13
FEATURE                Location/Qualifiers
REGION                 1..13
                       note = CDR-H3
```

```
REGION                 1..13
                       note = MISC_FEATURE - Antibody region
source                 1..13
                       mol_type = protein
                       organism = synthetic construct
SEQUENCE: 6
TRESFYDGYP FDY                                                        13

SEQ ID NO: 7           moltype = AA  length = 11
FEATURE                Location/Qualifiers
REGION                 1..11
                       note = CDR-L1
REGION                 1..11
                       note = MISC_FEATURE - Antibody region
source                 1..11
                       mol_type = protein
                       organism = synthetic construct
SEQUENCE: 7
RASQDIRNYL N                                                          11

SEQ ID NO: 8           moltype = AA  length = 7
FEATURE                Location/Qualifiers
REGION                 1..7
                       note = CDR-L2
REGION                 1..7
                       note = MISC_FEATURE - Antibody region
source                 1..7
                       mol_type = protein
                       organism = synthetic construct
SEQUENCE: 8
YTSRLHS                                                               7

SEQ ID NO: 9           moltype = AA  length = 9
FEATURE                Location/Qualifiers
REGION                 1..9
                       note = CDR-L3
REGION                 1..9
                       note = MISC_FEATURE - Antibody region
source                 1..9
                       mol_type = protein
                       organism = synthetic construct
SEQUENCE: 9
QQGNSLPRT                                                             9

SEQ ID NO: 10          moltype = AA  length = 6
FEATURE                Location/Qualifiers
REGION                 1..6
                       note = CDR-L1
REGION                 1..6
                       note = MISC_FEATURE - Antibody region
source                 1..6
                       mol_type = protein
                       organism = synthetic construct
SEQUENCE: 10
QDIRNY                                                                6

SEQ ID NO: 11          moltype =   length =
SEQUENCE: 11
000

SEQ ID NO: 12          moltype = AA  length = 9
FEATURE                Location/Qualifiers
REGION                 1..9
                       note = CDR-L3
REGION                 1..9
                       note = MISC_FEATURE - Antibody region
source                 1..9
                       mol_type = protein
                       organism = synthetic construct
SEQUENCE: 12
QQGNSLPRT                                                             9

SEQ ID NO: 13          moltype = AA  length = 120
FEATURE                Location/Qualifiers
REGION                 1..120
                       note = VH1
REGION                 1..120
                       note = MISC_FEATURE - Antibody region
source                 1..120
```

```
                              mol_type = protein
                              organism = synthetic construct
SEQUENCE: 13
QVQLQESGPG LVKPSQTLSL TCTVSGDSFT NDYYWNWIRQ HPGKGLEWIG HIGYGGNINY        60
NPSLKNRLSM SRDTSKNQFS LKLSSVTAAD TAVYYCTRES FYDGYPFDYW GQGTLVTVSS       120

SEQ ID NO: 14                 moltype = AA   length = 120
FEATURE                       Location/Qualifiers
REGION                        1..120
                              note = VH2
REGION                        1..120
                              note = MISC_FEATURE - Antibody region
source                        1..120
                              mol_type = protein
                              organism = synthetic construct
SEQUENCE: 14
QVQLQESGPG LVKPSETLSL TCSVSGDSFT NDYYWNWIRQ SPGKGLEWIG HIGYGGNINY        60
NPSLKNRVSI SIDTSRNQFS LKVTSMTAAD TAVYYCTRES FYDGYPFDYW GQGTLVTVSS       120

SEQ ID NO: 15                 moltype = AA   length = 120
FEATURE                       Location/Qualifiers
REGION                        1..120
                              note = VH3
REGION                        1..120
                              note = MISC_FEATURE - Antibody region
source                        1..120
                              mol_type = protein
                              organism = synthetic construct
SEQUENCE: 15
EVQLLESGPG LVKPSQTLSL TCTVSGDSFT NDYYWNWIRQ HPGKGLEWIG HIGYGGNINY        60
NPSLKNRVTI SVDTSKNQFS LKLSSVTAAD TAVYYCTRES FYDGYPFDYW GQGTLVTVSS       120

SEQ ID NO: 16                 moltype = AA   length = 120
FEATURE                       Location/Qualifiers
REGION                        1..120
                              note = VH4
REGION                        1..120
                              note = MISC_FEATURE - Antibody region
source                        1..120
                              mol_type = protein
                              organism = synthetic construct
SEQUENCE: 16
QVQLQESGPG LVKPSETLSL TCTVSGDSFT NDYYWNWIRQ PPGKGLEWIA HIGYGGNINY        60
NPSLKNRVTI SIDTSKNQFS LRLRSVTASD TAVYYCTRES FYDGYPFDYW GQGTLVTVSS       120

SEQ ID NO: 17                 moltype = AA   length = 120
FEATURE                       Location/Qualifiers
REGION                        1..120
                              note = VH5
REGION                        1..120
                              note = MISC_FEATURE - Antibody region
source                        1..120
                              mol_type = protein
                              organism = synthetic construct
SEQUENCE: 17
QVQLQESGPG LVKPSQTLSL TCAVYGDSFT NDYYWNWIRQ PPGKGLEWIG HIGYGGNINY        60
NPSLKNRVTI SVDTSKNQFS LKLSSVTAAD TAVYYCTRES FYDGYPFDYW GQGTLVTVSA       120

SEQ ID NO: 18                 moltype = AA   length = 107
FEATURE                       Location/Qualifiers
REGION                        1..107
                              note = VL1
REGION                        1..107
                              note = MISC_FEATURE - Antibody region
source                        1..107
                              mol_type = protein
                              organism = synthetic construct
SEQUENCE: 18
DIQMTQSPSS LSASVGDRVT VTCRASQDIR NYLNWYQQQP GKAPKLLIYY TSRLHSGVPS        60
RFSGSGSGTD FTLTISSLQP EDFATYFCQQ GNSLPRTFGQ GTKVEIK                    107

SEQ ID NO: 19                 moltype = AA   length = 107
FEATURE                       Location/Qualifiers
REGION                        1..107
                              note = VL2
REGION                        1..107
                              note = MISC_FEATURE - Antibody region
source                        1..107
                              mol_type = protein
```

```
                        organism = synthetic construct
SEQUENCE: 19
DIQMTQSPSS LSASVGDRVT ITCRASQDIR NYLNWYQQKP GKTPKLLIYY TSRLHSGVPS    60
RFSGSGSGTD FIFTISSLQP EDIATYYCQQ GNSLPRTFGG GTKVEIK                 107

SEQ ID NO: 20           moltype = AA  length = 107
FEATURE                 Location/Qualifiers
REGION                  1..107
                        note = VL3
REGION                  1..107
                        note = MISC_FEATURE - Antibody region
source                  1..107
                        mol_type = protein
                        organism = synthetic construct
SEQUENCE: 20
DIQMTQSPSS LSASVGDRVT ITCRASQDIR NYLNWYQQKP GKAPKLLLYY TSRLHSGVPS    60
RFSGSGSGTD YTLTISSLQP EDFATYYCQQ GNSLPRTFGG GTKVEIK                 107

SEQ ID NO: 21           moltype = AA  length = 107
FEATURE                 Location/Qualifiers
REGION                  1..107
                        note = VL4
REGION                  1..107
                        note = MISC_FEATURE - Antibody region
source                  1..107
                        mol_type = protein
                        organism = synthetic construct
SEQUENCE: 21
DIQLTQSPSS LSASVGDRVT ITCRASQDIR NYLNWYQQKP GKGPKLLIYY TSRLHSGVPS    60
RFSGSGSGTD FSLTISSLQP EDLATYYCQQ GNSLPRTFGG GTKVEIK                 107

SEQ ID NO: 22           moltype = AA  length = 107
FEATURE                 Location/Qualifiers
REGION                  1..107
                        note = VL5
REGION                  1..107
                        note = MISC_FEATURE - Antibody region
source                  1..107
                        mol_type = protein
                        organism = synthetic construct
SEQUENCE: 22
DIQMTQSPSS LSASVGDRVT ITCRASQDIR NYLNWYQQKP GKVPKLLIYY TSRLHSGVPS    60
RFSGSGSGTD FTLTISSLQP EDVATYYCQQ GNSLPRTFGG GTKLEIK                 107

SEQ ID NO: 23           moltype = AA  length = 101
FEATURE                 Location/Qualifiers
REGION                  1..101
                        note = MISC_FEATURE - Human S100A4 (protein) amino acids 1
                         to 101
source                  1..101
                        mol_type = protein
                        organism = Homo sapiens
SEQUENCE: 23
MACPLEKALD VMVSTFHKYS GKEGDKFKLN KSELKELLTR ELPSFLGKRT DEAAFQKLMS    60
NLDSNRDNEV DFQEYCVFLS CIAMMCNEFF EGFPDKQPRK K                      101

SEQ ID NO: 24           moltype = AA  length = 120
FEATURE                 Location/Qualifiers
REGION                  1..120
                        note = VH1_H40Phe
REGION                  1..120
                        note = MISC_FEATURE - Antibody region
source                  1..120
                        mol_type = protein
                        organism = synthetic construct
SEQUENCE: 24
QVQLQESGPG LVKPSQTLSL TCTVSGDSFT NDYYWNWIRQ FPGKGLEWIG HIGYGGNINY    60
NPSLKNRLSM SRDTSKNQFS LKLSSVTAAD TAVYYCTRES FYDGYPFDYW GQGTLVTVSS   120

SEQ ID NO: 25           moltype = AA  length = 120
FEATURE                 Location/Qualifiers
REGION                  1..120
                        note = VH1_H43Ser
REGION                  1..120
                        note = MISC_FEATURE - Antibody region
source                  1..120
                        mol_type = protein
                        organism = synthetic construct
SEQUENCE: 25
```

```
QVQLQESGPG LVKPSQTLSL TCTVSGDSFT NDYYWNWIRQ HPGSGLEWIG HIGYGGNINY   60
NPSLKNRLSM SRDTSKNQFS LKLSSVTAAD TAVYYCTRES FYDGYPFDYW GQGTLVTVSS  120

SEQ ID NO: 26              moltype = AA   length = 120
FEATURE                    Location/Qualifiers
REGION                     1..120
                           note = VH1_H44Lys
REGION                     1..120
                           note = MISC_FEATURE - Antibody region
source                     1..120
                           mol_type = protein
                           organism = synthetic construct
SEQUENCE: 26
QVQLQESGPG LVKPSQTLSL TCTVSGDSFT NDYYWNWIRQ HPGKKLEWIG HIGYGGNINY   60
NPSLKNRLSM SRDTSKNQFS LKLSSVTAAD TAVYYCTRES FYDGYPFDYW GQGTLVTVSS  120

SEQ ID NO: 27              moltype = AA   length = 120
FEATURE                    Location/Qualifiers
REGION                     1..120
                           note = VH2_H40Phe
REGION                     1..120
                           note = MISC_FEATURE - Antibody region
source                     1..120
                           mol_type = protein
                           organism = synthetic construct
SEQUENCE: 27
QVQLQESGPG LVKPSETLSL TCSVSGDSFT NDYYWNWIRQ FPGKGLEWIG HIGYGGNINY   60
NPSLKNRVSI SIDTSRNQFS LKVTSMTAAD TAVYYCTRES FYDGYPFDYW GQGTLVTVSS  120

SEQ ID NO: 28              moltype = AA   length = 120
FEATURE                    Location/Qualifiers
REGION                     1..120
                           note = VH2_H43Ser
REGION                     1..120
                           note = MISC_FEATURE - Antibody region
source                     1..120
                           mol_type = protein
                           organism = synthetic construct
SEQUENCE: 28
QVQLQESGPG LVKPSETLSL TCSVSGDSFT NDYYWNWIRQ SPGSGLEWIG HIGYGGNINY   60
NPSLKNRVSI SIDTSRNQFS LKVTSMTAAD TAVYYCTRES FYDGYPFDYW GQGTLVTVSS  120

SEQ ID NO: 29              moltype = AA   length = 120
FEATURE                    Location/Qualifiers
REGION                     1..120
                           note = VH2_H44Lys
REGION                     1..120
                           note = MISC_FEATURE - Antibody region
source                     1..120
                           mol_type = protein
                           organism = synthetic construct
SEQUENCE: 29
QVQLQESGPG LVKPSETLSL TCSVSGDSFT NDYYWNWIRQ SPGKKLEWIG HIGYGGNINY   60
NPSLKNRVSI SIDTSRNQFS LKVTSMTAAD TAVYYCTRES FYDGYPFDYW GQGTLVTVSS  120

SEQ ID NO: 30              moltype = AA   length = 120
FEATURE                    Location/Qualifiers
REGION                     1..120
                           note = VH3_H40Phe
REGION                     1..120
                           note = MISC_FEATURE - Antibody region
source                     1..120
                           mol_type = protein
                           organism = synthetic construct
SEQUENCE: 30
EVQLLESGPG LVKPSQTLSL TCTVSGDSFT NDYYWNWIRQ FPGKGLEWIG HIGYGGNINY   60
NPSLKNRVTI SVDTSKNQFS LKLSSVTAAD TAVYYCTRES FYDGYPFDYW GQGTLVTVSS  120

SEQ ID NO: 31              moltype = AA   length = 120
FEATURE                    Location/Qualifiers
REGION                     1..120
                           note = VH3_H43Ser
REGION                     1..120
                           note = MISC_FEATURE - Antibody region
source                     1..120
                           mol_type = protein
                           organism = synthetic construct
SEQUENCE: 31
EVQLLESGPG LVKPSQTLSL TCTVSGDSFT NDYYWNWIRQ HPGSGLEWIG HIGYGGNINY   60
```

```
NPSLKNRVTI SVDTSKNQFS LKLSSVTAAD TAVYYCTRES FYDGYPFDYW GQGTLVTVSS    120

SEQ ID NO: 32          moltype = AA   length = 120
FEATURE                Location/Qualifiers
REGION                 1..120
                       note = VH3_H44Lys
REGION                 1..120
                       note = MISC_FEATURE - Antibody region
source                 1..120
                       mol_type = protein
                       organism = synthetic construct
SEQUENCE: 32
EVQLLESGPG LVKPSQTLSL TCTVSGDSFT NDYYWNWIRQ HPGKKLEWIG HIGYGGNINY    60
NPSLKNRVTI SVDTSKNQFS LKLSSVTAAD TAVYYCTRES FYDGYPFDYW GQGTLVTVSS    120

SEQ ID NO: 33          moltype = AA   length = 120
FEATURE                Location/Qualifiers
REGION                 1..120
                       note = VH4_H40Phe
REGION                 1..120
                       note = MISC_FEATURE - Antibody region
source                 1..120
                       mol_type = protein
                       organism = synthetic construct
SEQUENCE: 33
QVQLQESGPG LVKPSETLSL TCTVSGDSFT NDYYWNWIRQ FPGKGLEWIA HIGYGGNINY    60
NPSLKNRVTI SIDTSKNQFS LRLRSVTASD TAVYYCTRES FYDGYPFDYW GQGTLVTVSS    120

SEQ ID NO: 34          moltype = AA   length = 120
FEATURE                Location/Qualifiers
REGION                 1..120
                       note = VH4_H43Ser
REGION                 1..120
                       note = MISC_FEATURE - Antibody region
source                 1..120
                       mol_type = protein
                       organism = synthetic construct
SEQUENCE: 34
QVQLQESGPG LVKPSETLSL TCTVSGDSFT NDYYWNWIRQ PPGSGLEWIA HIGYGGNINY    60
NPSLKNRVTI SIDTSKNQFS LRLRSVTASD TAVYYCTRES FYDGYPFDYW GQGTLVTVSS    120

SEQ ID NO: 35          moltype = AA   length = 120
FEATURE                Location/Qualifiers
REGION                 1..120
                       note = VH4_H44Lys
REGION                 1..120
                       note = MISC_FEATURE - Antibody region
source                 1..120
                       mol_type = protein
                       organism = synthetic construct
SEQUENCE: 35
QVQLQESGPG LVKPSETLSL TCTVSGDSFT NDYYWNWIRQ PPGKKLEWIA HIGYGGNINY    60
NPSLKNRVTI SIDTSKNQFS LRLRSVTASD TAVYYCTRES FYDGYPFDYW GQGTLVTVSS    120

SEQ ID NO: 36          moltype = AA   length = 120
FEATURE                Location/Qualifiers
REGION                 1..120
                       note = VH5_H40Phe
REGION                 1..120
                       note = MISC_FEATURE - Antibody region
source                 1..120
                       mol_type = protein
                       organism = synthetic construct
SEQUENCE: 36
QVQLQESGPG LVKPSQTLSL TCAVYGDSFT NDYYWNWIRQ FPGKGLEWIG HIGYGGNINY    60
NPSLKNRVTI SVDTSKNQFS LKLSSVTAAD TAVYYCTRES FYDGYPFDYW GQGTLVTVSA    120

SEQ ID NO: 37          moltype = AA   length = 120
FEATURE                Location/Qualifiers
REGION                 1..120
                       note = VH5_H43Ser
REGION                 1..120
                       note = MISC_FEATURE - Antibody region
source                 1..120
                       mol_type = protein
                       organism = synthetic construct
SEQUENCE: 37
QVQLQESGPG LVKPSQTLSL TCAVYGDSFT NDYYWNWIRQ PPGSGLEWIG HIGYGGNINY    60
NPSLKNRVTI SVDTSKNQFS LKLSSVTAAD TAVYYCTRES FYDGYPFDYW GQGTLVTVSA    120
```

```
SEQ ID NO: 38            moltype = AA   length = 120
FEATURE                  Location/Qualifiers
REGION                   1..120
                         note = VH5_H44Lys
REGION                   1..120
                         note = MISC_FEATURE - Antibody region
source                   1..120
                         mol_type = protein
                         organism = synthetic construct
SEQUENCE: 38
QVQLQESGPG LVKPSQTLSL TCAVYGDSFT NDYYWNWIRQ PPGKKLEWIG HIGYGGNINY    60
NPSLKNRVTI SVDTSKNQFS LKLSSVTAAD TAVYYCTRES FYDGYPFDYW GQGTLVTVSA   120

SEQ ID NO: 39            moltype = AA   length = 107
FEATURE                  Location/Qualifiers
REGION                   1..107
                         note = VL1_L42Gly
REGION                   1..107
                         note = MISC_FEATURE - Antibody region
source                   1..107
                         mol_type = protein
                         organism = synthetic construct
SEQUENCE: 39
DIQMTQSPSS LSASVGDRVT VTCRASQDIR NYLNWYQQQP GGAPKLLIYY TSRLHSGVPS    60
RFSGSGSGTD FTLTISSLQP EDFATYFCQQ GNSLPRTFGQ GTKVEIK                 107

SEQ ID NO: 40            moltype = AA   length = 107
FEATURE                  Location/Qualifiers
REGION                   1..107
                         note = VL1_L43Thr
REGION                   1..107
                         note = MISC_FEATURE - Antibody region
source                   1..107
                         mol_type = protein
                         organism = synthetic construct
SEQUENCE: 40
DIQMTQSPSS LSASVGDRVT VTCRASQDIR NYLNWYQQQP GKTPKLLIYY TSRLHSGVPS    60
RFSGSGSGTD FTLTISSLQP EDFATYFCQQ GNSLPRTFGQ GTKVEIK                 107

SEQ ID NO: 41            moltype = AA   length = 107
FEATURE                  Location/Qualifiers
REGION                   1..107
                         note = VL1_L44Leu
REGION                   1..107
                         note = MISC_FEATURE - Antibody region
source                   1..107
                         mol_type = protein
                         organism = synthetic construct
SEQUENCE: 41
DIQMTQSPSS LSASVGDRVT VTCRASQDIR NYLNWYQQQP GKALKLLIYY TSRLHSGVPS    60
RFSGSGSGTD FTLTISSLQP EDFATYFCQQ GNSLPRTFGQ GTKVEIK                 107

SEQ ID NO: 42            moltype = AA   length = 107
FEATURE                  Location/Qualifiers
REGION                   1..107
                         note = VL2_L42Gly
REGION                   1..107
                         note = MISC_FEATURE - Antibody region
source                   1..107
                         mol_type = protein
                         organism = synthetic construct
SEQUENCE: 42
DIQMTQSPSS LSASVGDRVT ITCRASQDIR NYLNWYQQKP GGTPKLLIYY TSRLHSGVPS    60
RFSGSGSGTD FIFTISSLQP EDIATYYCQQ GNSLPRTFGG GTKVEIK                 107

SEQ ID NO: 43            moltype = AA   length = 107
FEATURE                  Location/Qualifiers
REGION                   1..107
                         note = VL2_L43Thr
REGION                   1..107
                         note = MISC_FEATURE - Antibody region
source                   1..107
                         mol_type = protein
                         organism = synthetic construct
SEQUENCE: 43
DIQMTQSPSS LSASVGDRVT ITCRASQDIR NYLNWYQQKP GKTPKLLIYY TSRLHSGVPS    60
RFSGSGSGTD FIFTISSLQP EDIATYYCQQ GNSLPRTFGG GTKVEIK                 107
```

```
SEQ ID NO: 44            moltype = AA  length = 107
FEATURE                  Location/Qualifiers
REGION                   1..107
                         note = VL2_L44Leu
REGION                   1..107
                         note = MISC_FEATURE - Antibody region
source                   1..107
                         mol_type = protein
                         organism = synthetic construct
SEQUENCE: 44
DIQMTQSPSS LSASVGDRVT ITCRASQDIR NYLNWYQQKP GKTLKLLIYY TSRLHSGVPS   60
RFSGSGSGTD FIFTISSLQP EDIATYYCQQ GNSLPRTFGG GTKVEIK                107

SEQ ID NO: 45            moltype = AA  length = 107
FEATURE                  Location/Qualifiers
REGION                   1..107
                         note = VL3_L42Gly
REGION                   1..107
                         note = MISC_FEATURE - Antibody region
source                   1..107
                         mol_type = protein
                         organism = synthetic construct
SEQUENCE: 45
DIQMTQSPSS LSASVGDRVT ITCRASQDIR NYLNWYQQKP GGAPKLLLYY TSRLHSGVPS   60
RFSGSGSGTD YTLTISSLQP EDFATYYCQQ GNSLPRTFGG GTKVEIK                107

SEQ ID NO: 46            moltype = AA  length = 107
FEATURE                  Location/Qualifiers
REGION                   1..107
                         note = VL3_L43Thr
REGION                   1..107
                         note = MISC_FEATURE - Antibody region
source                   1..107
                         mol_type = protein
                         organism = synthetic construct
SEQUENCE: 46
DIQMTQSPSS LSASVGDRVT ITCRASQDIR NYLNWYQQKP GKTPKLLLYY TSRLHSGVPS   60
RFSGSGSGTD YTLTISSLQP EDFATYYCQQ GNSLPRTFGG GTKVEIK                107

SEQ ID NO: 47            moltype = AA  length = 107
FEATURE                  Location/Qualifiers
REGION                   1..107
                         note = VL3_L44Leu
REGION                   1..107
                         note = MISC_FEATURE - Antibody region
source                   1..107
                         mol_type = protein
                         organism = synthetic construct
SEQUENCE: 47
DIQMTQSPSS LSASVGDRVT ITCRASQDIR NYLNWYQQKP GKALKLLLYY TSRLHSGVPS   60
RFSGSGSGTD YTLTISSLQP EDFATYYCQQ GNSLPRTFGG GTKVEIK                107

SEQ ID NO: 48            moltype = AA  length = 107
FEATURE                  Location/Qualifiers
REGION                   1..107
                         note = VL4_L42Gly
REGION                   1..107
                         note = MISC_FEATURE - Antibody region
source                   1..107
                         mol_type = protein
                         organism = synthetic construct
SEQUENCE: 48
DIQLTQSPSS LSASVGDRVT ITCRASQDIR NYLNWYQQKP GGGPKLLIYY TSRLHSGVPS   60
RFSGSGSGTD FSLTISSLQP EDLATYYCQQ GNSLPRTFGG GTKVEIK                107

SEQ ID NO: 49            moltype = AA  length = 107
FEATURE                  Location/Qualifiers
REGION                   1..107
                         note = VL4_L43Thr
REGION                   1..107
                         note = MISC_FEATURE - Antibody region
source                   1..107
                         mol_type = protein
                         organism = synthetic construct
SEQUENCE: 49
DIQLTQSPSS LSASVGDRVT ITCRASQDIR NYLNWYQQKP GKTPKLLIYY TSRLHSGVPS   60
RFSGSGSGTD FSLTISSLQP EDLATYYCQQ GNSLPRTFGG GTKVEIK                107

SEQ ID NO: 50            moltype = AA  length = 107
```

```
FEATURE                 Location/Qualifiers
REGION                  1..107
                        note = VL4_L44Leu
REGION                  1..107
                        note = MISC_FEATURE - Antibody region
source                  1..107
                        mol_type = protein
                        organism = synthetic construct
SEQUENCE: 50
DIQLTQSPSS LSASVGDRVT ITCRASQDIR NYLNWYQQKP GKGLKLLIYY TSRLHSGVPS     60
RFSGSGSGTD FSLTISSLQP EDLATYYCQQ GNSLPRTFGG GTKVEIK                  107

SEQ ID NO: 51           moltype = AA  length = 107
FEATURE                 Location/Qualifiers
REGION                  1..107
                        note = VL5_L42Gly
REGION                  1..107
                        note = MISC_FEATURE - Antibody region
source                  1..107
                        mol_type = protein
                        organism = synthetic construct
SEQUENCE: 51
DIQMTQSPSS LSASVGDRVT ITCRASQDIR NYLNWYQQKP GGVPKLLIYY TSRLHSGVPS     60
RFSGSGSGTD FTLTISSLQP EDVATYYCQQ GNSLPRTFGG GTKLEIK                  107

SEQ ID NO: 52           moltype = AA  length = 107
FEATURE                 Location/Qualifiers
REGION                  1..107
                        note = VL5_L43Thr
REGION                  1..107
                        note = MISC_FEATURE - Antibody region
source                  1..107
                        mol_type = protein
                        organism = synthetic construct
SEQUENCE: 52
DIQMTQSPSS LSASVGDRVT ITCRASQDIR NYLNWYQQKP GKTPKLLIYY TSRLHSGVPS     60
RFSGSGSGTD FTLTISSLQP EDVATYYCQQ GNSLPRTFGG GTKLEIK                  107

SEQ ID NO: 53           moltype = AA  length = 107
FEATURE                 Location/Qualifiers
REGION                  1..107
                        note = VL5_L44Leu
REGION                  1..107
                        note = MISC_FEATURE - Antibody region
source                  1..107
                        mol_type = protein
                        organism = synthetic construct
SEQUENCE: 53
DIQMTQSPSS LSASVGDRVT ITCRASQDIR NYLNWYQQKP GKVLKLLIYY TSRLHSGVPS     60
RFSGSGSGTD FTLTISSLQP EDVATYYCQQ GNSLPRTFGG GTKLEIK                  107

SEQ ID NO: 54           moltype = AA  length = 138
FEATURE                 Location/Qualifiers
REGION                  1..138
                        note = VH region 6B12 monoclonal antibody (amino acid
                         sequence) Leader sequence-FR1-CDR1-FR2-CDR2-FR3-CDR3-FR4
REGION                  1..18
                        note = MISC_FEATURE - leader sequence
REGION                  49..54
                        note = MISC_FEATURE - CDR1
REGION                  69..84
                        note = MISC_FEATURE - CDR2
REGION                  117..127
                        note = MISC_FEATURE - CDR3
source                  1..138
                        mol_type = protein
                        organism = synthetic construct
SEQUENCE: 54
MKVLSLLYLL TAIPGILSDV QLQESGPGLV KPSQSLSLTC SVTGDSFTND YYWNWIRQFP     60
GSKLEWMGHI GYGGNINYNP SLKNRISITR DTSKNQFFLR LTSVTTEDTA TYYCTRESFY   120
DGYPFDYWGQ GTLVTVSA                                                  138

SEQ ID NO: 55           moltype = AA  length = 127
FEATURE                 Location/Qualifiers
REGION                  1..127
                        note = VL region 6B12 monoclonal antibody (amino acid
                         sequence) Leader sequence-FR1-CDR1-FR2-CDR2-FR3-CDR3-FR4
REGION                  1..20
                        note = MISC_FEATURE - Leader sequence
```

```
REGION                  44..54
                        note = MISC_FEATURE - CDR1
REGION                  70..76
                        note = MISC_FEATURE - CDR2
REGION                  109..117
                        note = MISC_FEATURE - CDR3
source                  1..127
                        mol_type = protein
                        organism = synthetic construct
SEQUENCE: 55
MMSSAQFLGL LLLCFQGTRC DIQMTQTTSS LSASLGDRVT ISCRASQDIR NYLNWYQQRP    60
GGTLKLLIYY TSRLHSGVPS RFSGSGSGTD YSLTISNLEQ EDIATYFCQQ GNSLPRTFGG   120
GTKLEIK                                                             127

SEQ ID NO: 56           moltype = AA  length = 326
FEATURE                 Location/Qualifiers
REGION                  1..326
                        note = MISC_FEATURE - IgG4 CH
source                  1..326
                        mol_type = protein
                        organism = Homo sapiens
SEQUENCE: 56
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLG                                        326

SEQ ID NO: 57           moltype = AA  length = 107
FEATURE                 Location/Qualifiers
REGION                  1..107
                        note = MISC_FEATURE - k light chain constant region (CL)
source                  1..107
                        mol_type = protein
                        organism = Homo sapiens
SEQUENCE: 57
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 58           moltype = AA  length = 446
FEATURE                 Location/Qualifiers
REGION                  1..446
                        note = AX-202 complete heavy chain
REGION                  1..446
                        note = MISC_FEATURE - Antibody region
source                  1..446
                        mol_type = protein
                        organism = synthetic construct
SEQUENCE: 58
QVQLQESGPG LVKPSQTLSL TCTVSGDSFT NDYYWNWIRQ HPGKGLEWIG HIGYGGNINY    60
NPSLKNRLSM SRDTSKNQFS LKLSSVTAAD TAVYYCTRES FYDGYPFDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLG                                        446

SEQ ID NO: 59           moltype = AA  length = 214
FEATURE                 Location/Qualifiers
REGION                  1..214
                        note = AX-202 complete light chain
REGION                  1..214
                        note = MISC_FEATURE - Antibody region
source                  1..214
                        mol_type = protein
                        organism = synthetic construct
SEQUENCE: 59
DIQMTQSPSS LSASVGDRVT ITCRASQDIR NYLNWYQQKP GKALKLLLYY TSRLHSGVPS    60
RFSGSGSGTD YTLTISSLQP EDFATYYCQQ GNSLPRTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

ANTI-S100A4 HUMANIZED ANTIBODIES, USES AND METHODS

CROSS-REFERENCE TO RELATED APPLICATIONS

This application is a continuation of U.S. patent application Ser. No. 18/264,483, filed Aug. 7, 2023, which is a national phase entry pursuant to 35 U.S.C. § 371 of International Application Serial No. PCT/EP2022/053095, filed Feb. 9, 2022, which claims the benefit of priority to U.S. Provisional Patent Application Ser. No. 63/147,483, filed Feb. 9, 2021, the entire disclosures of which are hereby incorporated herein by reference.

SEQUENCE LISTING

This application contains a sequence listing which has been submitted electronically in ST.26 format and is hereby incorporated by reference in its entirety. Said ST.26 copy, created on Nov. 26, 2024, is named "212914_seglist.xml" and is 102,318 bytes in size.

FIELD OF THE INVENTION

The present invention relates to isolated anti-S100A4 humanized antibody molecules and their medical uses, and more particularly to isolated anti-S100A4 humanized antibody molecules that are capable of inhibiting the biological activity of S100A4, for example in promoting chronic inflammation, fibrosis, tumour progression and/or in inducing tumour metastasis, and their uses in the treatment of fibrotic disease, inflammatory conditions, and cancer, in particular metastatic cancer.

BACKGROUND OF THE INVENTION

Fibrosis is defined as an excessive deposition of extracellular matrix proteins. The early stages of fibrotic disease are almost always characterised by an inflammatory response that functions to attract, differentiate and activate fibroblasts which in turn produce collagen and other extracellular matrix proteins. If these processes become chronic, the inflammatory and/or fibrotic responses gradually undermine physiological tissue function and may lead to organ compromise or failure. The mechanisms involved in chronic inflammation and fibrosis are underlying drivers of a wide range of diseases with different clinical manifestations, which include, in addition to pure fibrotic and inflammatory conditions, atherosclerosis, cancer and neurodegenerative disease. In cancer, a diseased tissue microenvironment provides an essential support mechanism for malignant cells to proliferate and spread. The activation of inflammatory and fibrotic pathways play an important role in the development of pre-metastatic niches that provide the necessary conditions for primary tumour cells to spread to distant organs.

S100A4 has been identified as a key protein involved in the processes that amplify and sustain inappropriate activation of inflammatory and fibrotic pathways. S100A4 belongs to the S100 family of small Ca-binding proteins with diverse extra- and intra-cellular function (Donato, 2003). Under physiological conditions, S100A4 is predominantly located intracellularly, but is released to the extracellular environment upon cell stress or injury (Fei et al., 2017). Extracellular S100A4 forms higher order oligomers that engage Pattern Recognition Receptors (PRRs) which in turn activate multiple inflammatory and fibrotic responses (Ambartsumian et al., 2019; Fei et al., 2017). Through interaction with PRRs, S100A4 triggers release of inflammatory mediators from immune cells, stimulates the release of extracellular matrix proteins from fibroblasts, and is involved in epithelial-to-mesenchymal transition (Kalluri & Zeisberg, 2006; Tomcik et al., 2015; Neidhart et al., 2019). Overexpression of S100A4 is a hallmark of chronic inflammation and fibrosis. Numerous studies have found elevated levels of S100A4 compared to healthy controls in different human diseases including systemic sclerosis, interstitial pulmonary fibrosis, rheumatoid arthritis, psoriasis, and dermatomyositis (Tomcik et al., 2015; Zibert et al., 2008; Klingelhafer et al., 2007; Cerezo et al., 2011; Akiyama et al., 2020).

Several studies employing cell-based assays or in vivo disease models have suggested that S100A4 is causally involved in the pathogenesis of inflammation and fibrosis (Ambartsumian et al., 2019). Knockdown of S100A4 in fibroblasts prevents the TGF P induced activation of fibroblasts (Tomcik et al., 2015). Knockout of S100A4 inhibits fibrosis, inflammation and cancer spread in several animal models including bleomycin-induced skin or pulmonary fibrosis, tight-skin 1 skin fibrosis and several cancer models (Ambartsumian et al., 2019; Tomcik et al., 2015).

Numerous studies connect the S100A4 activity with tumour progression and metastasis formation. This evidence has been accumulated using in vitro studies of cancer cell lines, transgenic and knockout mouse models and assessment of its prognostic significance for metastasis in patients with cancer (Boye et al., 2010; Helfman et al., 2005; Mishra et al., 2011).

S100A4 activity is associated with stimulation of cancer cell motility and invasion, normal and aberrant proliferation, apoptosis and differentiation. It is involved in signalling pathways leading to the remodelling of the cell membrane and the extracellular matrix; modulation of cytoskeletal dynamics, acquisition of invasiveness and induction of angiogenesis (Sherbet, 2009).

It has been shown that S100A4 is expressed in certain tumour cells, but more generally it is activated and secreted from certain cancer-associated stroma cells which lead to its accumulation in the tumour microenvironment. Moreover, it has been shown that the metastatic microenvironment contains greater numbers of S100A4-positive stromal cells than the primary tumour microenvironment (Cabezon et al., 2007; Grum-Schwensen et al., 2005; 2010; Maelandsmo et al., 2009; Schmidt-Hansen, et al., 2004a).

Furthermore, S100A4 has been shown to maintain the stemness properties and tumorigenicity of cancer-initiating cells in head and neck cancers and glioblastoma (Lo et al., 2011; Chow et al., 2017). Development of drugs capable of inhibiting the bioactivity of S100A4 may therefore represent a promising therapeutic option to modulate multiple inflammatory and fibrotic pathways that are activated in a range of human diseases. There is thus an unmet need for therapeutic anti-S100A4 antibodies, particularly humanized anti-S100A4 antibodies, as they would specifically target the extracellular, disease-causing fraction of S100A4.

Humanized antibodies are antibodies from non-human species whose protein sequences have been modified to increase their similarity to antibody variants produced naturally in humans. The process of "humanization" is usually applied to monoclonal antibodies developed for administration to humans (for example, antibodies developed as anti-cancer drugs). Humanization can be necessary when the process of developing a specific antibody involves generation in a non-human immune system (such as that in mice). The protein sequences of antibodies produced in non-human immune systems are partially distinct from homologous antibodies occurring naturally in humans, and are therefore potentially immunogenic when administered to human patients, which can remove any therapeutic benefit and potentially cause adverse effects in the patient.

SUMMARY OF THE INVENTION

The present invention provides a humanized anti-s100A4 antibody with an improved safety profile.

The inventors have found that murine IgG1 and humanized IgG1 anti-S100A4 antibodies elicit a counterintuitive increase in the pro-inflammatory cytokine TNFα, while at the same time blocking the S100A4 stimulated increase of IL-6 and IL-10. The increase in TNFα is elicited through FcγRIIA receptor clustering and activation. This effect is surprisingly dependent on both the anti-S100A4 antibody and the S100A4 protein, as neither anti-S100A4 antibody in the absence of S100A4, nor S100A4 in combination with an isotype control antibody (either human IgG1 or human IgG4) resulted in FcγRIIA receptor clustering.

The inventors have found that a subclass switch of the humanized anti-S100A4 antibody from an IgG1 scaffold to an IgG4 scaffold attenuates this previously unreported S100A4-dependent FcγRIIA receptor clustering and activation, thus preventing unwanted pro-inflammatory cytokine release and improving the safety profile of the antibody. The FcγRIIA receptor clustering and activation by the humanized IgG4 antibody is also significantly decreased compared to that elicited by murine IgG1 anti-S100A4 antibodies.

In one aspect is provided an isolated antibody comprising:
a) a heavy chain variable (VH) region comprising:
  i. a heavy chain complementarity-determining region 1 (CDR-H1) comprising or consisting of the amino acid sequence of SEQ ID NO: 1 or SEQ ID NO: 4;
  ii. a heavy chain complementarity-determining region 2 (CDR-H2) comprising or consisting of the amino acid sequence of SEQ ID NO: 2 or SEQ ID NO: 5; and
  iii. a heavy chain complementarity-determining region 3 (CDR-H3) comprising or consisting of the amino acid sequence of SEQ ID NO: 3 or SEQ ID NO: 6; and
b) a light chain variable (VL) region comprising:
  i. a CDR-L1 comprising or consisting of the amino acid sequence of SEQ ID NO: 7 or SEQ ID NO: 10;
  ii. a CDR-L2 comprising or consisting of the amino acid sequence of SEQ ID NO: 8 or YTS; and
  iii. a CDR-L3 comprising or consisting of the amino acid sequence of SEQ ID NO: 9 or SEQ ID NO: 12;
wherein the VH region comprises or consists of an amino acid sequence selected from the group consisting of SEQ ID NO: 13, SEQ ID NO: 14, SEQ ID NO: 15, SEQ ID NO: 16, SEQ ID NO: 17, and a variant of any one of SEQ ID NO:s 13 to 17, wherein any one amino acid not part of the CDR sequences as defined by SEQ ID NO:s 1 to 6 has been altered for another amino acid, with the proviso that no more than 5 amino acids have been so altered, for example wherein 5, 4, 3, 2, or 1 amino acid has been so altered in each amino acid sequence,
and/or wherein the VL region comprises or consists of an amino acid sequence selected from the group consisting of SEQ ID NO: 18, SEQ ID NO: 19, SEQ ID NO: 20, SEQ ID NO: 21, SEQ ID NO: 22, and a variant of any one of SEQ ID NO:s 18 to 22, wherein any one amino acid not part of the CDR sequences as defined by SEQ ID NO:s 7 to 12 has been altered for another amino acid, with the proviso that no more than 5 amino acids have been so altered, for example wherein 5, 4, 3, 2, or 1 amino acid has been so altered in each amino acid sequence.

In one aspect is provided an isolated antibody, comprising:
i. a heavy chain variable (VH) region comprising or consisting of an amino acid sequence selected from the group consisting of SEQ ID NO: 13, SEQ ID NO: 14, SEQ ID NO: 15, SEQ ID NO: 16, SEQ ID NO: 17, and a variant of any one of SEQ ID NO:s 13 to 17, wherein any one amino acid has been altered for another amino acid, with the proviso that no more than 5 amino acids have been so altered, for example wherein 5, 4, 3, 2, or 1 amino acid has been so altered in each amino acid sequence,
and
ii. a light chain variable (VL) region comprising or consisting of an amino acid sequence selected from the group consisting of SEQ ID NO: 18, SEQ ID NO: 19, SEQ ID NO: 20, SEQ ID NO: 21, SEQ ID NO: 22, and a variant of any one of SEQ ID NO:s 18 to 22, wherein any one amino acid has been altered for another amino acid, with the proviso that no more than 5 amino acids have been so altered, for example wherein 5, 4, 3, 2, or 1 amino acid has been so altered in each amino acid sequence.

In one aspect is provided an isolated nucleic acid molecule encoding the antibody as described herein above in the section 'Isolated anti-S100A4 antibody molecule'.

In one aspect is provided an expression vector comprising the nucleic acid molecule as described herein encoding an anti-S100A4 antibody molecule.

In one aspect is provided an isolated host cell comprising the isolated nucleic acid molecule or the expression vector as described herein.

In one aspect is provided a method of producing an anti-S100A4 antibody molecule, the method comprising culturing the host cell as described herein under conditions wherein the antibody is expressed.

In one aspect is provided a pharmaceutical composition comprising the antibody, the nucleic acid molecule, the expression vector and/or the host cell as described herein, and a pharmaceutically acceptable diluent, carrier and/or excipient.

In one aspect is also provided a method of treatment of an individual with an S100A4-mediated condition, said method comprising administering the antibody or the host cell as described herein to an individual in need thereof.

In one aspect is provided a method for diagnosis or prognosis of an S100A4-related condition in an individual, the method comprising
  (a) contacting a biological sample from the individual with an anti-S100A4 antibody as described herein, which is capable of binding to S100A4 polypeptide present in the sample; and
  (b) determining the presence and/or amount of the complex formed between the antibody molecule and the S100A4 polypeptide.

Figure 1A:
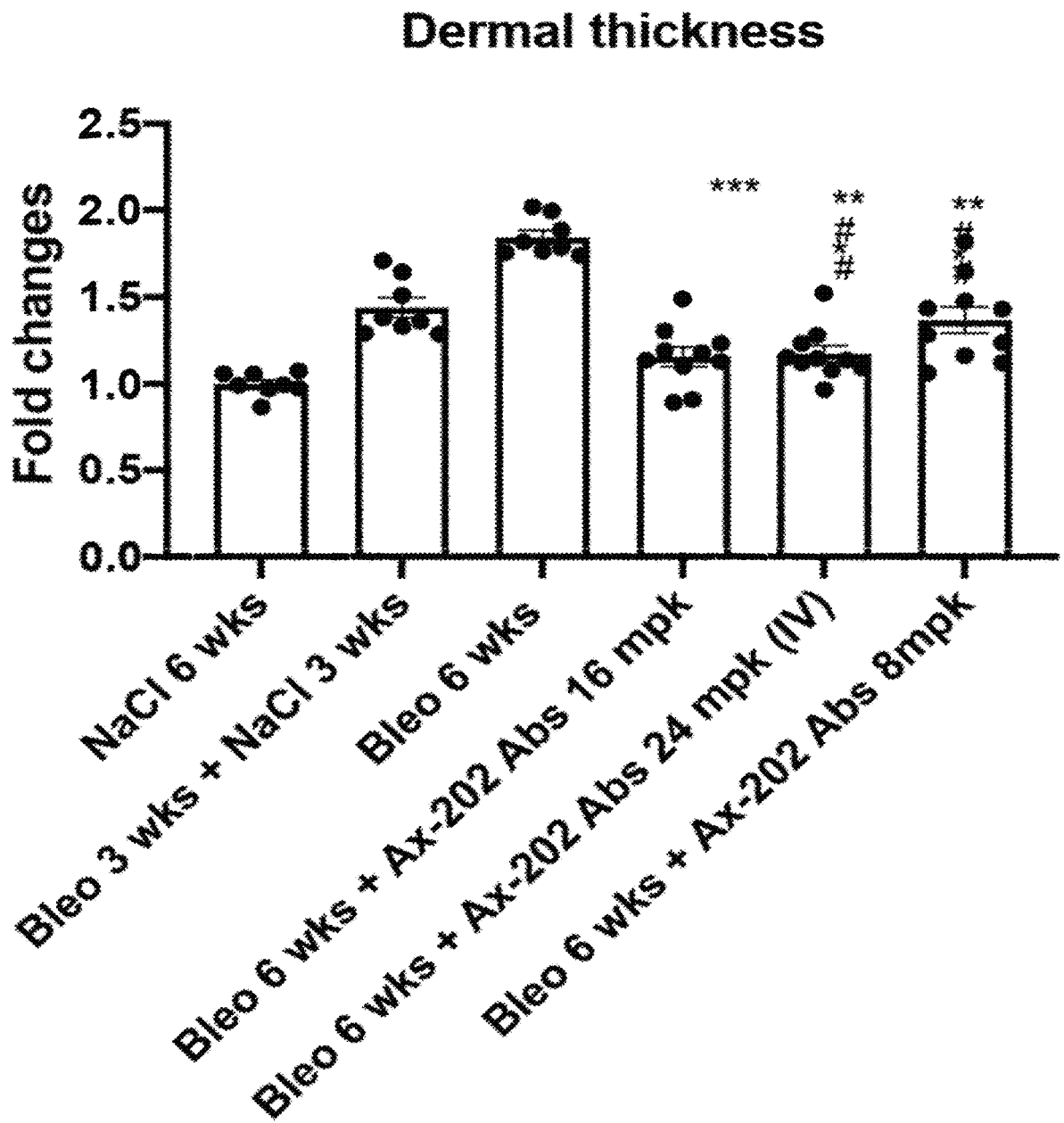
FIGS. 1A-1E show the effects of monoclonal humanized anti-S100A4 antibodies on fibrotic readouts in bleomycin-challenged mice. Effects of anti-S100A4 antibodies on dermal thickness (FIG. 1A), myofibroblast counts (FIG. 1B)
Figure 1B:
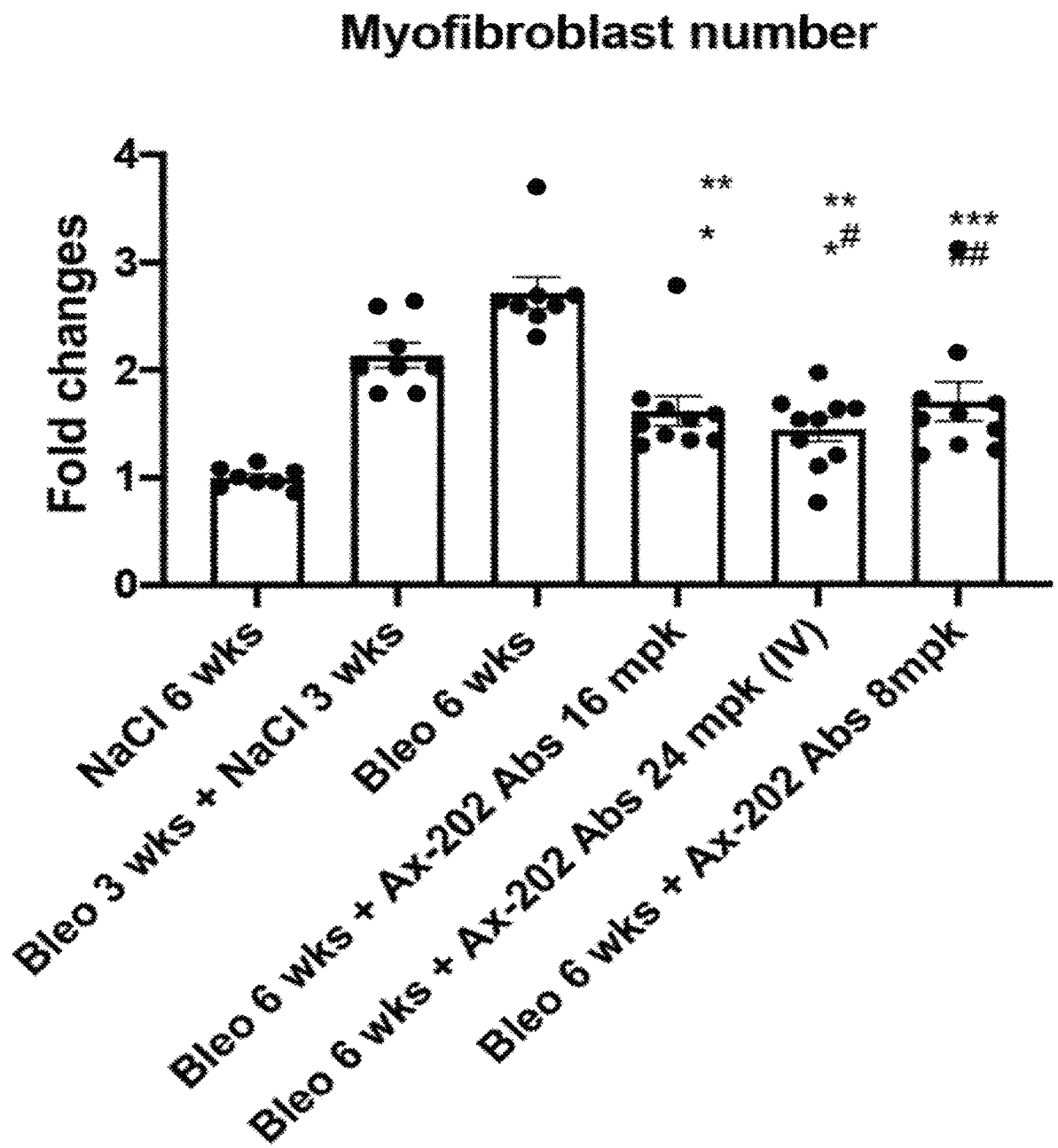
Figure 1C:
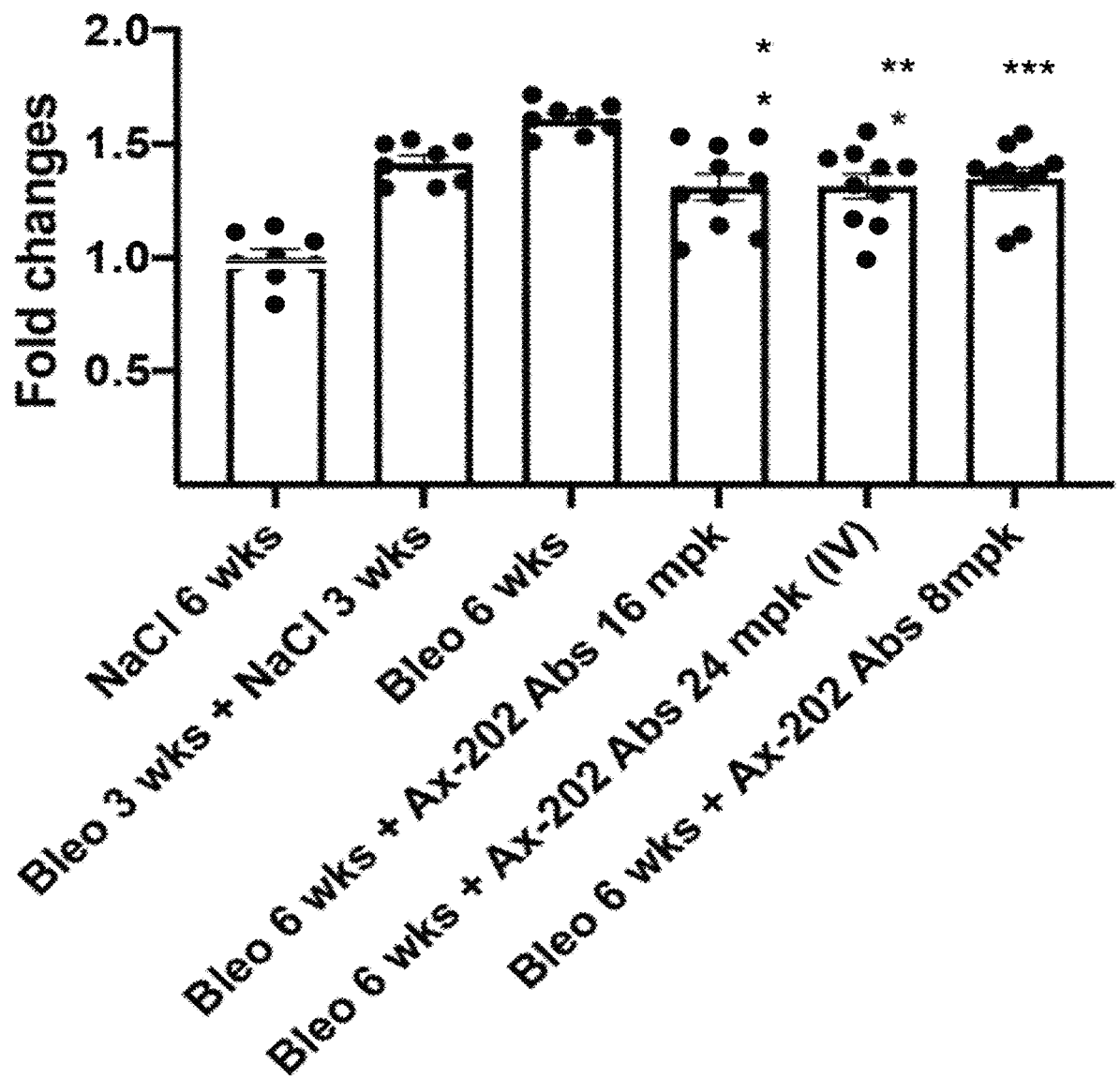
Figure 1D:
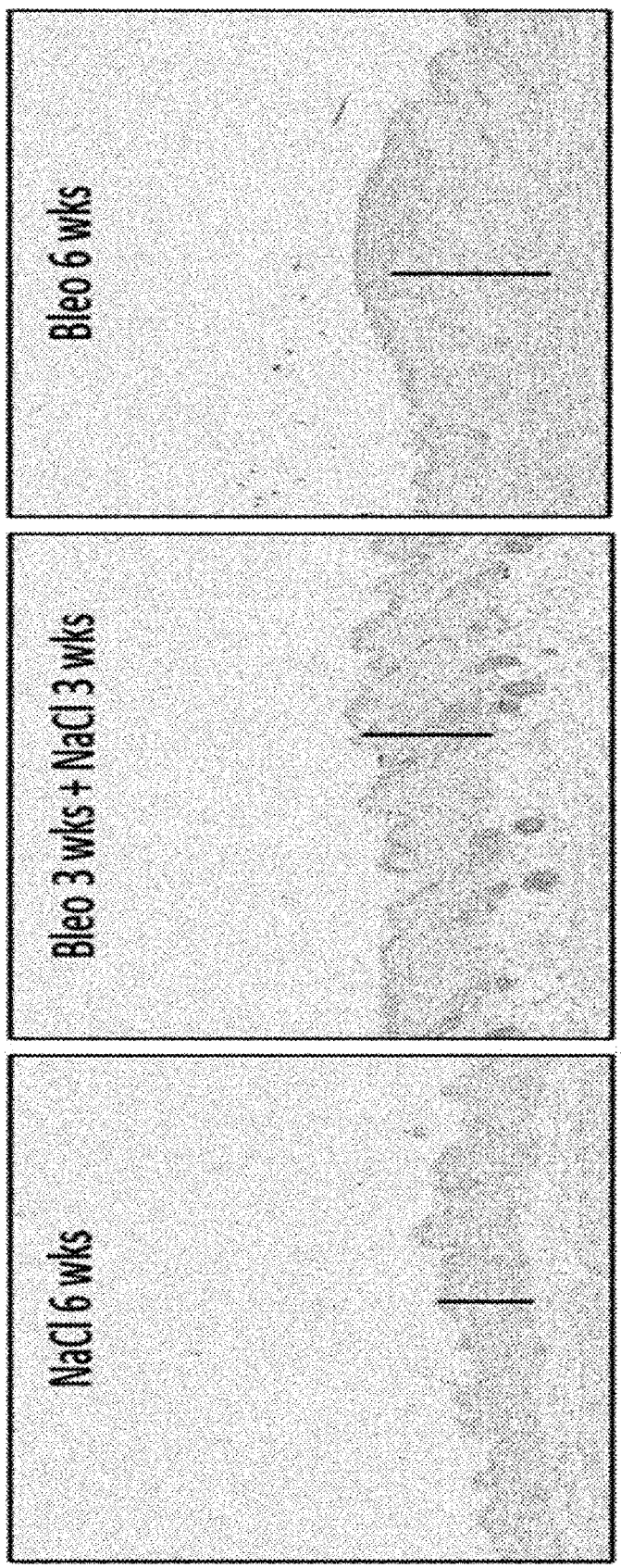
Figure 1E:
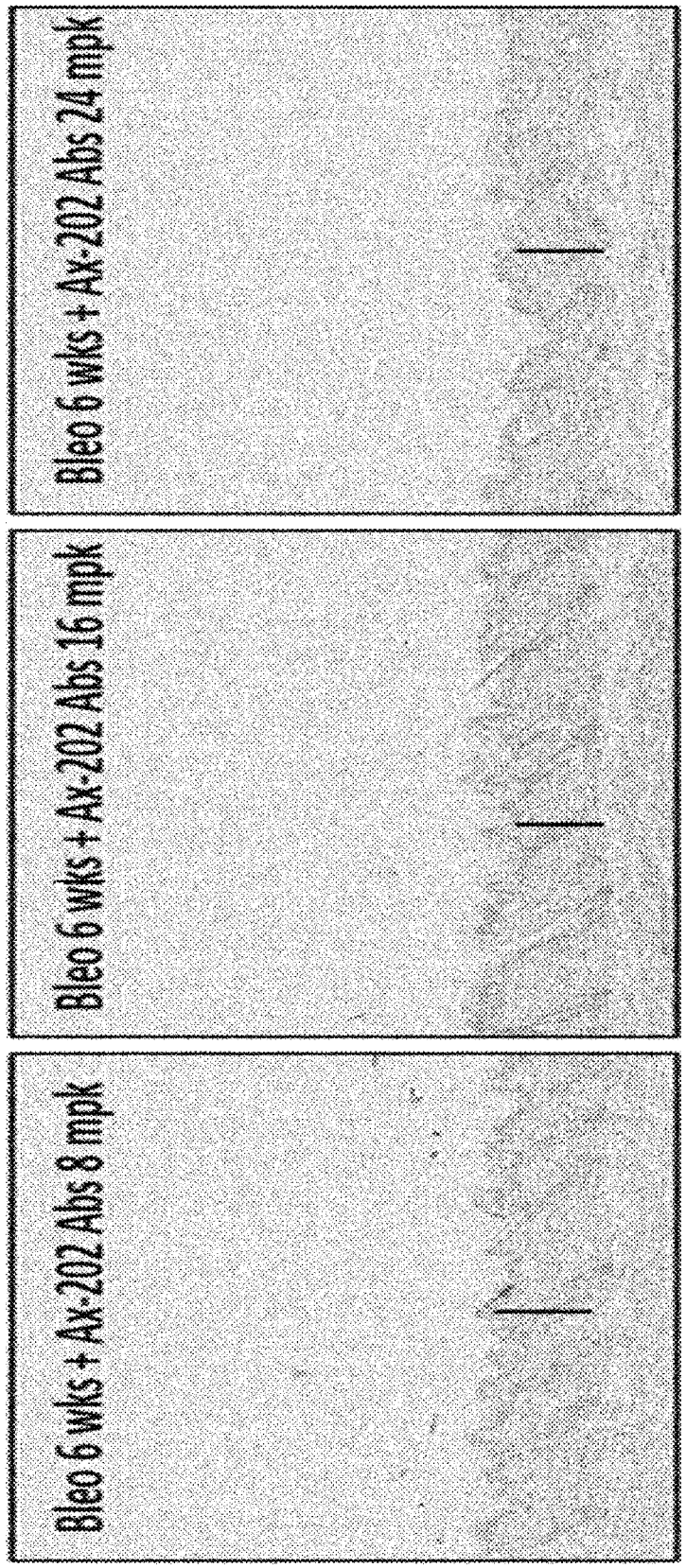
Figure 2A:
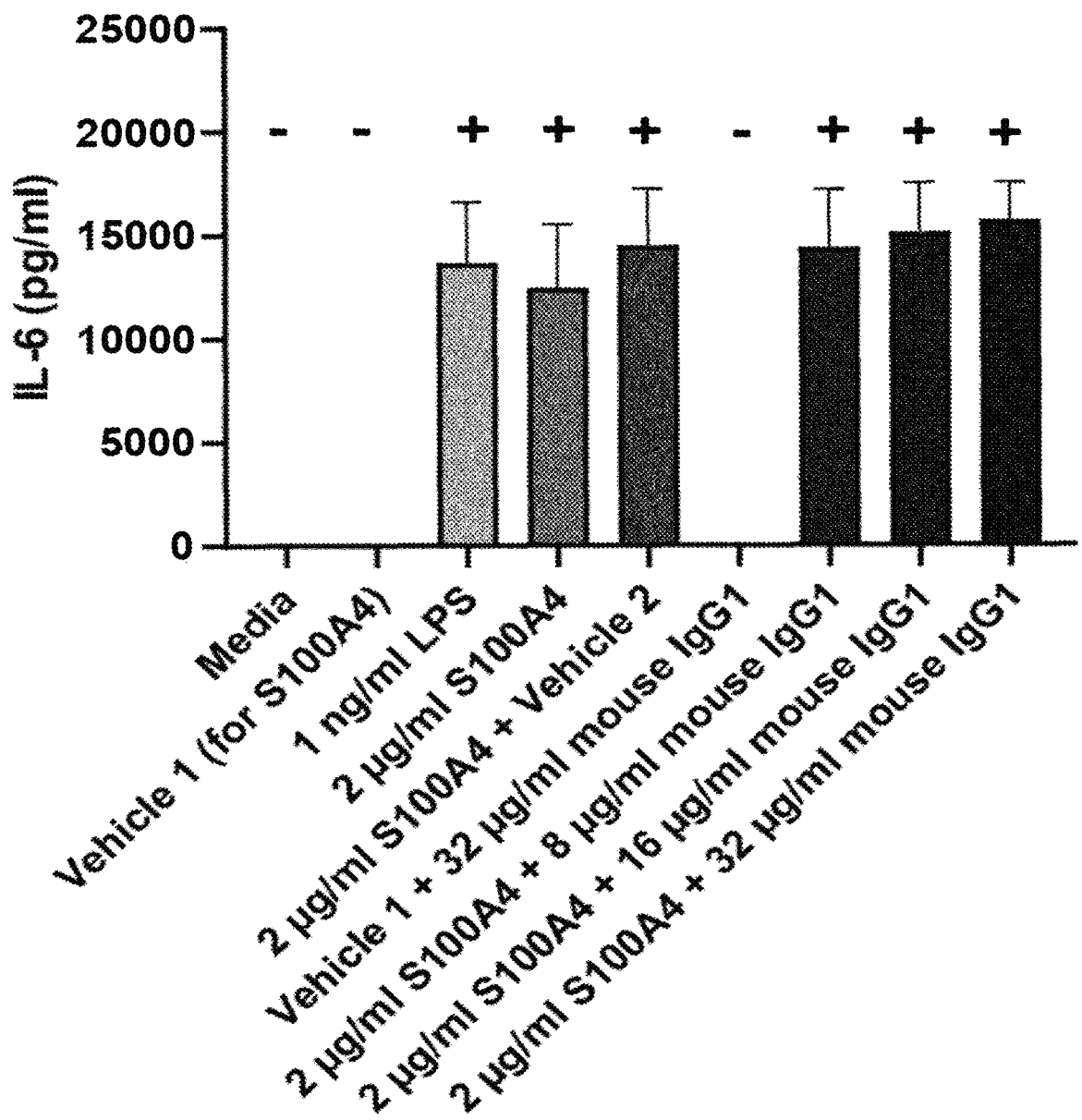
Figure 2B:
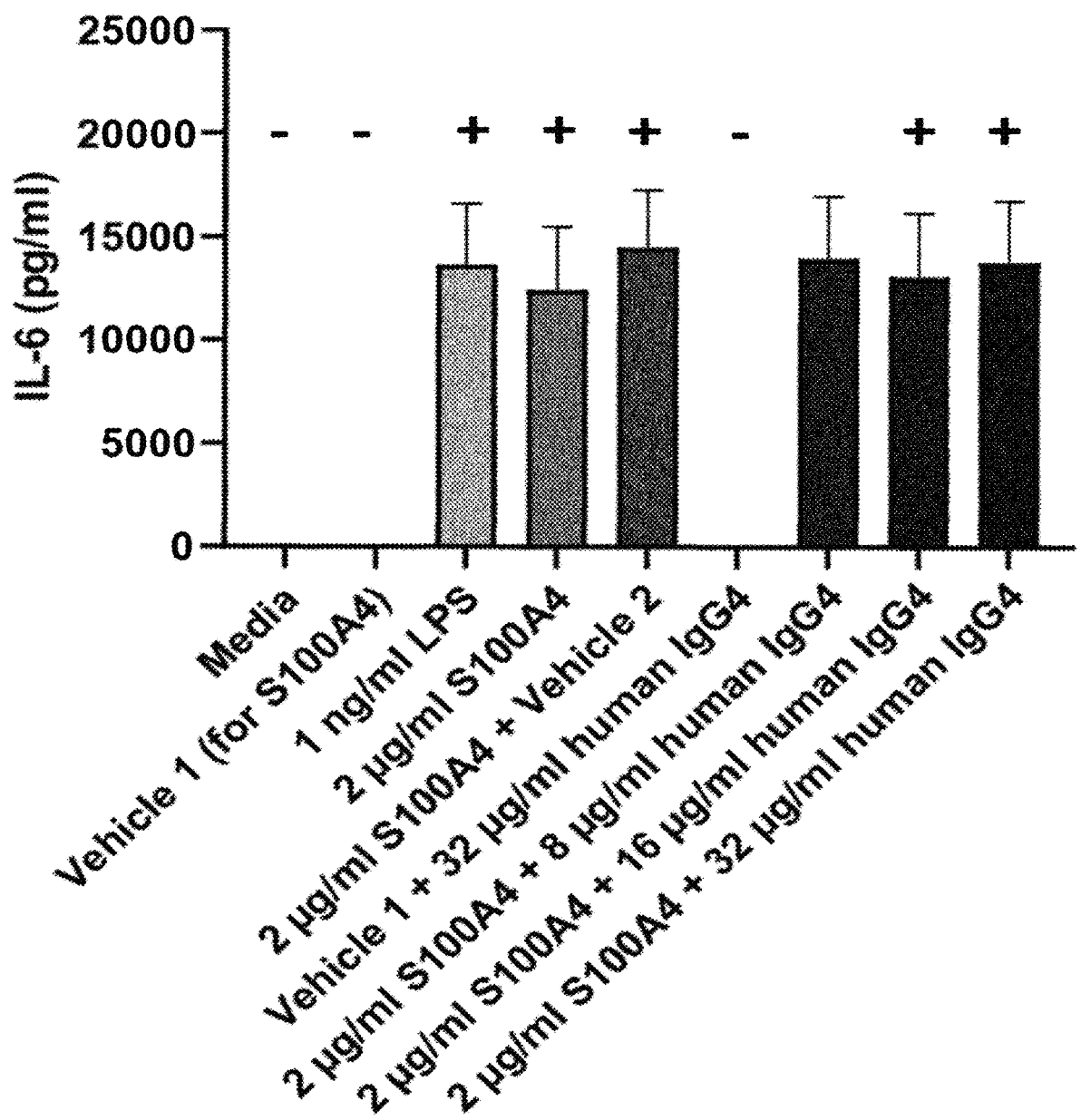
Figure 2C:
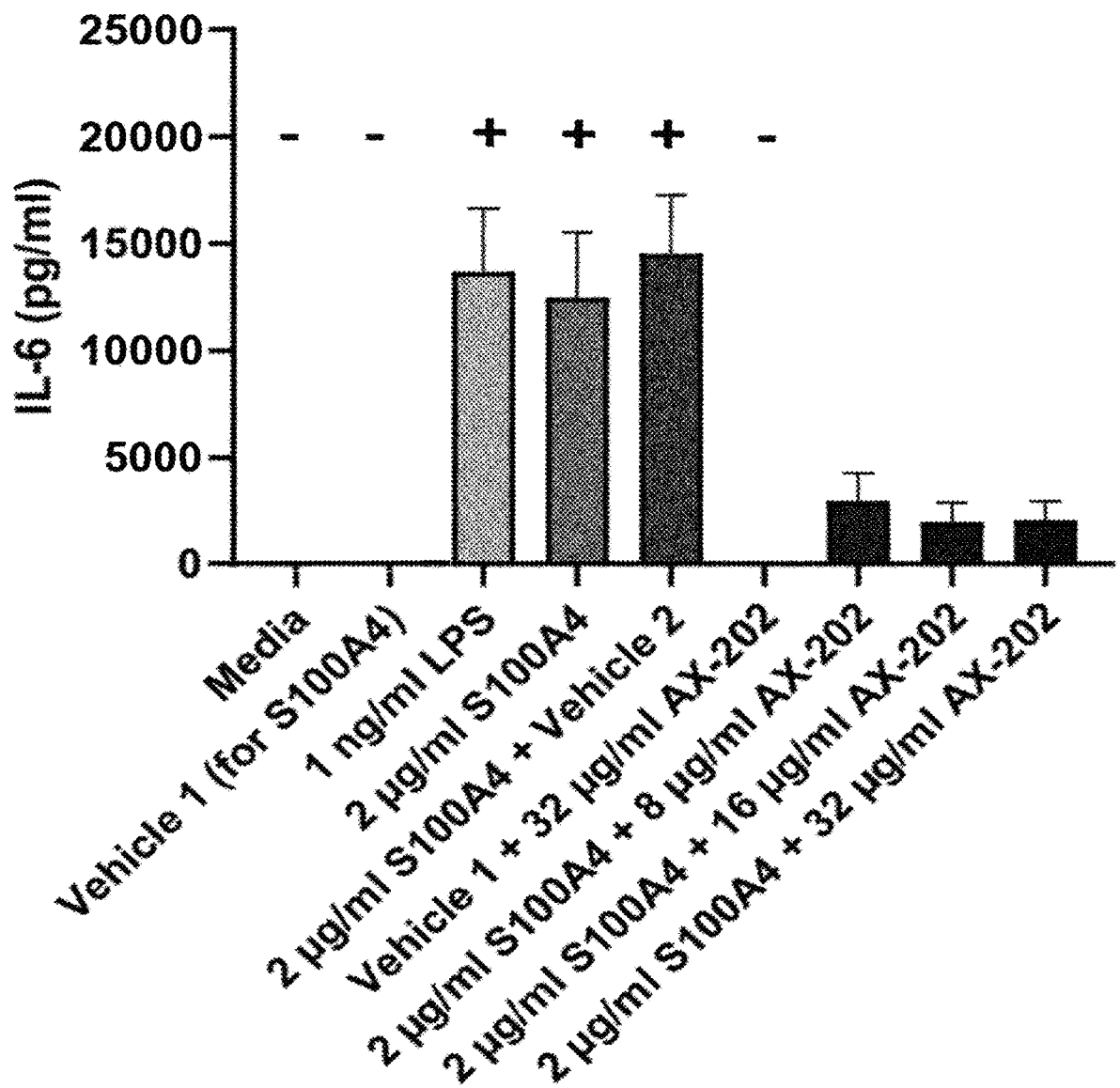
Figure 2D:
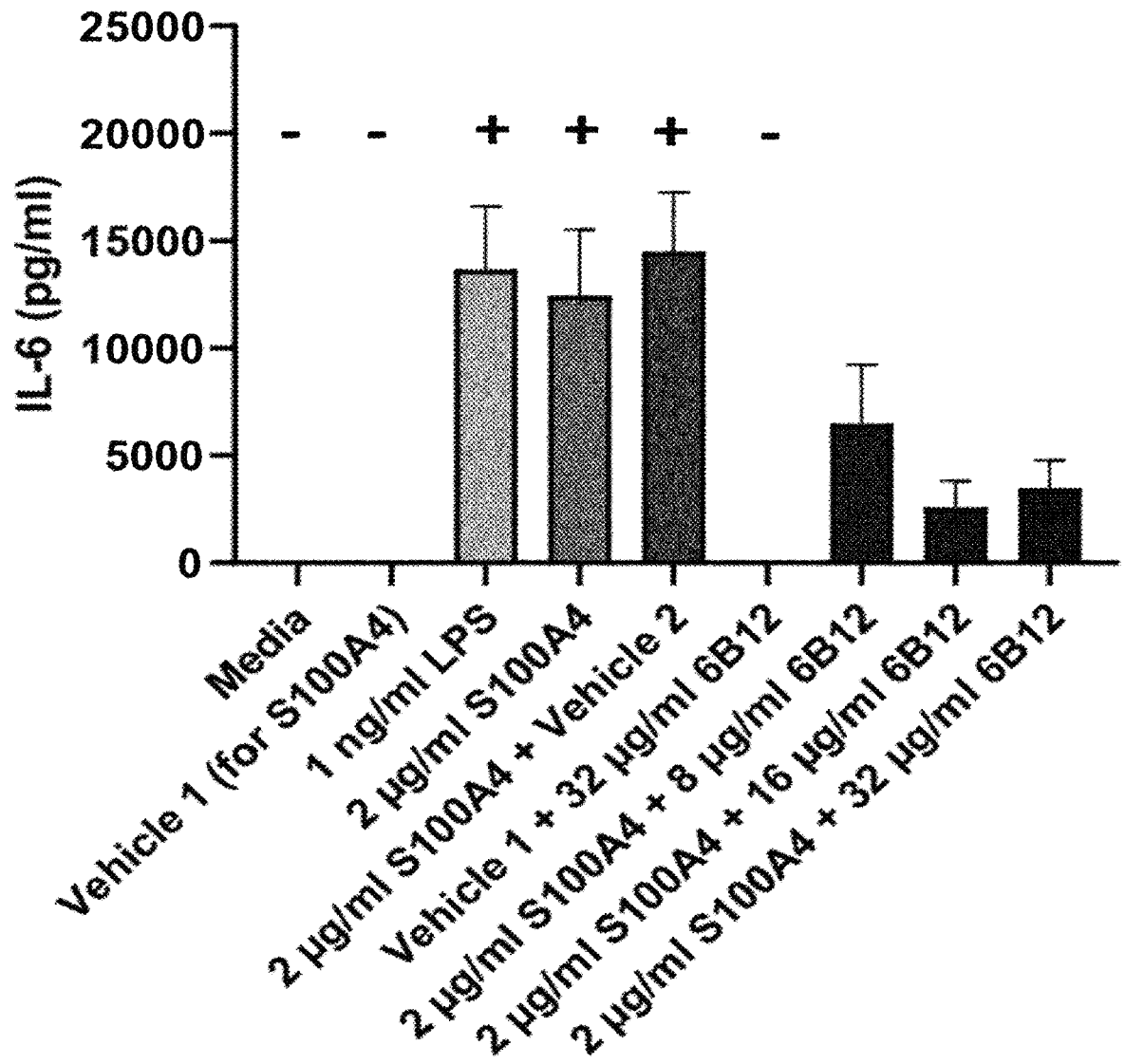
Figure 3A:
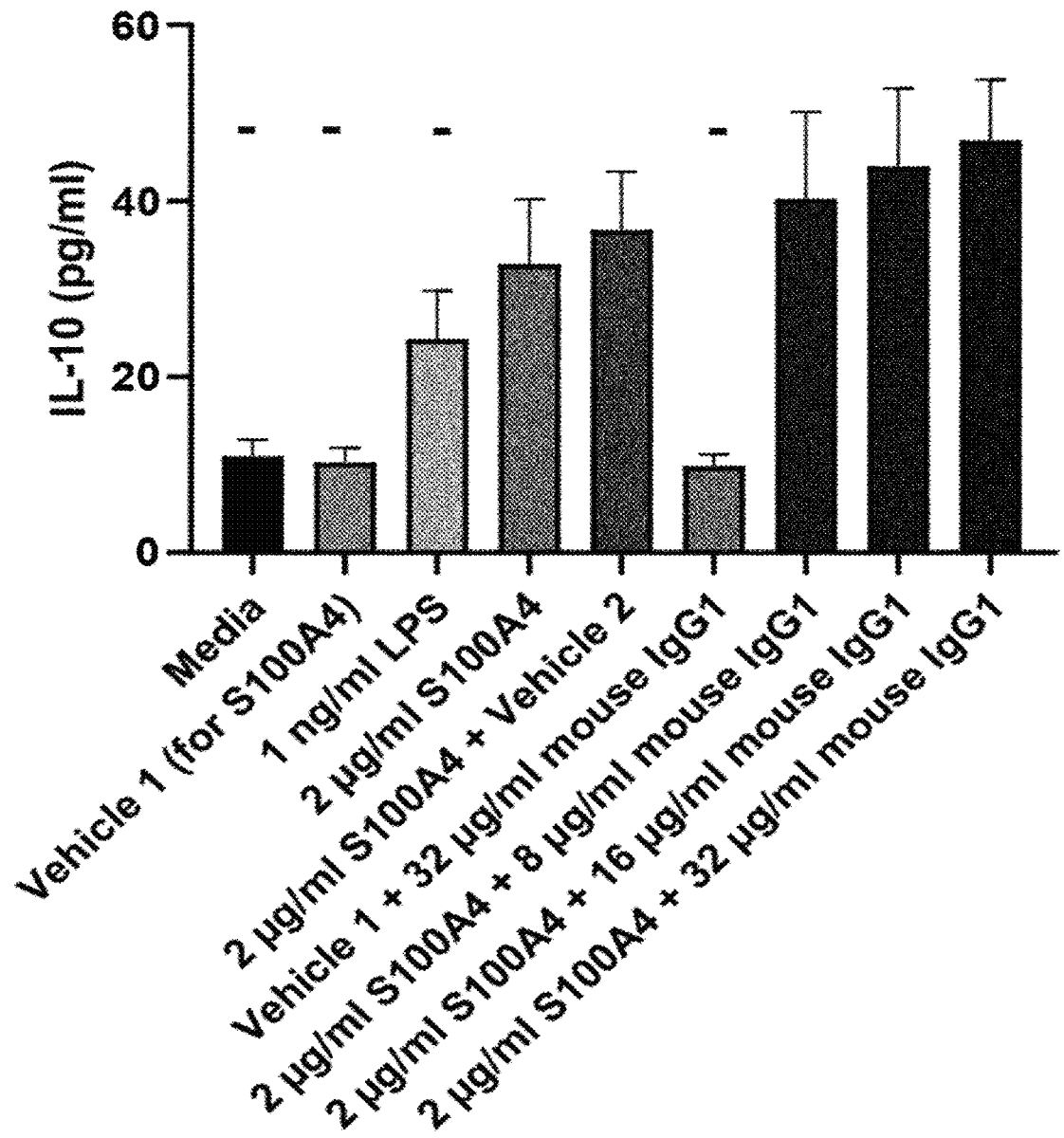
Figure 3B:
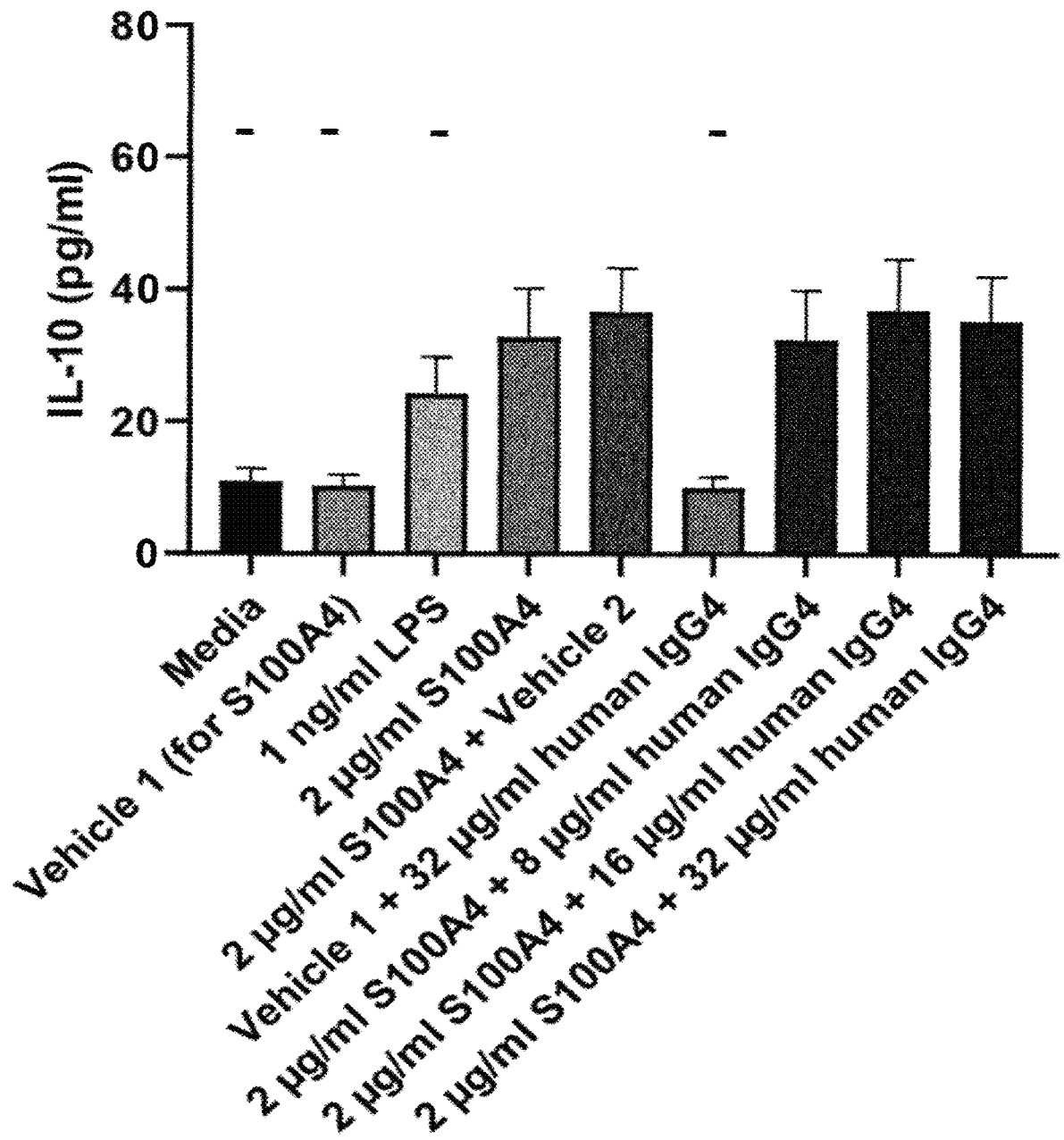
Figure 3C:
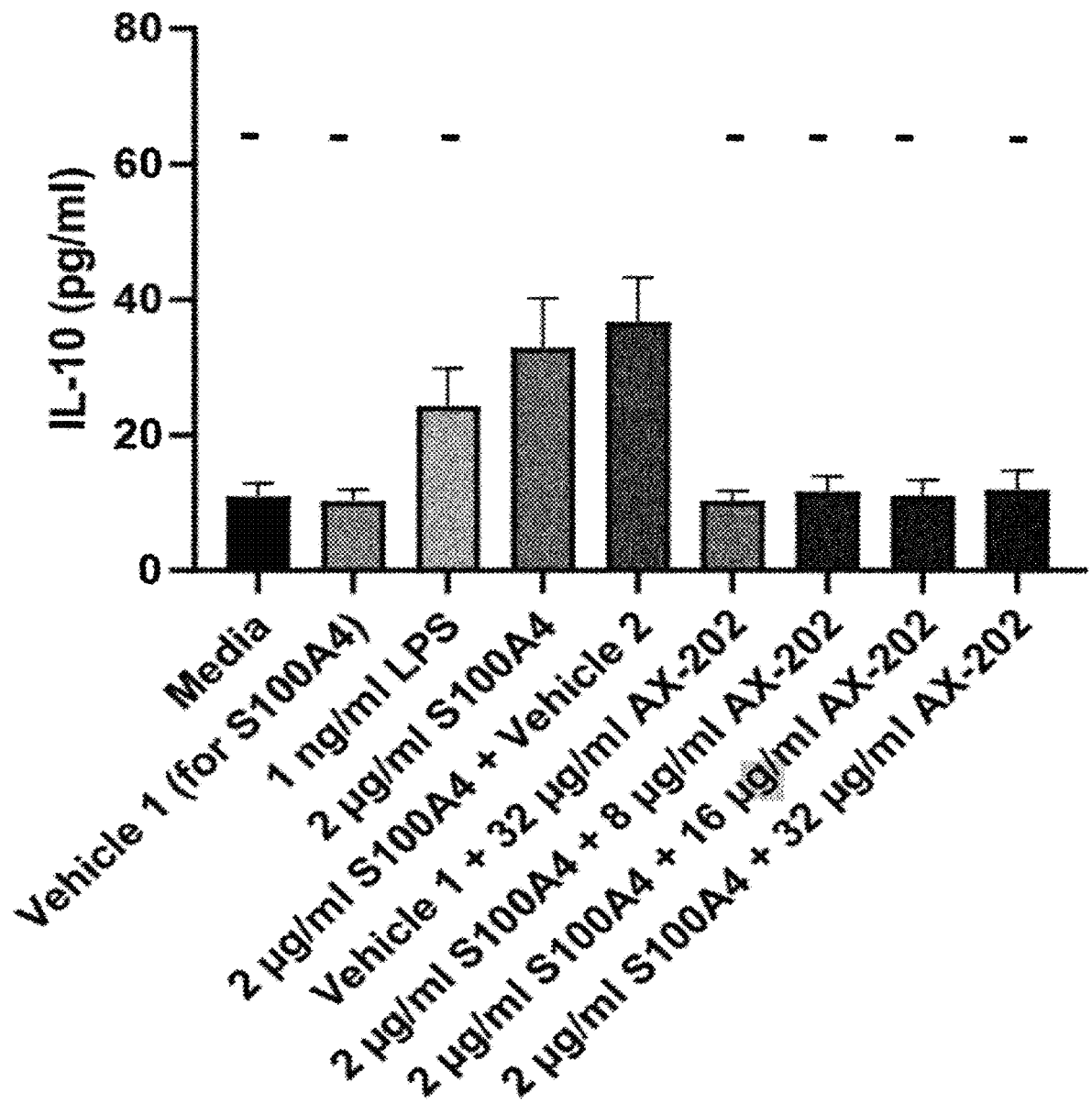
Figure 3D:
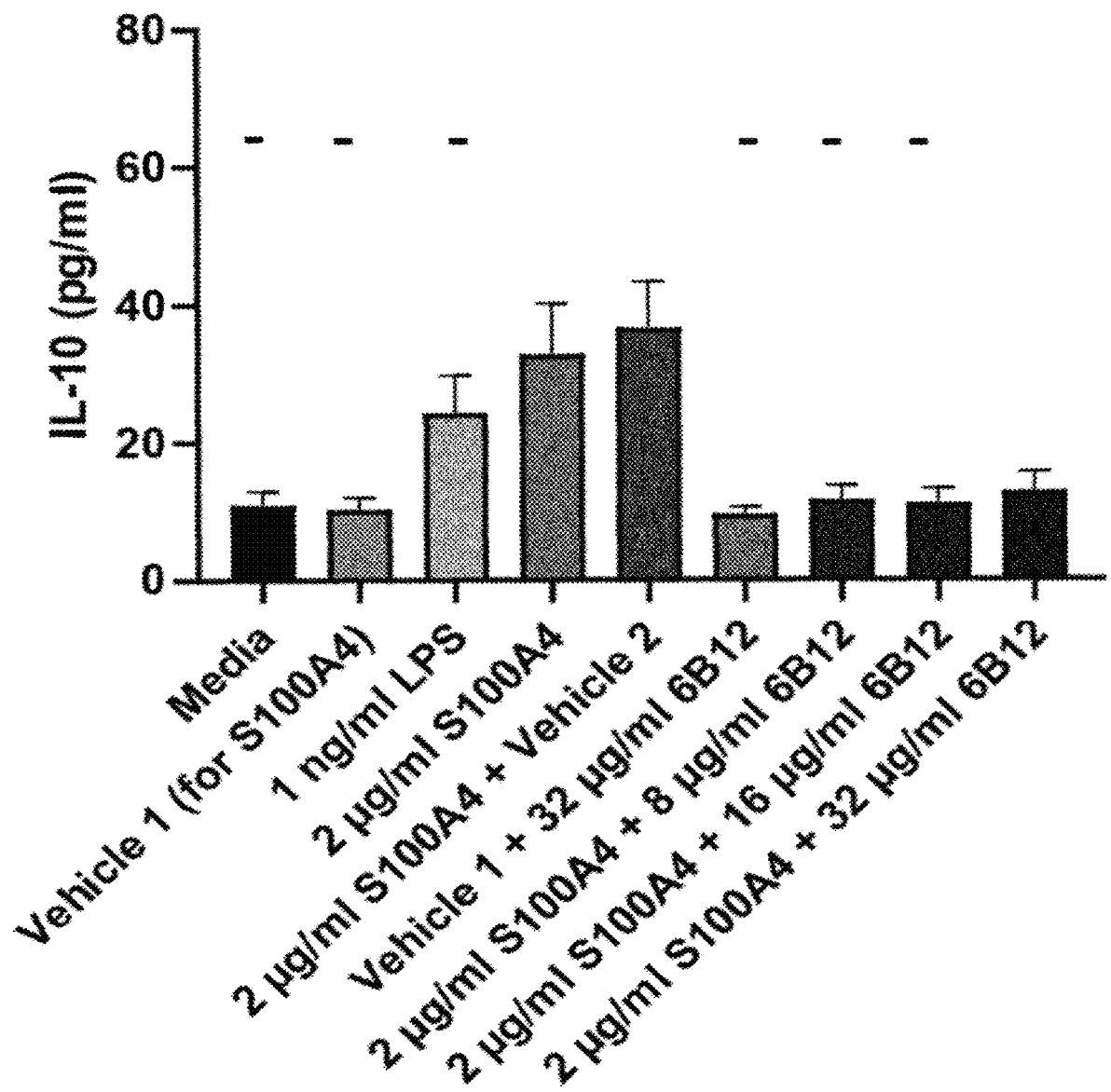

and hydroxyproline content (FIG. 1C). Representative images of HE stained skin sections are shown in FIG. 1D and FIG. 1E. P-values are expressed as follows: 0.05>p>0.01 as *; 0.01>p>0.001 as ** as compared to NaCl; 0.05>p>0.01 as #; 0.01>p>0.001 as ## as compared to mice injected with bleomycin for three weeks followed by injections of NaCl for another 3 weeks. The results are further described in Example 3.

FIGS. 2A-2D show IL-6 secretion by monocytes analysed by Luminex analysis. Data shown is the average of 5 donors. Monocytes purified from PBMC were cultured with media, vehicle, LPS, S100A4 in the absence or presence of mouse IgG1 (FIG. 2A), human IgG4 (FIG. 2B), AX-202 (FIG. 2C) or 6B12 (FIG. 2D) for 6 hours. Data shows levels of IL-6 in the supernatant quantified by Luminex assay. Data presented as mean+SEM arising from five independent donors. "+" indicates at least one donor above the limit of detection for IL-6 (19,200 µg/mL). "−" indicates at least one donor below the limit of detection for IL-6 (8.8 pg/mL). The results are further described in Example 4.

FIGS. 3A-3D show IL-10 secretion by monocytes analysed by Luminex analysis. Data shown is the average of 5 donors. Monocytes purified from PBMC were cultured with media, vehicle, LPS, S100A4 in the absence or presence of mouse IgG1 (FIG. 3A), human IgG4 (FIG. 3B), AX-202 (FIG. 3C) or 6B12 (FIG. 3D) for 6 hours. Data shows IL-10 of cytokine in the supernatant quantified by Luminex assay. Data presented as mean+SEM arising from five independent donors. "−" indicates at least one donor below the limit of detection for IL-10 (8.6 pg/mL). The results are further described in Example 4.

FIGS. 4A-4D show TNF-α secretion by monocytes analysed by Luminex analysis. Data shown is the average of 5 donors. Monocytes purified from PBMC were cultured with media, vehicle, LPS, S100A4 in the absence or presence of mouse IgG1 (FIG. 4A), human IgG4 (FIG. 4B), AX-202 (FIG. 4C) or 6B12 (FIG. 4D) for 6 hours. Data shows levels of TNF-α in the supernatant quantified by Luminex assay. Data presented as mean+SEM arising from five independent donors. "−" indicates at least one donor below the limit of detection for TNF-α (15.20 pg/ml). The results are further described in Example 4.

Figure 5:
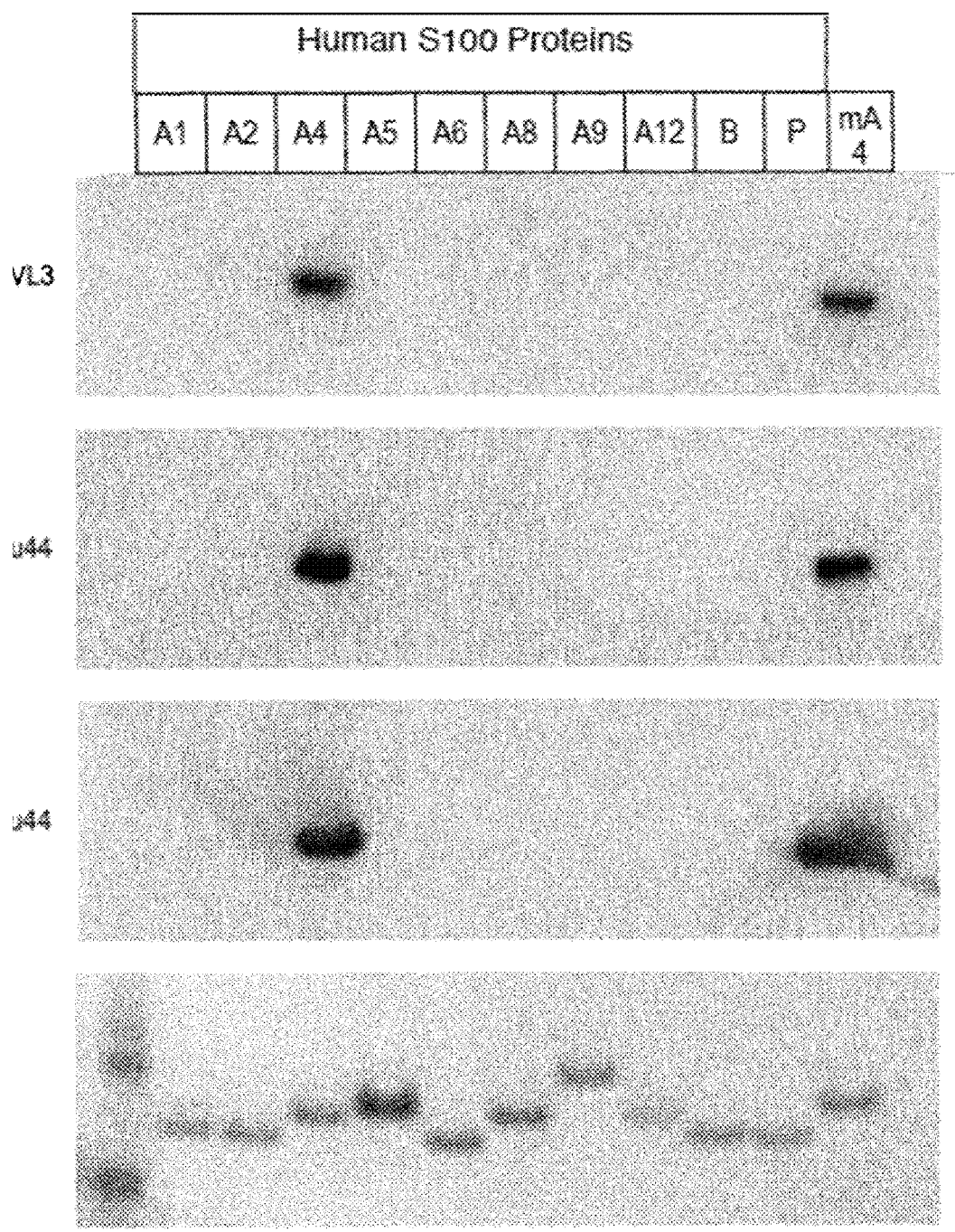

FIG. 5 shows the specificity of three humanized variants of 6B12 mAb to different other S100 family members as measured by Western blotting. The results are further described in Example 5.

Figure 6:
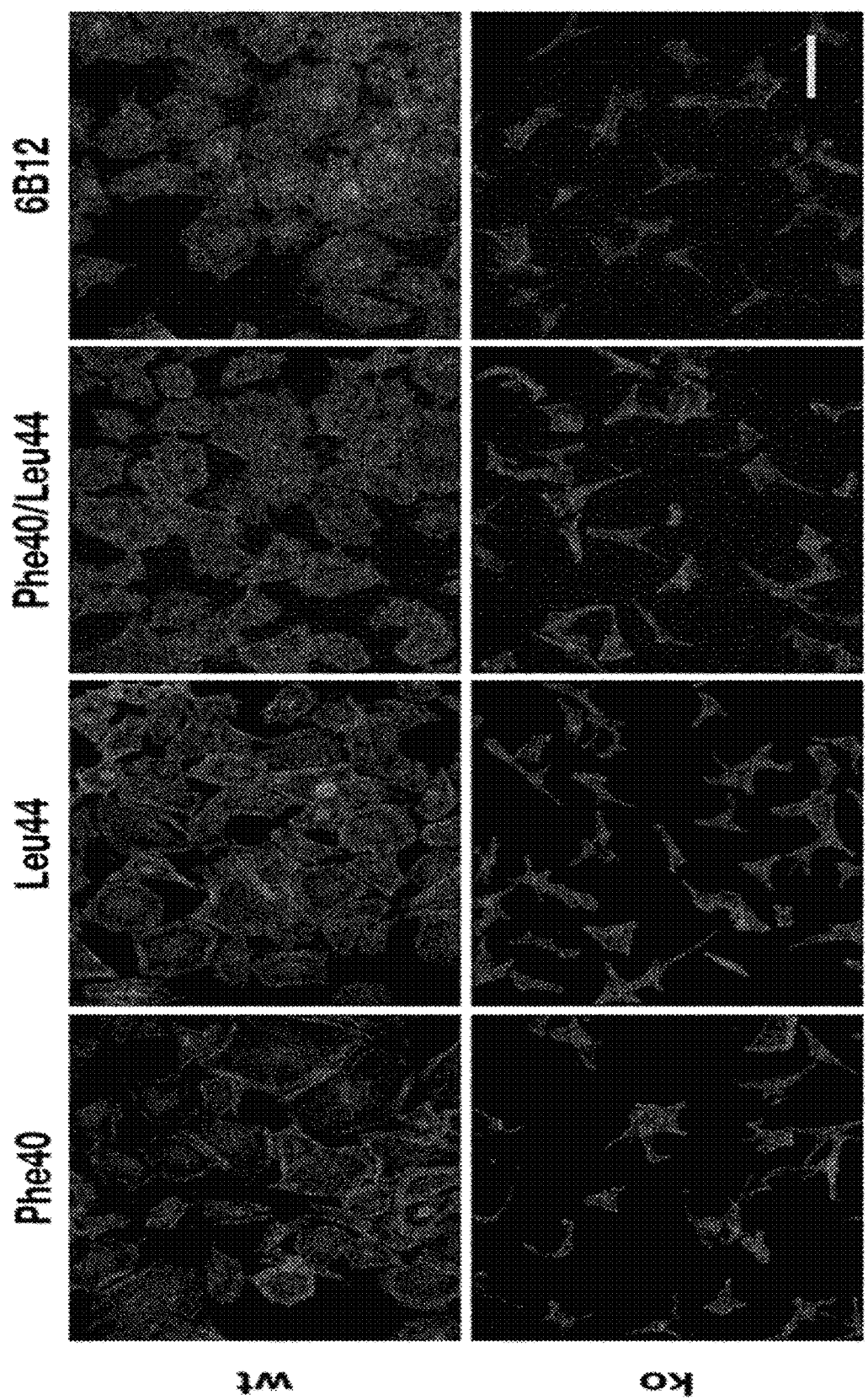

FIG. 6 shows human variants are specific to the S100A4 protein and that they do not cross-react with random cellular proteins as shown in wild-type (wt) and S100A4 knock-out (ko) mouse embryonic fibroblasts (MEFs). Cells are counterstained with DAPI and the actin cytoskeleton by Phalloidine. The parental monoclonal mouse anti-S100A4 antibody (6B12) served as control. Bar=100 µm. The results are further described in Example 5.

Figure 7A:
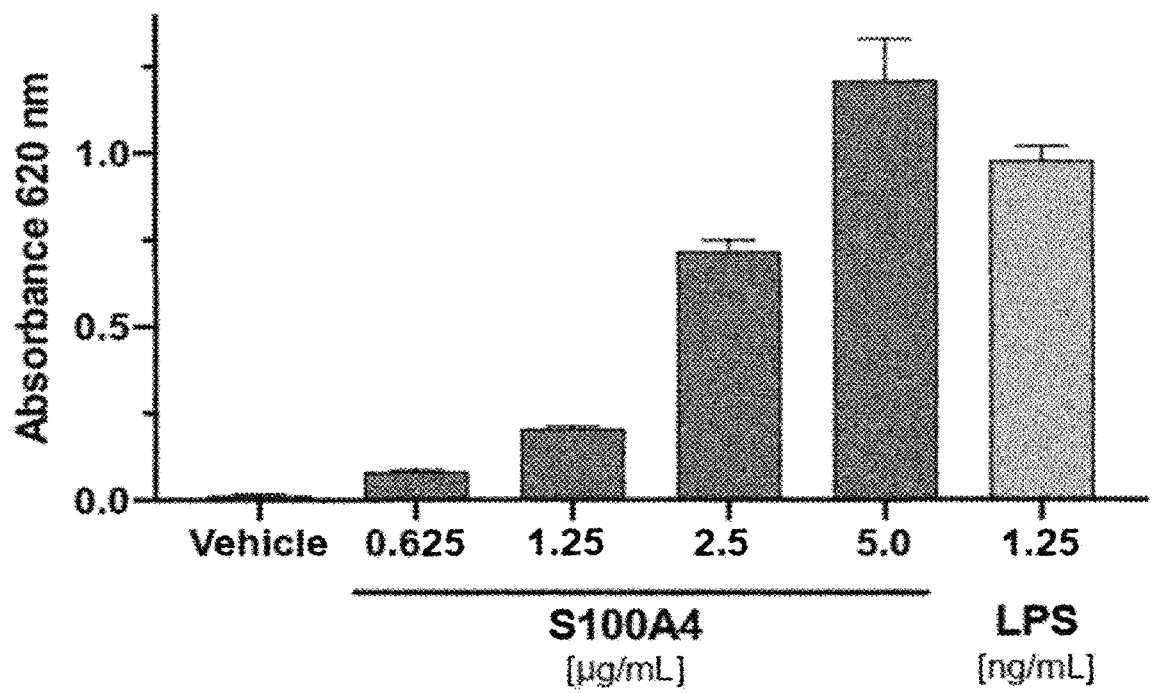
Figure 7B:
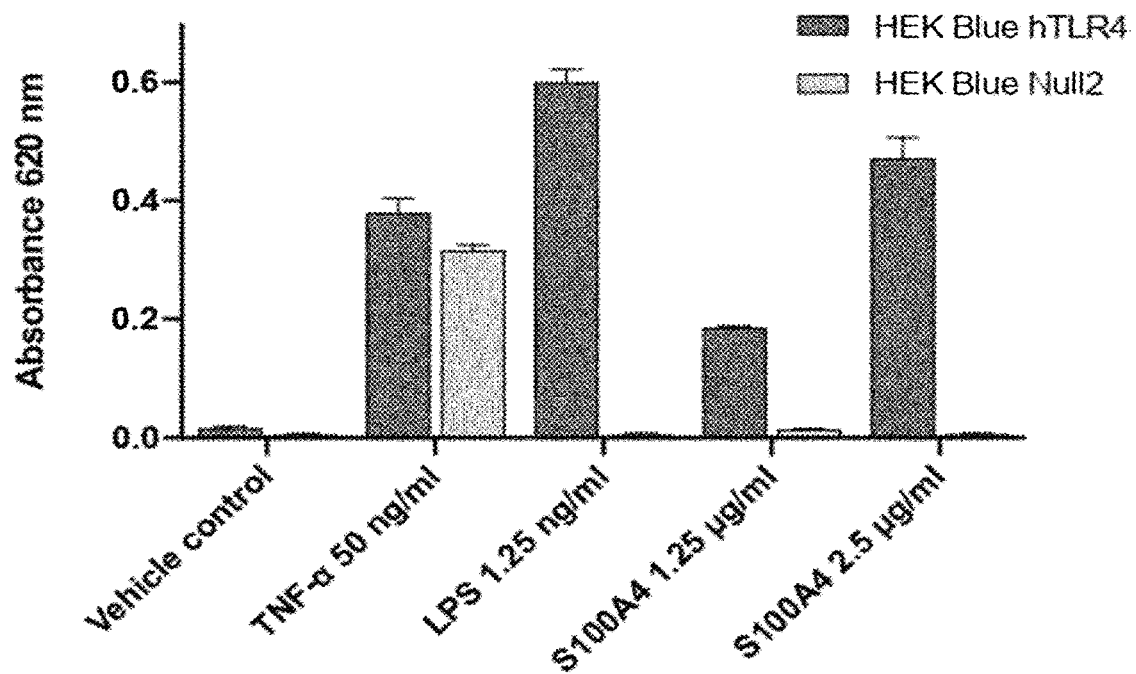
Figure 7C:
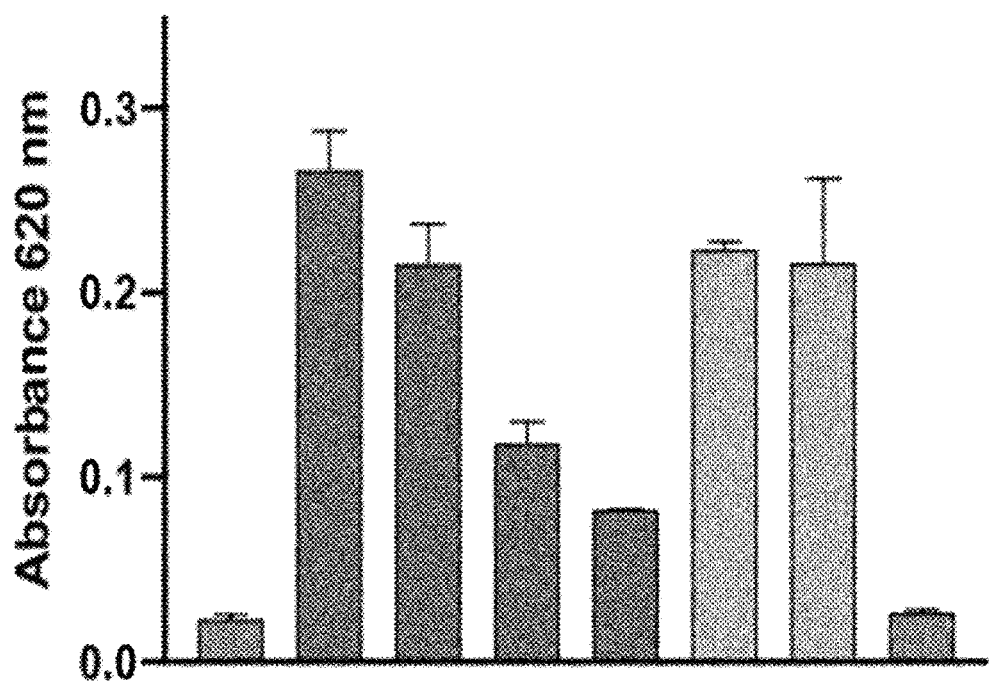

FIGS. 7A-7C show that AX-202 inhibits S100A4-induced TLR4 activation in a concentration-dependent manner. (FIG. 7A) S100A4 activates NF-kB reporter gene in HEK-Blue hTLR4 cells in a concentration-dependent manner. (FIG. 7B) S100A4 activation of the NF-kB reporter gene is dependent on TLR4. (FIG. 7C) AX-202 inhibits S100A4-induced TLR4 activation in a concentration-dependent manner. The results are further described in Example 6.

Figure 8:
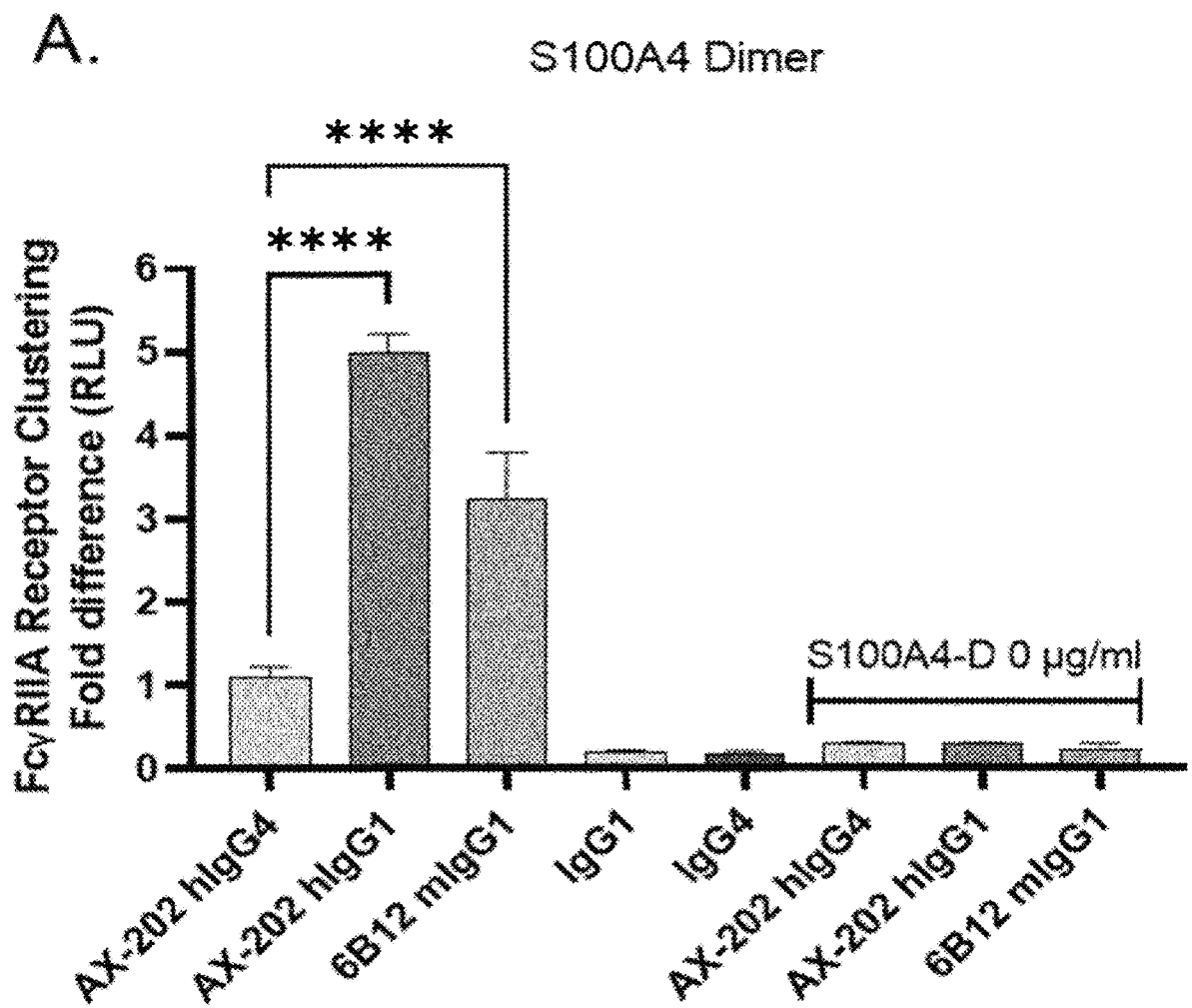
Figure 8:
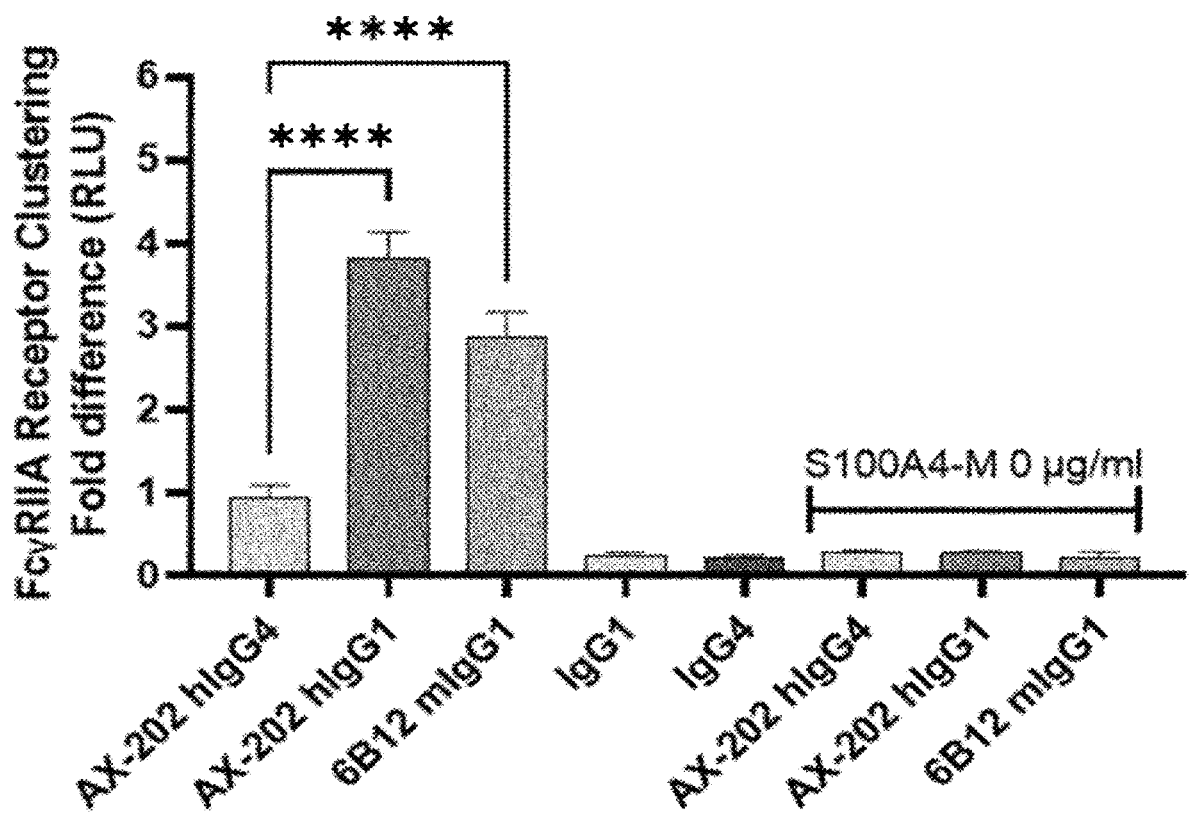

FIG. 8 shows a comparison of the FcγIIaR binding activity for 2 µg/ml 6B12 mIgG1, AX-202 hIgG1 and AX-202 hIgG4 when combined with either 2.5 µg/ml recombinant human S100A4 dimer (panel A) or multimer (panel B). The control IgG1 or IgG4 antibodies did not mediate receptor clustering and activation. The results are further described in Example 7. Bars indicate SD. Results presented as mean±SD n=3 independent studies. For controls with 0 µg/ml S100A4 n=2.

DETAILED DESCRIPTION OF THE INVENTION

Definitions

As used herein, the singular forms "a" "an" and "the" include plural referents unless the context clearly states otherwise. Thus, for example, reference to "an antibody" includes a plurality of such antibodies.

The protein S100A4 is also known as 18A2, 42A, CAPL, FSP1, MTS1, P9KA, PEL98 and S100 calcium binding protein A4.

The term "isolated" refers to a compound which can be e.g. an antibody or an antigen binding moiety that is substantially free of other antibodies or antigen binding moieties having different antigenic specificities. Moreover, an isolated antibody antigen binding moiety may be substantially free of other cellular material and/or chemicals.

Operably linked as defined herein refers to the mentioned elements being joined as part of the same nucleic acid molecule, suitably positioned and oriented for transcription to be initiated from the promoter. DNA operably linked to a promoter is under transcriptional initiation regulation of the promoter or in functional combination therewith.

As used herein, the term "variant" defines either a naturally occurring genetic mutant of a DNA sequence or its encoded RNA or protein product, or a recombinantly prepared variation of a DNA sequence or its encoded RNA or protein product. The term "variant" may also refer to either a naturally occurring variation of a given peptide or a recombinantly prepared variation of a given peptide or protein in which one or more amino acid residues have been modified by amino acid substitution, addition, or deletion.

"Inhibition" as used herein means that the presence of the antibody of the invention inhibits, in whole or in part, the binding of ligands to their receptor and/or the disablement of a signal the receptor would elicit upon ligand binding. This includes for example down-stream signalling having effect on cellular behaviour and processes. Also included are other mechanisms of inhibiting the downstream effects of the targeted molecule, such as by blocking dimerization, oligomerization and/or multimerization of the target molecule. "Inhibition", "blocking" and "neutralizing" are used herein as equivalent terms.

Isolated Anti-S100A4 Antibody Molecule

In one aspect is provided an isolated antibody comprising:
a) a heavy chain variable (VH) region comprising:
  i. a heavy chain complementarity-determining region 1 (CDR-H1) comprising or consisting of the amino acid sequence of SEQ ID NO: 1 or SEQ ID NO: 4;
  ii. a heavy chain complementarity-determining region 2 (CDR-H2) comprising or consisting of the amino acid sequence of SEQ ID NO: 2 or SEQ ID NO: 5; and
  iii. a heavy chain complementarity-determining region 3 (CDR-H3) comprising or consisting of the amino acid sequence of SEQ ID NO: 3 or SEQ ID NO: 6; and
b) a light chain variable (VL) region comprising:
  i. a CDR-L1 comprising or consisting of the amino acid sequence of SEQ ID NO: 7 or SEQ ID NO: 10;

ii. a CDR-L2 comprising or consisting of the amino acid sequence of SEQ ID NO: 8 or YTS; and iii. a CDR-L3 comprising or consisting of the amino acid sequence of SEQ ID NO: 9 or SEQ ID NO: 12;

wherein the VH region comprises or consists of an amino acid sequence selected from the group consisting of SEQ ID NO: 13, SEQ ID NO: 14, SEQ ID NO: 15, SEQ ID NO: 16, SEQ ID NO: 17, and a variant of any one of SEQ ID NO:s 13 to 17, wherein any one amino acid not part of the CDR sequences as defined by SEQ ID NO:s 1 to 6 has been altered for another amino acid, with the proviso that no more than 5 amino acids have been so altered, for example wherein 5, 4, 3, 2, or 1 amino acid has been so altered in each amino acid sequence, and/or wherein the VL region comprises or consists of an amino acid sequence selected from the group consisting of SEQ ID NO: 18, SEQ ID NO: 19, SEQ ID NO: 20, SEQ ID NO: 21, SEQ ID NO: 22, and a variant of any one of SEQ ID NO:s 18 to 22, wherein any one amino acid not part of the CDR sequences as defined by SEQ ID NO:s 7 to 12 has been altered for another amino acid, with the proviso that no more than 5 amino acids have been so altered, for example wherein 5, 4, 3, 2, or 1 amino acid has been so altered in each amino acid sequence.

In some embodiments, the heavy chain variable (VH) region of the isolated antibody comprises:
i. a heavy chain complementarity-determining region 1 (CDR-H1) comprising or consisting of the amino acid sequence of SEQ ID NO: 1;
ii. a heavy chain complementarity-determining region 2 (CDR-H2) comprising or consisting of the amino acid sequence of SEQ ID NO: 2; and
iii. a heavy chain complementarity-determining region 3 (CDR-H3) comprising or consisting of the amino acid sequence of SEQ ID NO: 3;

and the light chain variable (VL) region comprises a light chain variable (VL) region comprising:
i. a light chain complementarity-determining region 1 (CDR-L1) comprising or consisting of the amino acid sequence of SEQ ID NO: 7;
ii. a light chain complementarity-determining region 2 (CDR-L2) comprising or consisting of the amino acid sequence of SEQ ID NO: 8; and
iii. a light chain complementarity-determining region 3 (CDR-L3) comprising or consisting of the amino acid sequence of SEQ ID NO: 9.

In some embodiments, the heavy chain variable (VH) region of the isolated antibody comprises:
i. a heavy chain complementarity-determining region 1 (CDR-H1) comprising or consisting of the amino acid sequence of SEQ ID NO: 4;
ii. a heavy chain complementarity-determining region 2 (CDR-H2) comprising or consisting of the amino acid sequence of SEQ ID NO: 5; and
iii. a heavy chain complementarity-determining region 3 (CDR-H3) comprising or consisting of the amino acid sequence of SEQ ID NO: 6;

and the light chain variable (VL) region comprises a light chain variable (VL) region comprising:
i. a light chain complementarity-determining region 1 (CDR-L1) comprising or consisting of the amino acid sequence of SEQ ID NO: 10;
ii. a light chain complementarity-determining region 2 (CDR-L2) comprising or consisting of the amino acid sequence of YTS; and iii. a light chain complementarity-determining region 3 (CDR-L3) comprising or consisting of the amino acid sequence of SEQ ID NO: 12.

In one aspect is provided an isolated antibody, comprising:
i. a heavy chain variable (VH) region comprising or consisting of an amino acid sequence selected from the group consisting of SEQ ID NO: 13, SEQ ID NO: 14, SEQ ID NO: 15, SEQ ID NO: 16, SEQ ID NO: 17, and a variant of any one of SEQ ID NO:s 13 to 17, wherein any one amino acid has been altered for another amino acid, with the proviso that no more than 5 amino acids have been so altered, for example wherein 5, 4, 3, 2, or 1 amino acid has been so altered in each amino acid sequence, and ii. a light chain variable (VL) region comprising or consisting of an amino acid sequence selected from the group consisting of SEQ ID NO: 18, SEQ ID NO: 19, SEQ ID NO: 20, SEQ ID NO: 21, SEQ ID NO: 22, and a variant of any one of SEQ ID NO:s 18 to 22, wherein any one amino acid has been altered for another amino acid, with the proviso that no more than 5 amino acids have been so altered, for example wherein 5, 4, 3, 2, or 1 amino acid has been so altered in each amino acid sequence.

Thus, in some embodiments, the heavy chain variable (VH) region of the antibody comprises or consists of an amino acid sequence as defined by SEQ ID NO: 13. In some embodiments, the heavy chain variable (VH) region of the antibody comprises or consists of an amino acid sequence as defined by SEQ ID NO: 14. In some embodiments, the heavy chain variable (VH) region of the antibody comprises or consists of an amino acid sequence as defined by SEQ ID NO: 15. In some embodiments, the heavy chain variable (VH) region of the antibody comprises or consists of an amino acid sequence as defined by SEQ ID NO: 16. In some embodiments, the heavy chain variable (VH) region of the antibody comprises or consists of an amino acid sequence as defined by SEQ ID NO: 17. In some embodiments, the heavy chain variable (VH) region of the antibody comprises or consists of a variant of any one of the amino acid sequences as defined by SEQ ID NO:s 13 to 17, wherein any one amino acid has been altered for another amino acid, with the proviso that no more than 5 amino acids have been so altered, for example wherein 5, 4, 3, 2, or 1 amino acid has been so altered in each amino acid sequence.

In some embodiments, the light chain variable (VL) region of the antibody comprises or consists of an amino acid sequence as defined by SEQ ID NO: 18. In some embodiments, the light chain variable (VL) region of the antibody comprises or consists of an amino acid sequence as defined by SEQ ID NO: 19. In some embodiments, the light chain variable (VL) region of the antibody comprises or consists of an amino acid sequence as defined by SEQ ID NO: 20. In some embodiments, the light chain variable (VL) region of the antibody comprises or consists of an amino acid sequence as defined by SEQ ID NO: 21. In some embodiments, the light chain variable (VL) region of the antibody comprises or consists of an amino acid sequence as defined by SEQ ID NO: 22. In some embodiments, the light chain variable (VL) region of the antibody comprises or consists of a variant of any one of the amino acid sequences as defined by SEQ ID NO:s 18 to 22, wherein any one amino acid has been altered for another amino acid, with the proviso that no more than 5 amino acids have been so altered, for example wherein 5, 4, 3, 2, or 1 amino acid has been so altered in each amino acid sequence.

In some embodiments, the antibody is a bispecific antibody.

In some embodiments, the antibody is a full-length antibody. In some embodiments, the antibody is a Fab fragment. In some embodiments, the antibody is a F(ab') fragment. In some embodiments, the antibody is a F(ab')$_2$ fragment. In some embodiments, the antibody is a scFv. In some embodiments, the antibody is a diabody. In some embodiments, the antibody is a triabody.

In some embodiments, the antibody is a human IgG1 immunoglobulin subclass antibody. In some embodiments, the antibody is a human IgG2 immunoglobulin subclass antibody. In some embodiments, the antibody is a human IgG3 immunoglobulin subclass antibody.

The inventors have found that, compared to vehicle controls, S100A4-induced TNFα levels were not increased by mouse IgG1 or human IgG4 isotype controls, however 6B12 (mouse IgG1 anti-S100A4 antibody) significantly increased S100A4-induced TNFα levels, and this increase was absent in a humanized IgG4 anti-S100A4 antibody (for further details see Examples 4 and 7). For the present invention, it may be useful to use an antibody with an immunoglobulin subclass that elicits a weak or no pro-inflammatory response in the host. As shown, the human IgG4 subclass may in particular be useful when reduced effector or cross-linking functions of the antibody are desired. In some embodiments, the antibody is therefore a human IgG4 subclass antibody. In particular embodiments, the antibody is a human IgG4 subclass antibody with the HC sequence of SEQ ID NO: 58 and a LC sequence of SEQ ID NO: 59.

In some embodiments, the antibody comprises a human heavy chain constant (CH) region comprising or consisting of the sequence as set forth in SEQ ID NO: 56. In some embodiments, the antibody comprises a CH region comprising or consisting of a variant of SEQ ID NO: 56, said variant having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity thereto.

In some embodiments, the antibody comprises a human light chain constant (CL) region comprising or consisting of the sequence as set forth in SEQ ID NO: 57. In some embodiments, the antibody comprises a CL region comprising or consisting of a variant of SEQ ID NO: 57, said variant having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity thereto.

In some embodiments, the antibody comprises an Fc domain with a mutated human IgG constant region. In some embodiments, the antibody comprises a mutant human IgG4 heavy chain constant region. In some embodiments, said mutant human IgG4 heavy chain constant region comprises an S228P substitution, numbering according to EU numbering. Said S228P substitution may prevent in vivo and in vitro IgG4 Fab-arm exchange, which can result in functionally monovalent, bispecific antibodies (bsAbs) with unknown specificity and therefore, potentially, reduced therapeutic effect. In some embodiments, the terminal lysine of the human IgG4 heavy chain constant region has been removed.

The first humanized antibody was made in 1986 by Greg Winter's lab in Cambridge, UK. This antibody suffered a moderate loss of affinity but the strategy of CDR grafting murine CDR's onto human framework was considered a success. The next antibody to be humanized was the therapeutic antibody Campath-1 which suffered marked reduction in affinity and it was here that framework amino acids important for CDR stability and VH/VL interface stability first started to be explored.

Since the 1990's the humanization of murine antibodies has gained much interest as a means of making a tolerable therapeutic for human use. From its early days it was realized that framework amino acids play a key role in presenting the CDR's in a way favorable to their antigen binding, however no automatic or routine method of identifying and deciding which residues to back-mutate for successful increase of antigen affinity exist. It is important to consider which positions are important for stability of the VL/VH interface and the frequency of each amino acid at the given position in similar antibody frameworks. Framework back mutations may thus be useful for improving the affinity or stability of the humanized antibody to its target.

Thus, in some embodiments, the antibody comprises an amino acid substitution of the amino acid at position 40 of the VH region of any one of SEQ ID NO:s 13 to 17 to phenylalanine. In some embodiments, the antibody comprises an amino acid substitution of the amino acid at position 43 of the VH region of any one of SEQ ID NO:s 13 to 17 to serine. In some embodiments, the antibody comprises an amino acid substitution of the amino acid at position 44 of the VH region of any one of SEQ ID NO:s 13 to 17 to lysine.

In some embodiments, the antibody comprises an amino acid substitution of the amino acid at position 42 of the VL region of any one of SEQ ID NO:s 18 to 22 to glycine. In some embodiments, the antibody comprises an amino acid substitution of the amino acid at position 43 of the VL region of any one of SEQ ID NO:s 18 to 22 to threonine. In some embodiments, the antibody comprises an amino acid substitution of the amino acid at position 44 of the VL region of any one of SEQ ID NO:s 18 to 22 to leucine.

In some embodiments, the VH region of the antibody comprises or consists of a VH region as defined in SEQ ID NO: 24. In some embodiments, the VH region of the antibody comprises or consists of a VH region as defined in SEQ ID NO: 25. In some embodiments, the VH region of the antibody comprises or consists of a VH region as defined in SEQ ID NO: 26. In some embodiments, the VH region of the antibody comprises or consists of a VH region as defined in SEQ ID NO: 27. In some embodiments, the VH region of the antibody comprises or consists of a VH region as defined in SEQ ID NO: 28. In some embodiments, the VH region of the antibody comprises or consists of a VH region as defined in SEQ ID NO: 29. In some embodiments, the VH region of the antibody comprises or consists of a VH region as defined in SEQ ID NO: 30. In some embodiments, the VH region of the antibody comprises or consists of a VH region as defined in SEQ ID NO: 31. In some embodiments, the VH region of the antibody comprises or consists of a VH region as defined in SEQ ID NO: 32. In some embodiments, the VH region of the antibody comprises or consists of a VH region as defined in SEQ ID NO: 33. In some embodiments, the VH region of the antibody comprises or consists of a VH region as defined in SEQ ID NO: 34. In some embodiments, the VH region of the antibody comprises or consists of a VH region as defined in SEQ ID NO: 35. In some embodiments, the VH region of the antibody comprises or consists of a VH region as defined in SEQ ID NO: 36. In some embodiments, the VH region of the antibody comprises or consists of a VH region as defined in SEQ ID NO: 37. In some embodiments, the VH region of the antibody comprises or consists of a VH region as defined in SEQ ID NO: 38.

In some embodiments, the VL region of the antibody comprises or consists of a VL region as defined by SEQ ID NO: 39. In some embodiments, the VL region of the antibody comprises or consists of a VL region as defined by SEQ ID NO: 40. In some embodiments, the VL region of the antibody comprises or consists of a VL region as defined by SEQ ID NO: 41. In some embodiments, the VL region of the antibody comprises or consists of a VL region as defined by SEQ ID NO: 42. In some embodiments, the VL region of the antibody comprises or consists of a VL region as defined by SEQ ID NO: 43. In some embodiments, the VL region of the antibody comprises or consists of a VL region as defined by SEQ ID NO: 44. In some embodiments, the VL region of the antibody comprises or consists of a VL region as defined by SEQ ID NO: 45. In some embodiments, the VL region of the antibody comprises or consists of a VL region as defined by SEQ ID NO: 46. In some embodiments, the VL region of the antibody comprises or consists of a VL region as defined by SEQ ID NO: 47. In some embodiments, the VL region of the antibody comprises or consists of a VL region as defined by SEQ ID NO: 48. In some embodiments, the VL region of the antibody comprises or consists of a VL region as defined by SEQ ID NO: 49. In some embodiments, the VL region of the antibody comprises or consists of a VL region as defined by SEQ ID NO: 50. In some embodiments, the VL region of the antibody comprises or consists of a VL region as defined by SEQ ID NO: 51. In some embodiments, the VL region of the antibody comprises or consists of a VL region as defined by SEQ ID NO: 52. In some embodiments, the VL region of the antibody comprises or consists of a VL region as defined by SEQ ID NO: 53.

In some embodiments, the VH region of the antibody comprises or consists of SEQ ID NO: 24 (VH1_H40Phe) and the VL region of the antibody comprises or consists of SEQ ID NO: 47 (VL3_L44Leu). In some embodiments, the VH region of the antibody comprises or consists of SEQ ID NO: 24 (VH1_H40Phe) and the VL region of the antibody comprises or consists of SEQ ID NO: 20 (VL3). In some embodiments, the VH region of the antibody comprises or consists of SEQ ID NO: 26 (VH1_H44Lys) and the VL region of the antibody comprises or consists of SEQ ID NO: 20 (VL3). In some embodiments, the VH region of the antibody comprises or consists of SEQ ID NO: 13 (VH1) and the VL region of the antibody comprises or consists of SEQ ID NO: 47 (VL3_L44Leu). In some embodiments, the VH region of the antibody comprises or consists of SEQ ID NO: 13 (VH1) and the VL region of the antibody comprises or consists of SEQ ID NO: 20 (VL3).

In some embodiments, the antibody is PEGylated.

Antibody Function and Treatment Effects

In some embodiments, the antibody according to the present invention is capable of binding to native conformation S100A4 protein. In some embodiments, the antibody is capable of binding to dimeric forms of S100A4 protein. In some embodiments, the antibody is capable of binding to oligomeric forms of S100A4 protein. In some embodiments, the antibody is capable of binding to multimeric forms of S100A4 protein.

In some embodiments, the antibody is capable of binding to a polypeptide having at least 80% sequence identity to amino acids 1 to 101 as set out in SEQ ID NO: 23 (human S100A4). In some embodiments, the antibody is capable of binding to a polypeptide having at least 85% sequence identity to amino acids 1 to 101 as set out in SEQ ID NO: 23. In some embodiments, the antibody is capable of binding to a polypeptide having at least 90% sequence identity to amino acids 1 to 101 as set out in SEQ ID NO: 23. In some embodiments, the antibody is capable of binding to a polypeptide having at least 95% sequence identity to amino acids 1 to 101 as set out in SEQ ID NO: 23. In some embodiments, the antibody is capable of binding to human S100A4 polypeptide of SEQ ID NO: 23.

In some embodiments, the antibody is capable of neutralizing a biological activity of S100A4. In some embodiments, the biological activity of S100A4 is in promoting tumor progression and/or in inducing tumor metastasis.

In some embodiments, treatment with the anti-S100A4 antibody reduces fibrosis. Thus, in some embodiments, the antibody is capable of reducing S100A4-mediated fibrosis.

Fibrosis may be assessed by measuring dermal thickness, dermal hydroxyproline content, dermal $CD3^+$ cell count and/or dermal myofibroblast counts by methods known in the art. Thus, in some embodiments, treatment with the anti-S100A4 antibody reduces dermal thickness, dermal collagen or hydroxyproline content, dermal myoblast count and/or T-cell count.

In some embodiments, the antibody is capable of inhibiting the biological activity of S100A4 in promoting tumor progression and/or in inducing tumor metastasis and/or in inflammation.

In some embodiments, the antibody is capable of inhibiting T-cell recruitment mediated by S100A4. In some embodiments, the antibody is capable of inhibiting macrophage recruitment and/or infiltration mediated by S100A4.

In some embodiments, the antibody is capable of inhibiting the biological activity of S100A4 protein in stimulating cell invasion. In some embodiments, the biological activity of S100A4 protein in stimulating cell invasion is determined in a 3D Matrigel matrix assay or a T cell invasion assay where S100A4 stimulates T cell infiltration into a fibroblasts monolayer. In some embodiments, the biological activity of S100A4 in inducing tumor metastasis is determined in an in vivo mouse xenograft model.

In some embodiments, the antibody has low or no effector function. In some embodiments, the antibody induces low or no binding, cross-linking and/or activation of Fc receptor dependent effector functions of host cells.

Nucleic Acid and Expression Vector Encoding the Antibody

In one aspect is provided an isolated nucleic acid molecule encoding the antibody as described herein above in the section 'Isolated anti-S100A4 antibody molecule'. In some embodiments, the nucleic acid molecule is codon-optimized for the cell wherein it is expressed.

In one aspect is also provided an expression vector comprising the nucleic acid molecule as described herein encoding an anti-S100A4 antibody molecule. In some embodiments, the nucleic acid molecule of said expression vector is operably linked to control sequences to direct its expression. Such control sequences include regulatory elements that may control transcription of the sequence encoding the anti-S100A4 antibody molecule, e.g. promoters (such as those activated by transcription factors), enhancers or silencers. In some embodiments, translation of the mRNA encoding the encoding the anti-S100A4 antibody molecule may be controlled by a different control element, such as a riboswitch. Suitable control sequences and vectors are well known in the art.

Suitable techniques for producing and manipulating nucleic acids and expressing it in cells, such as mammalian cells, are well known in the art by the person of ordinary skill.

Host Cells Comprising the Antibody

In one aspect is provided an isolated host cell comprising the isolated nucleic acid molecule or the expression vector as described herein above in the section 'Nucleic acid and expression vector'.

In some embodiments, the isolated host cell is a human cell. In some embodiments, the isolated host cell is Chinese hamster ovary (CHO) cell.

The current invention may also be used in connection with ex vivo gene therapy, wherein patient cells are transfected or transduced in vitro with an expression vector coding for an antibody as disclosed herein. After transfection, the cells are infused back into the patient to express and secrete the antibody. Suitable donor cells for ex vivo gene therapy include T-cells.

Methods of Producing the Antibody as Described Herein

In one aspect is provided a method of producing an anti-S100A4 antibody molecule, the method comprising culturing the host cell as described herein above in the section 'Host cells comprising the antibody' under conditions wherein the antibody is expressed.

In some embodiments, the method further comprises purifying the antibody and isolating the anti-S100A4 antibody thus produced.

Pharmaceutical Compositions

In one aspect is provided a pharmaceutical composition comprising the antibody as described herein above in the section 'Isolated anti-S100A4 antibody molecule', the nucleic acid molecule and/or the expression vector as described herein above in the section 'Nucleic acid and expression vector encoding the antibody', and/or the host cell as described herein above in the section 'Host cells comprising the antibody', and a pharmaceutically acceptable diluent, carrier and/or excipient.

Method of Treatment

In one aspect is also provided a method of treatment of an individual with an S100A4-mediated condition, said method comprising administering the antibody as described herein above in the section 'Isolated anti-S100A4 antibody molecule', the nucleic acid molecule and/or the expression vector as described herein above in the section 'Nucleic acid and expression vector encoding the antibody', or the host cell as described herein above in the section 'Host cells comprising the antibody' to an individual in need thereof.

In some embodiments, the S100A4-mediated condition is a fibrotic condition.

In some embodiments, the fibrotic condition is systemic sclerosis. In some embodiments, the fibrotic condition is skin fibrosis. In some embodiments, the fibrotic condition is interstitial pulmonary fibrosis. In some embodiments, the fibrotic condition is liver fibrosis. In some embodiments, the fibrotic condition is kidney fibrosis.

It may be beneficial to combine treatment with anti-S100A4 antibody together with treatment with other compounds useful for the treatment of systemic sclerosis. Thus, in some embodiments, the antibody is co-administered with another compound for treatment of systemic sclerosis. In some embodiments, the antibody is co-administered with an angiotensin-converting enzyme inhibitor. In some embodiments, the antibody is co-administered with an angiotensin receptor blocker. In some embodiments, the antibody is co-administered with an azathioprine. In some embodiments, the antibody is co-administered with a calcium channel blocker. In some embodiments, the antibody is co-administered with a cyclophosphamide. In some embodiments, the antibody is co-administered with a hydroxychloroquine. In some embodiments, the antibody is co-administered with a mycophenolate. In some embodiments, the antibody is co-administered with a methotrexate. In some embodiments, the antibody is co-administered with a glucocorticoid. In some embodiments, the antibody is co-administered with a phosphodiesterase-5 inhibitor. In some embodiments, the antibody is co-administered with an endothelin receptor antagonist. In some embodiments, the antibody is co-administered with an alpha blocker. In some embodiments, the antibody is co-administered with a prostanoid. In some embodiments, the antibody is co-administered with rituximab. In some embodiments, the antibody is co-administered with a tyrosine kinase inhibitor such as nintedanib. In some embodiments, the antibody is co-administered with tociluzimab.

In some embodiments, the S100A4-mediated condition is an inflammatory condition. In some embodiments, the inflammatory condition is psoriasis. In some embodiments, the inflammatory condition rheumatoid arthritis. In some embodiments, the inflammatory condition is inflammatory myopathy.

In some embodiments, the S100A4-mediated condition is cancer. In some embodiments, the cancer is metastatic cancer.

In some embodiments, the cancer is gastric cancer. In some embodiments, the cancer is pancreatic cancer. In some embodiments, the cancer is colorectal cancer. In some embodiments, the cancer is thyroid cancer. In some embodiments, the cancer is breast cancer. In some embodiments, the cancer is squamous cell carcinoma. In some embodiments, the cancer is non-small cell lung cancer. In some embodiments, the cancer is prostate cancer. In some embodiments, the cancer is lung cancer. In some embodiments, the cancer is head and neck cancer. In some embodiments, the cancer is brain cancer (including glioblastoma multiforme). In some embodiments, the cancer is renal cell carcinoma (including clear cell renal carcinoma). In some embodiments, the cancer is melanoma. In some embodiments, the cancer is lymphoma. In some embodiments, the cancer is plasmocytoma. In some embodiments, the cancer is sarcoma. In some embodiments, the cancer is glioma. In some embodiments, the cancer is thymoma. In some embodiments, the cancer is leukemia. In some embodiments, the cancer is colon cancer. In some embodiments, the cancer is esophageal cancer. In some embodiments, the cancer is ovary cancer. In some embodiments, the cancer is cervical cancer. In some embodiments, the cancer is hepatoma.

In some embodiments, the antibody, nucleic acid molecule, expression vector, and/or host cell is administered via parenteral administration. Thus in some embodiments, the antibody, nucleic acid molecule, expression vector, and/or host cell is administered subcutaneously. In some embodiments, the antibody, nucleic acid molecule, expression vector, and/or host cell is administered intramuscularly. In some embodiments, the antibody, nucleic acid molecule, expression vector, and/or host cell is administered intravenously.

In some embodiments, the antibody, nucleic acid molecule, expression vector, and/or host cell is administered once every week or less. In some embodiments, the antibody is administered weekly, with a weekly dosage of in the range of 15 mg to 1000 mg.

Method of Diagnosis or Prognosis

In one aspect is provided a method for diagnosis or prognosis of an S100A4-related condition in an individual, the method comprising
(a) contacting a biological sample from the individual with an anti-S100A4 antibody as described herein, which is capable of binding to S100A4 polypeptide present in the sample; and
(b) determining the presence and/or amount of the complex formed between the antibody molecule and the S100A4 polypeptide.

In some embodiments, the biological sample is blood. In some embodiments, the biological sample is plasma. In some embodiments, the biological sample is serum. In some embodiments, the biological sample is a tissue sample. In some embodiments, the biological sample is interstitial tissue fluids. In some embodiments, the biological sample is saliva. In some embodiments, the biological sample is cerebrospinal fluid. In some embodiments, the biological sample is synovia.

EXAMPLES

Example 1—Humanization of the Mouse Anti-S100A4 Antibody

Humanization was performed on the mouse monoclonal IgG1 anti-S100A4 antibody 6B12 (VH regions and VL regions as defined in SEQ ID NO: 54 and SEQ ID NO: 55, respectively).

Sequence Analysis and Humanized Variant Alignments

Using antibody numbering systems from IMGT and Kabat, the CDRs of the VH and VL region of 6B12 were identified. These two numbering systems identify different residues of the murine antibody as belonging to the CDR, and a combined IMGT/Kabat CDR sequence were used for optimal retention of CDR-loop conformation.

The closest human germline gene V-region to the VH region was identified as *Homo sapiens* IGHV4-34*09. Databases of Human IgG sequences were searched for comparison to the murine VH domain using BLAST search algorithms, and candidate human variable domains selected from the top 200 BLAST results. These were reduced to four candidates for each based on a combination of framework homology, maintaining key framework residues and canonical loop structure. For the fifth acceptor sequence, the closest human germline IGHV4-34*09 was selected.

The closest human germline gene V-region to the VL region was identified as the *Homo sapiens* IGKV1-27. Databases of Human IgK sequences were likewise searched for comparison to the murine VL domain using BLAST search algorithms, and candidate human variable domains selected from the top 200 BLAST results. These were reduced to four candidates based on a combination of framework homology, maintaining key framework residues and canonical loop structure. For the 5th acceptor sequence, the closest human germline IGKV1-27 was selected.

The CDRs of the murine VH and VL were then grafted into these acceptor frameworks to yield the 5 humanized VH variants VH1-VH5 (SEQ ID NO:s 13-17) and the 5 humanized VL variants VL1-VL5 (SEQ ID NO:S 18-22).

Humanization Check

The humanized variants were checked to determine whether they had been humanized in accordance with WHO's definition of humanized antibodies: The variable domain of a humanized chain has a V region amino acid sequence which, analysed as a whole, is closer to human than to other species (assessed using the Immunogenetics Information System® (IMGT®) DomainGapAlign tool).

All variants were categorized as humanized in accordance with WHO's definition of humanized antibodies.
Framework Back Mutations of the Heavy and Light Chains The VL and VH regions were analysed for good candidates for framework back mutations in order to improve the affinity of the humanized antibody to its target.

This was done by examining the frequency of amino acids at each position in murine antibodies, specifically looking for amino acids with a very low frequency, such as 1% or lower. These amino acids were further evaluated whether they might be in a structurally important position, and these were considered potential candidates for a framework back mutation.

For the VL region, L44 (L) was identified as being unusual in this position (frequency of less than 1%). This position has been shown to be important in the VL/VH interface. In the likely parental germline this position is a valine. Most frequently this position is a proline. This was considered a good candidate for back mutation. The previous amino, L43 (T) was also considered worth keeping as a framework back mutation, although it was noted that one of the 5 humanized sequences also had this sequence. In the closest human germline sequences this was identified as an alanine or valine. Likewise L42 (G) was also considered a good position for a framework back mutation.

For the VH region, the amino acid at H43 (S) was considered a good candidate for framework back mutation, as it is an important residue in the VH/VL interface, and since this position typically is lysine, glutamine or arginine. Likewise, H40 (F) and H44 (K) were also considered good positions for framework back mutations as they had a frequency of 1%. Although they were not considered strictly at a key defined position, they are immediately adjacent and thus considered good candidates.

The results of the framework back mutations in regards to the affinity for S100A4 of the humanized antibodies are further described in Example 2.

Example 2—Kinetic Analysis of Anti-S100A4 Antibody Interaction with S100A4

Quantitative, kinetic analysis of the interactions between 14 humanized antibodies and 2 control antibodies with the human S100A4 dimer were performed using surface plasmon resonance (SPR).

Materials and Methods

The analysis was performed using a Biacore T200 instrument, at 25° C. analysis temperature, at a flow rate of 50 µl/min for quantitative kinetic interaction analyses.

Analysis buffer: 10 mM HEPES pH 7.4, 300 mM NaCl, 1 mM $CaCl_2$), 100 µM EDTA, 0.05% Tween 20

Assay Cycles:
1. Preparation of an anti-His capture surface
2. Reversible capturing of antigen (S100A4)
3. Quantitative analysis of antibodies in MCK mode (0.78-200 nM)
4. Complete removal of antibody-antigen complex from capture surfaces CM4 Sensor Chip #2:
fc1: 6878 RU reference
fc2: 6515 RU capture antigen (S100A4)
fc3: 6804 RU
fc4: 6540 RU 14 humanized antibodies were analysed in this experiment, some of which had specific amino acids in their VL and/or VH framework regions back-mutated. Each antibody comprised one the following heavy chain variable regions (VH):
  VH0 (SEQ ID NO: 54)
  VH1 (SEQ ID NO: 13)
  VH1_H40Phe (SEQ ID NO: 24)
  VH1_H43Ser (SEQ ID NO: 25)
  VH1_H44Lys (SEQ ID NO: 26)

Each antibody also comprised one the following light chain variable regions (VL):
  VL0: (SEQ ID NO: 55)
  VL3 (SEQ ID NO: 20)
  VL3_L42Gly (SEQ ID NO: 45)
  VL3_L43Thr (SEQ ID NO: 46)
  VL3_L44Leu (SEQ ID NO: 47)
  VL3_L42Gly+L44Leu 2 control antibodies were also analysed:
  6B12: Mouse monoclonal IgG1 anti-S100A4 as described in Example 1
  VH0 VL0: The VH and VL regions of 6B12 comprised in a humanized gG4 isotype framework.

Results and Conclusion

The results of the analysis can be seen in Table 1, below.

TABLE 1

Summary of kinetic data

| Sample | Kinetic fit 1:1 binding | | | | % of |
|---|---|---|---|---|---|
| | $k_a$ (M$^{-1}$s$^{-1}$) | $k_d$ (s$^{-1}$) | $K_d$ (M) | Rmax (RU) | Rmax theor. |
| 6B12 | 1.24 E+05 | 2.06 E−04 | 1.65 E−09 | 23.3 | 75.6 |
| VH0 VL0 | 2.29 E+05 | 2.19 E−04 | 9.58 E−10 | 26.9 | 92.9 |
| VH1_H40Phe VL3 | 2.17 E+05 | 5.76 E−04 | 2.65 E−09 | 25.8 | 83.0 |
| VH1 VL3_L44Leu | 2.39 E+05 | 5.37 E−04 | 2.25 E−09 | 26.8 | 85.9 |
| VH1 VL3_L42Gly + L44Leu | 2.63 E+05 | 5.23 E−04 | 1.99 E−09 | 27.6 | 89.4 |
| VH1 VL3 | 1.94 E+05 | 6.74 E−04 | 3.47 E−09 | 24.4 | 85.1 |
| VH0 VL3 | 1.91 E+05 | 2.79 E−04 | 1.46 E−09 | 25.7 | 90.6 |
| VH1_H43Ser VL3 | 2.11 E+05 | 6.79 E−04 | 3.21 E−09 | 24.9 | 88.0 |
| VH1_H44Lys VL3 | 2.13 E+05 | 5.92 E−04 | 2.77 E−09 | 27.6 | 91.7 |
| VH1 VL3_L42Gly | 2.13 E+05 | 6.40 E−04 | 3.00 E−09 | 27.6 | 91.3 |
| VH1 VL3_L43Thr | 1.87 E+05 | 8.82 E−04 | 4.72 E−09 | 26.3 | 86.4 |
| VH1_H40Phe + H44Lys VL3 | 2.31 E+05 | 5.60 E−04 | 2.43 E−09 | 28.3 | 93.6 |
| VH1_H43Ser + H44Lys VL3 | 2.10 E+05 | 5.96 E−04 | 2.84 E−09 | 27.2 | 97.2 |
| VH1_H43Ser VL3_L44Leu | 2.15 E+05 | 5.12 E−04 | 2.38 E−09 | 28.0 | 99.0 |
| VH1_H43Ser + H44Lys VL3_L44Leu | 2.36 E+05 | 5.07 E−04 | 2.15 E−09 | 28.2 | 101.8 |
| VH1 VL0 | 3.13 E+05 | 3.61 E−04 | 1.15 E−09 | 26.6 | 96.2 |

The 14 tested antibodies all had similar dissociation constants to the 6B12 antibody, showing high binding affinities to S100A4. However, it was clear that some of the specific framework back-mutations in the humanized light or heavy chains had an improved effect on the dissociation constant. For example, VH1 VL3 showed a $K_d$ of 3.47 E-09, while this was improved to 2.25 E-09 for VH1 VL3_L44Leu and to 1.99 E-09 for VH1 VL3_L42Gly+L44Leu. Some of these manually designed framework back mutations thus successfully increased the affinities of the antibody to S100A4. However, it is important to note that not all framework back mutations increased antibody affinity for S100A4, e.g. VH1 VL3_L43Thr showed a $K_d$ of only 4.72 E-09.

Example 3—Humanized Anti-S100A4 Antibody Efficacy in Treating Bleomycin-Induced Dermal Fibrosis In Vivo Systemic sclerosis (SSc) is a systemic fibrosing orphan disease with high morbidity and mortality. SSc is the condition with the highest case specific mortality of any of the autoimmune rheumatic diseases with more than half of cases diagnosed with the condition eventually dying as a direct consequence. The hallmark of the disease is accumulation of extracellular matrix proteins by pathologically activated fibroblasts. Therapeutic approaches to selectively inhibit the aberrant release of extracellular matrix in SSc are not available to date. Bleomycin-induced dermal fibrosis is the most commonly used mouse model of SSc. It resembles in particular early, inflammatory stages of SSc. Here, we aimed to evaluate the effects of humanized S100A4-antibodies in bleomycin-induced skin fibrosis.

Materials and Methods

Antibody Stock Solution

AX-202, a humanized IgG4 mono-clonal anti-S100A4 antibody, was used for this study. The antibody comprises a heavy chain sequence as defined in SEQ ID NO: 58 and a light chain sequence as defined in SEQ ID NO: 59. The antibody was dissolved in PBS and stored at −20° C.

Study Animals

The experiments were performed on C57Bl/6 mice.
  Number of animals: 64
  Early mortalities: none
  Overall duration of study of each animal: 6 weeks Treatment Protocol 2 mg/mL antibody stock solution was diluted in sterile PBS and injected i.p. in a volume of 100 μL.

Skin fibrosis was induced by daily subcutaneous injections of bleomycin (2.5 mg/kg, Sigma-Aldrich) in defined and marked areas of the upper back (1 cm$^2$) for up to six weeks. Treatment was commenced after three weeks of pre-challenge with bleomycin, with injections twice weekly intraperitoneally (i.p.) or once every week with intravenous (IV) injection in the tail vein. The outcome was analysed three weeks after the first injection of bleomycin (six weeks after the first bleomycin-injection).

Study Design and Study Groups

N=8 mice in control groups, N=10 mice in treatment groups with the humanized antibody The following experimental groups were used:
  Group 1: Control/NaCl
  Group 2: bleomycin 3 weeks and NaCl 3 weeks
  Group 3: bleomycin 6 weeks+NaCL for last 3 weeks (every 3rd day IP)
  Group 4: bleomycin 6 weeks+AX-202 16 mg/kg for the last 3 weeks (twice a week IP)
  Group 5: bleomycin 6 weeks+AX-202 24 mg/kg for the last 3 weeks (weekly IV tail vein injection)
  Group 6: bleomycin 6 weeks+AX-202 8 mg/kg for the last 3 weeks (twice a week IP)

Study Conduct

The mice were monitored clinically on a daily basis for behavior, activity, texture of the fur and consistency of the stool. After sacrifice, a gross macroscopic evaluation of the lungs and the skin was performed.

Quantification of Hypodermal Thickening

After sacrifice by cervical dislocation, skin samples of 1 cm2 were obtained from a defined area of on the upper back between the shoulder blades. Lesional skin areas were excised, fixed in 4% formalin for 6 h and embedded in paraffin. Five m sections were cut and stained with hematoxylin and eosin. The dermal thickness was measured at 100-fold magnification by measuring the distance between the epidermal-dermal junction and the dermal-subcutaneous fat junction at three sites from lesional skin of each mouse.

Detection of Myofibroblasts

Myofibroblasts are characterized by the expression of α-smooth muscle actin (αSMA). Fibroblasts positive for αSMA were detected in paraffin-embedded slides from the upper back by incubation with monoclonal anti-αSMA antibodies (clone 1A4, Sigma-Aldrich, Steinheim, Germany). The expression was visualized with horseradish peroxidase-labelled secondary antibodies and 3,3-diaminobenzidine tetrahydrochloride (DAB) (Sigma-Aldrich). Monoclonal mouse IgG antibodies (Calbiochem, San Diego, CA, USA) were used for controls. The analysis was performed by a blinded reviewer evaluating the myofibroblasts in four sections per sample.

Hydroxyproline Assay

The amount of collagen protein in skin samples was determined via hydroxyproline assay. After digestion of full skin thickness punch biopsies (0=3 mm) derived from the upper back in 6 M HCl for three hours at 120° C., the pH of the samples was adjusted to 6 with 6 M NaOH. Afterwards, 0.06 M chloramine T was added to each sample and incubated for 20 min at room temperature. Next, 3.15 M perchloric acid and 20% p-dimethylaminobenzaldehyde were added and samples were incubated for an additional 20 min at 60° C. The absorbance was determined at 557 nm with a Spectra MAX 190 microplate spectrophotometer.

Statistics

All data are presented as mean±SEM, and differences between the groups were tested for their statistical significance by one way ANOVA testing using graph pad 8. P-values less than 0.05 were considered significant. P-values are expressed as follows: $0.05 > p > 0.01$ as *; $0.01 > p > 0.001$ as ; $p < 0.001$ as * as compared to control mice injected with NaCl for 6 weeks. $0.05 > p > 0.01$ as #; $0.01 > p > 0.001$ as ##; $p < 0.001$ as ### as compared to mice injected with bleomycin for 3 weeks followed by injections of NaCl for another 3 weeks.

Results

Dermal Fibrosis Mouse Model

Mice developed prominent dermal fibrosis upon challenge with bleomycin with more pronounced fibrotic changes in mice challenged with bleomycin for 6 weeks as compared to mice challenged with bleomycin for 3 weeks followed by injections of the solvent of bleomycin, NaCl, for another 3 weeks. Mice injected with NaCl for 6 weeks served as controls.

General Tolerability

Treatment with the anti-S100A4 antibody AX-202 was well tolerated without obvious signs of toxicity on clinical examination, on gross necropsy or on histology.

Efficacy Results

Treatment with AX-202 significantly reduced dermal thickening, myofibroblast counts and the hydroxyproline content as compared to control mice injected with bleomycin for 6 weeks (see FIGS. 1A-1E). The effects were dose-dependent with most pronounced effects observed in doses of 16 mg/kg IP and 24 mg/kg once weekly IV (see FIGS. 1A-1C). However, statistically significant effects of AX-202 were also observed with 8 mg/kg IP every third day. In doses of 16 mg/kg IP and 24 mg/kg IV, AX-202 also induced regression of fibrosis with statistically significant changes of dermal thickness and myofibroblast counts as compared to mice injected with bleomycin only for three weeks.

Conclusion

Treatment with AX-202 strongly ameliorated bleomycin-induced skin fibrosis dermal thickening, myofibroblast counts and hydroxyproline in well-tolerated doses.

Example 4—Impact on S100A4-Induced Cytokine Release In Vitro

Materials and Methods

Peripheral blood mononuclear cells (PBMCs) were isolated from healthy donors through FicollPaque PLUS (GE Healthcare; 11778538) density centrifugation and monocytes isolated using a monocyte isolation kit (StemCell Technologies; 19359).

Monocytes were plated (100,000 cells/well) into 96 well plates and cultured for 6 hours in the presence of:
media,
vehicle 1 (0.074% TBS),
LPS (1.0 ng/ml; Invivogen; tlrl-b5lps),
S100A4 (2.0 μg/ml),
S100A4 (2.0 μg/ml)+vehicle 2 (3.2% PBS),
vehicle 1+mouse IgG1 (Biolegend; 401407),
vehicle 1+human IgG4 (Biolegend; 403701),
vehicle 1+AX-202 or 6B12 (each at 32 g/ml),
S100A4 (2.0 μg/ml)+mouse IgG1 (at either 8.0, 16 or 32 μg/ml),
S100A4 (2.0 μg/ml)+human IgG4 (at either 8.0, 16 or 32 μg/ml),
S100A4 (2.0 μg/ml)+AX-202 (at either 8.0, 16 or 32 μg/ml), or
S100A4 (2.0 μg/ml)+6B12 (at either 8.0, 16 or 32 μg/ml).

6B12: mouse monoclonal IgG1 anti-S100A4 antibody as described in Example 1

AX-202: humanized monoclonal IgG4 anti-S100A4 antibody as described in Example 3

After 6 hours of culture, cell culture supernatant was collected and stored at −20° C. for subsequent cytokine analysis. Levels of cytokines (IL-6, TNF-α and IL-10) in the supernatant were quantified by Luminex assay according to manufacturer's instructions (R&D systems; LXSAHM-03).

Results

Compared to vehicle control, stimulation of monocytes with either LPS (1.0 ng/ml; positive control) or S100A4 (2.0 μg/ml) evoked an increase in the levels of IL-6, TNFα and IL-10 measured in the cell culture supernatant (see FIGS. 2A-2D and 3A-3D). Compared to isotype controls, at all concentrations tested, AX-202 or 6B12 reduced the S100A4-evoked increase in IL-6 and IL-10 (see FIGS. 2C-2D and 3C-3D). Compared to vehicle controls, S100A4-induced TNFα levels were not increased by mouse IgG1 or human IgG4 isotype controls (see FIGS. 4A-4B), however 6B12, and not AX-202, significantly increased S100A4-induced TNFα levels, and the increase induced by 6B12 showed a dose-dependent trend (see FIGS. 4C-4D).

Conclusion

As expected, S100A4 evoked an increase in the levels of IL-6, TNFα and IL-10 (see FIGS. 2A-2D, 3A-3D, and 4A-4D). S100A4-evoked IL-6 and IL-10 release was reduced by both AX-202 and 6B12 (see FIGS. 2C-2D and 3C-3D).

Figure 4A:
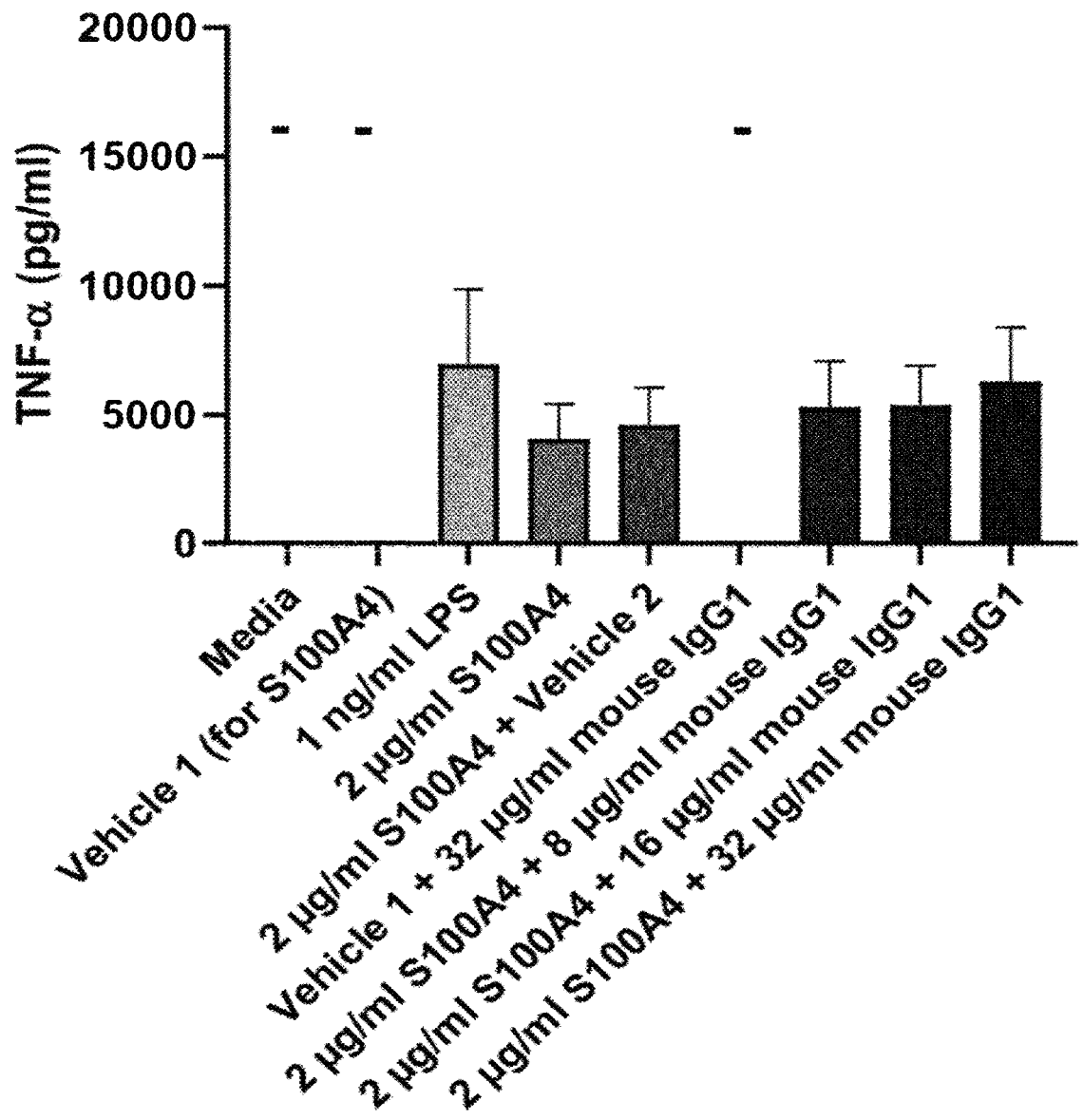
Figure 4B:
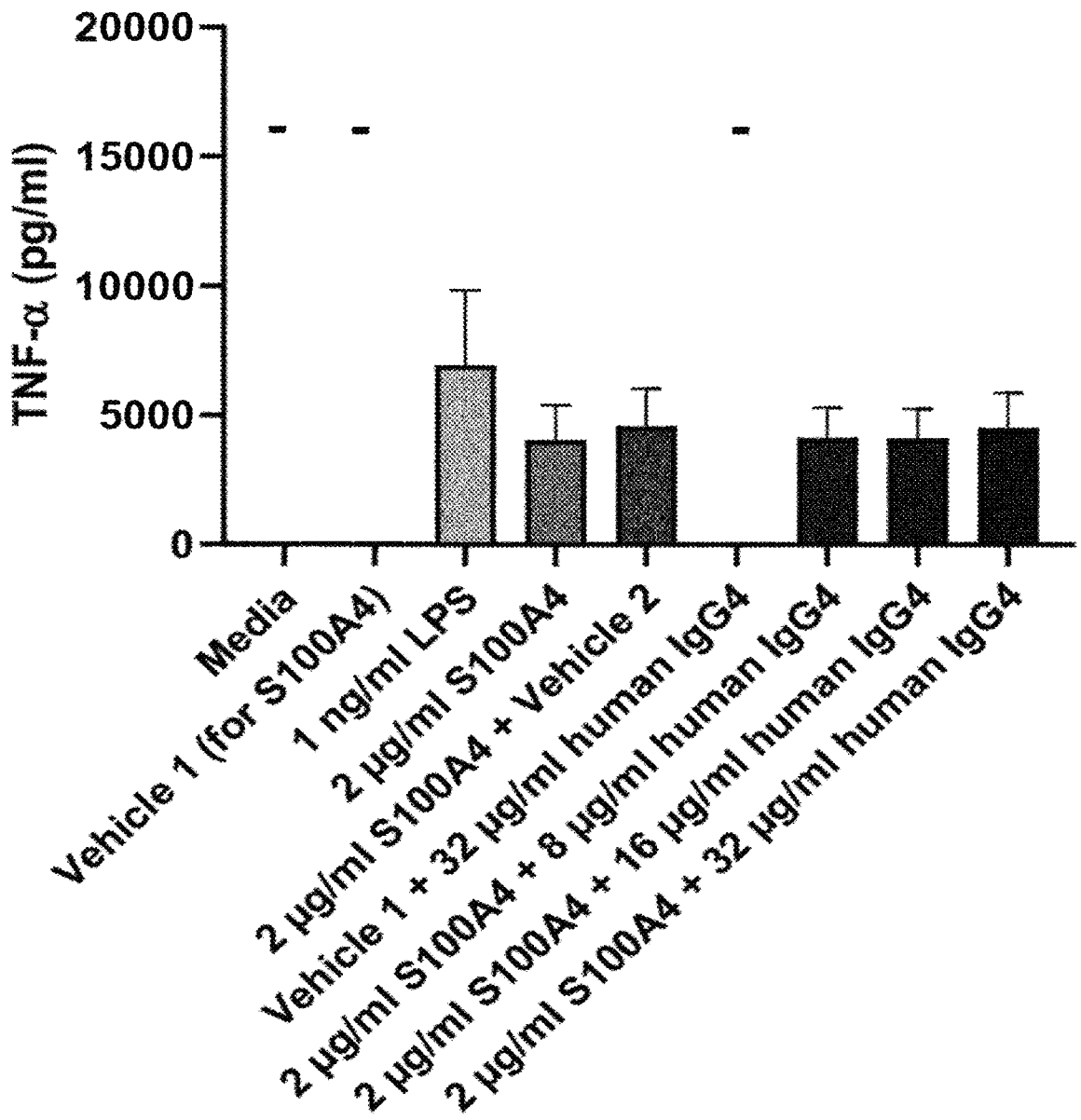
Figure 4C:
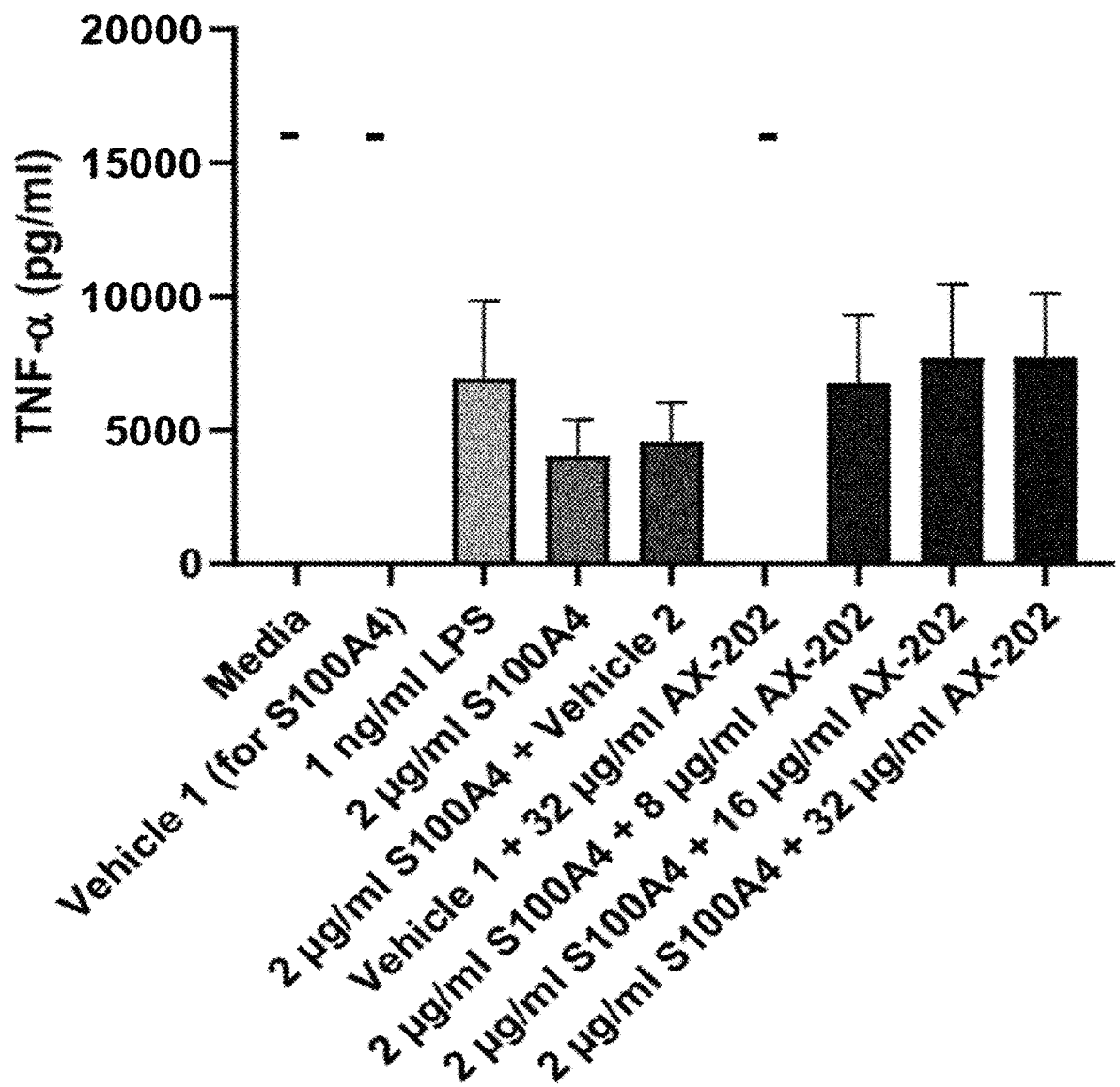
Figure 4D:
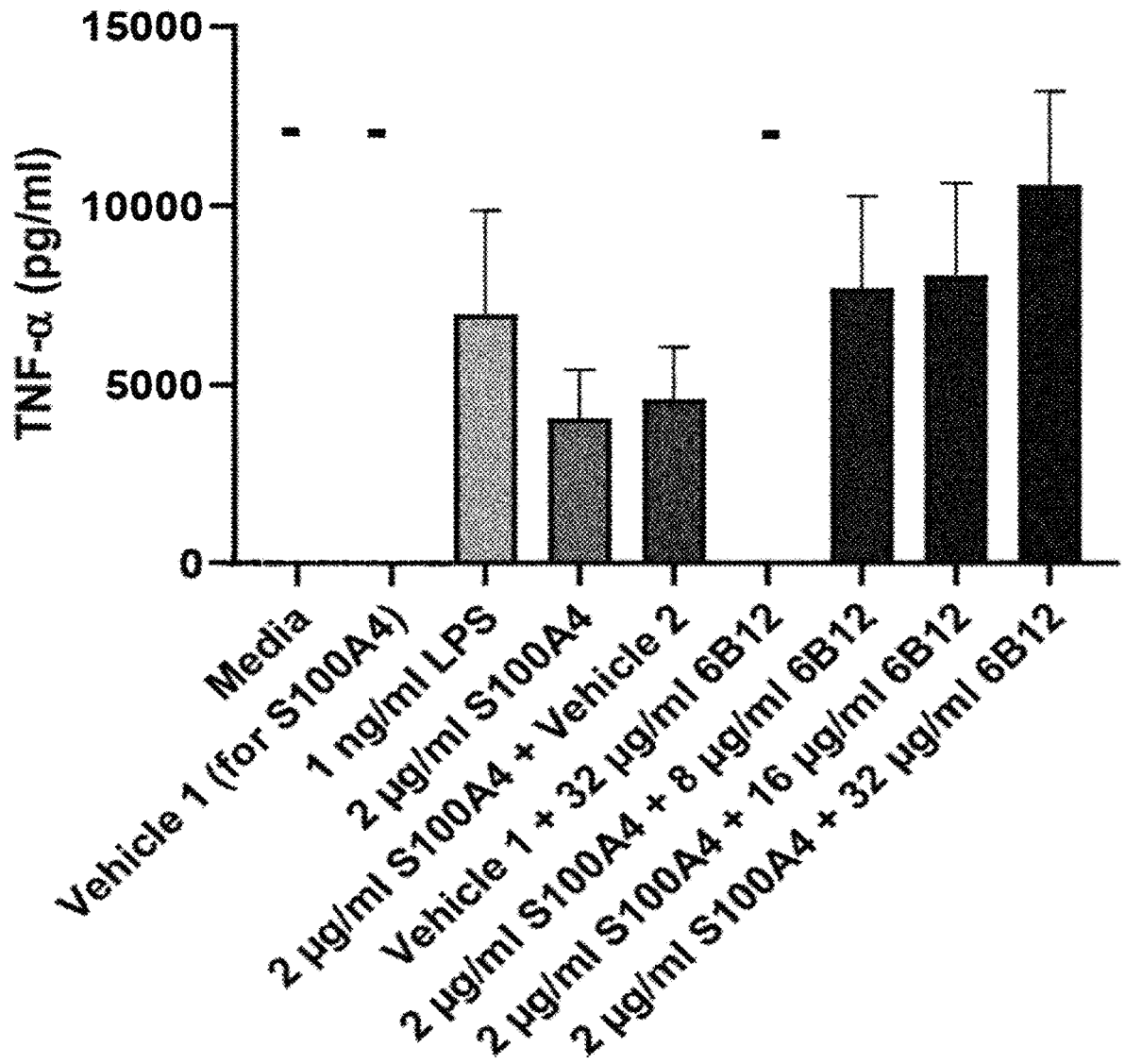

Importantly, mouse IgG1 control, human IgG4 control, or AX-202 in combination with S100A4 did not result in significant increases in TNFα levels compared to S100A4 alone (see FIGS. 4A-4B). In contrast, the levels of S100A4-induced pro-inflammatory cytokine TNFα were increased by treatment with the 6B12 antibody in a dose-dependent fashion (see FIGS. 4C and 4D).

This indicates that, surprisingly, the humanized anti-S100A4 IgG4 antibody does not increase S100A4-induced pro-inflammatory TNFα levels compared to the mouse anti-S100A4 antibody 6B12.

Although the foregoing invention has been described in some detail by way of illustration and example for purposes of clarity of understanding, the descriptions and examples should not be construed as limiting the scope of the invention.

The foregoing written specification is considered to be sufficient to enable one skilled in the art to practice the disclosure. It will be appreciated, however, that no matter how detailed the foregoing may appear in text, the disclosure may be practiced in many ways and the disclosure should be construed in accordance with the appended claims and any equivalents thereof.

Example 5—Humanized Anti-S100A4 Antibodies Show No Cross-Reactivity to Other S100-Family Members and are Specific to S100A4 from Multiple Species The ability of different humanized variants (VH1_40Phe:VL3, VH1:VL3_Leu44, and VH1_40Phe:VL3_Leu44) to selectively react to S100A4 was tested by Western blot. All variants detected mouse and human S100A4 protein and did not cross-react with other S100 family members (see FIG. 5).

To confirm the specificity of the same human variants to recognize S100A4 protein, and to exclude that the variants do not cross react with random cellular proteins, fluorescence microscopy experiments were performed using wild-type (wt) and S100A4 knock-out (ko) mouse embryonic fibroblasts (MEFs). The IF staining indicates that all three humanized variants of 6B12 (Phe40, Leu44, and Phe40/Leu44) did not cross-react to proteins of ko-fibroblasts, while the wt MEFs show the typical perinuclear cytoplasmic staining of S100A4 (see FIG. 6).

This result is an agreement with earlier results showing that 6B12 only recognizes S100A4 (Klingelhafer et al., 2012). Furthermore, no cross-reactivity was observed to S100A2, which shares the highest homology with the epitope sequence, and S100A5, which shows the highest overall homology of all S100 family members.

AX-202, as described in Example 3, was additionally shown to bind with similar affinity to S100A4 across 4 different species (monkey, rat, human and mouse).

Example 6—Humanized Anti-S100A4 Antibody Reduces S100A4-Induced Inflammatory Pathway Activation HEK-Blue hTLR4 (InvivoGen, #hkb-htlr4) cells were incubated in HEK-Blue Detection medium (InvivoGen, #hb-det2) and stimulated with increasing concentration of recombinant human S100A4 multimer or 1.25 ng/ml LPS-EK ultrapure (positive control; InvivoGen, #tlrl-peklps). After 20 h incubation, the levels of NF-kB induced secreted embryonic alkaline phosphatase (SEAP) were determined by reading the OD at 620 nm. S100A4 was shown to clearly activate the NF-kB reporter gene in HEKBlue hTLR4 cells in a concentration-dependent manner (see FIG. 7A).

HEK-Blue hTLR4 and HEK-Blue Null2 (control, InvivoGen, #hkb-null2) cells were incubated in HEK-Blue Detection medium and stimulated either with 1.25 ng/ml LPS-EK ultrapure (InvivoGen, #tlrl-peklps), 1.25 or 2.5 µg/ml S100A4. Cells treated with 50 ng/ml TNF-α (InvivoGen, #rcyc-htnfa) were used as a positive control for HEK-Blue Null2 cells activation. S100A4 activation of the NF-kB reporter gene was shown to be dependent on the TLR4, as activation of the reporter gene was completely abrogated in Null2 cells even with addition of S100A4 (see FIG. 7B).

HEK-Blue hTLR4 cells were incubated in HEK-Blue Detection medium and stimulated with 1.25 µg/ml S100A4 alone and increasing concentrations of the S100A4-neutralizing antibody AX-202 (described in Example 3). LPS activation of the reporter gene was not affected by AX-202, however AX-202 was shown to inhibit S100A4-induced TLR4 activation in a concentration-dependent manner (see FIG. 7C).

Example 7—Change in FcR-Mediated Effector Function by IgG Subclass Switch of Humanized Antibody We were particularly interested in whether the subclass switch could affect FcγRIIa activation, which could impact the therapeutic efficacy. FcγRIIa is an activating FcγR with a low affinity for single 'monomeric' IgG molecules but high avidity for IgG-containing ICs (Arman et al., 2015).

In leukocytes, FcγRIIA engagement initiates strong effector functions that are key for immune and inflammatory responses, including cytokine release and ADCC (antibody-dependent cellular cytotoxicity), which could negatively influence the safety profile of the antibody-drug. Moreover, on human platelet, the FcγRIIa plays a role in heparin-induced thrombocytopenia, a well-documented prothrombotic adverse drug effect (Sun et al., 2013).

This study aims to investigate whether the subclass shift from mouse IgG1 of the parental 6B12 antibody to human IgG4 of AX-202 affects binding affinity towards the FcγRIIa. A lower FcγRIIA binding affinity of antibody-immune complexes could indicate a better safety profile.

Materials and Methods

FcYRIIA Reporter Assay 3-fold of the final antigen (S100A4) concentration and 3-fold of the final concentration of the antibody were prepared in assay buffer and 25 µl of each were added to appropriate wells in a 96-well plate and incubated at 37° C. for 15-25 minutes. An appropriate number of cells were thawed and transferred to assay buffer. 50 000 cells were seeded per well in 25 µl assay buffer to have a final volume of 75 µl/well. The plate was covered with a lid and incubated at 37° C. and 5% $CO_2$ for 18 hours. After incubation, the assay plate was removed from the incubator and equilibrated to ambient temperature (22-25° C.) for 15 minutes. 50 µl of Bio-Glo™ Reagent was added to each of the assay plates followed by incubation at room temperature for 15 minutes. Luminescence was measured using luminescence plate reader (see protocol section 10.01).

Analysis of Results

The data points were imported into Prism Graph Pad (Version is 9.1.0) and analyzed using unpaired t-test (two-tailed). Asterisks demonstrate significant relevance when $P<0.05$ based on n=3.

Biological Activity

All assays were performed with negative and positive control cells for comparison of receptor activation. All positive and negative controls showed the expected results.

Results

Changes of FcR-Mediated Effector Function by IgG Subclass Switch

Previously obtained results have shown that the murine IgG1 6B12 and the AX-202 with its human IgG4 scaffold could inhibit S100A4-induced cytokine release of monocytes. Stimulation of monocytes with S100A4 induced the levels of IL-6, TNFα, and IL-10 in cell culture supernatants. Both AX-202 and 6B12 blocked the S100A4 stimulated increase of IL-6 and IL-10, however, elicited a counterintuitive increase in TNFα. This may suggest that the immune complex constituted of oligomeric S100A4 and antibody (6B12) is triggering TNFα release via FcγRs.

Thus, the choice of the IgG subclass could have a major impact on unwanted cytokine release. To test this possibility, we performed a FcγRIIA reporter assay and assessed how strongly the different antibodies induce FcγR-dependent promotor activity.

IgG-Class Switch from Human IgG1 to IgG4 Substantially Reduces Antigen-Specific FcγRIIa Activation The FcγRIIa-H ADCP Reporter Bioassay from Promega was employed to measure the antibody subtype difference in potency of Ab-Ag complexes to activate FcγRIIa. The assay consists of human Jurkat cells stably expressing human FcγRIIa-H (the high-affinity H131 variant) and NFAT-induced luciferase. This study included two different AX-202 antibodies carrying either hIgG from class 1 or 4. In addition, the parental mouse antibody, 6B12 IgG1, was included in the study. The results are depicted in FIG. 8. The immune complexes (ICs) were formed by mixing antibodies with either dimeric (FIG. 8, panel A) or multimer S100A4 protein (FIG. 8, panel B).

The receptor clustering is significantly higher for AX-202 hIgG1 compared to AX-202 hIgG4 with a receptor activation fold difference of 5.00 and 3.83 for S100A4-D and S100A4-M, respectively (see FIG. 8). 6B12, which has a mouse IgG1 scaffold, has lower potency to induce IC-dependent FcγRIIa than its human counterpart (AX-202 hIgG1). However, 6B12 showed still 3.23 (Dimer) and 2.87-fold (Multimer) higher activation than AX-202 hIgG4. Neither IgG1 nor IgG4 control antibodies mediate receptor clustering indicating that Ab-Ag IC formation is important for FcγRIIa clustering and activation.

Conclusion

Antibodies have recently been found to mediate inflammation and immune modulation by inducing cellular differentiation, activation, and cytokine release (A van Erp et al., 2019). This could lead to unwanted proinflammatory pathway activation and counteract the mode-of-action of the therapeutic S100A4 antibody. Here we found that an S100A4 neutralizing antibody with an IgG4 scaffold had a much better safety profile than the same antibody with a human IgG1 scaffold, with an approximately 3-fold lower potency to induce FcγR activation.

SEQUENCE OVERVIEW

| SEQ ID NO: | Description | Organism | Sequence |
|---|---|---|---|
| 1 | CDR-H1 (amino acid sequence-identified using the Kabat numbering system) | Artificial sequence | NDYYWN |
| 2 | CDR-H2 (amino acid sequence-identified using the Kabat numbering system) | Artificial sequence | HIGYGGNINYNPSLKN |
| 3 | CDR-H3 (amino acid sequence-identified using the Kabat numbering system) | Artificial sequence | ESFYDGYPFDY |
| 4 | CDR-H1 (amino acid sequence-identified using the IMGT numbering system) | Artificial sequence | GDSFTNDYY |
| 5 | CDR-H2 (amino acid sequence-identified using the IMGT numbering system) | Artificial sequence | IGYGGNI |
| 6 | CDR-H3 (amino acid sequence-identified using the IMGT numbering system) | Artificial sequence | TRESFYDGYPFDY |
| 7 | CDR-L1 (amino acid sequence-identified using the Kabat numbering system) | Artificial sequence | RASQDIRNYLN |
| 8 | CDR-L2 (amino acid sequence-identified | Artificial sequence | YTSRLHS |

SEQUENCE OVERVIEW

| SEQ ID NO: Description | Organism | Sequence |
|---|---|---|
| using the Kabat numbering system) | | |
| 9 CDR-L3 (amino acid sequence-identified using the Kabat numbering system) | Artificial sequence | QQGNSLPRT |
| 10 CDR-L1 (amino acid sequence-identified using the IMGT numbering system) | Artificial sequence | QDIRNY |
| 11 CDR-L2 (amino acid sequence-identified using the IMGT numbering system) | Artificial sequence | YTS |
| 12 CDR-L3 (amino acid sequence-identified using the IMGT numbering system) | Artificial sequence | QQGNSLPRT |
| 13 VH1 (amino acid sequence) | Artificial sequence | QVQLQESGPGLVKPSQTLSLTCT VSGDSFTNDYYWNWIRQHPGKGL EWIGHIGYGGNINYNPSLKNRLS MSRDTSKNQFSLKLSSVTAADTA VYYCTRESFYDGYPFDYWGQGTL VTVSS |
| 14 VH2 (amino acid sequence) | Artificial sequence | QVQLQESGPGLVKPSETLSLTCS VSGDSFTNDYYWNWIRQSPGKGL EWIGHIGYGGNINYNPSLKNRVS ISIDTSRNQFSLKVTSMTAADTA VYYCTRESFYDGYPFDYWGQGTL VTVSS |
| 15 VH3 (amino acid sequence) | Artificial sequence | EVQLLESGPGLVKPSQTLSLTCT VSGDSFTNDYYWNWIRQHPGKGL EWIGHIGYGGNINYNPSLKNRVT ISVDTSKNQFSLKLSSVTAADTA VYYCTRESFYDGYPFDYWGQGTL VTVSS |
| 16 VH4 (amino acid sequence) | Artificial sequence | QVQLQESGPGLVKPSETLSLTCT VSGDSFTNDYYWNWIRQPPGKGL EWIAHIGYGGNINYNPSLKNRVT ISIDTSKNQFSLRLRSVTASDTA VYYCTRESFYDGYPFDYWGQGTL VTVSS |
| 17 VH5 (amino acid sequence) | Artificial sequence | QVQLQESGPGLVKPSQTLSLTCA VYGDSFTNDYYWNWIRQPPGKGL EWIGHIGYGGNINYNPSLKNRVT ISVDTSKNQFSLKLSSVTAADTA VYYCTRESFYDGYPFDYWGQGTL VTVSA |
| 18 VL1 (amino acid sequence) | Artificial sequence | DIQMTQSPSSLSASVGDRVTVTC RASQDIRNYLNWYQQPGKAPKL LIYYTSRLHSGVPSRFSGSGSGT DFTLTISSLQPEDFATYFCQQGN SLPRTFGQGTKVEIK |
| 19 VL2 (amino acid sequence) | Artificial sequence | DIQMTQSPSSLSASVGDRVTITC RASQDIRNYLNWYQQKPGKTPKL LIYYTSRLHSGVPSRFSGSGSGT DFIFTISSLQPEDIATYYCQQGN SLPRTFGGGTKVEIK |
| 20 VL3 (amino acid sequence) | Artificial sequence | DIQMTQSPSSLSASVGDRVTITC RASQDIRNYLNWYQQKPGKAPKL LLYYTSRLHSGVPSRFSGSGSGT |

-continued

| SEQ ID NO:Description | Organism | Sequence |
|---|---|---|
| | | DYTLTISSLQPEDFATYYCQQGN SLPRTFGGGTKVEIK |
| 21 VL4 (amino acid sequence) | Artificial sequence | DIQLTQSPSSLSASVGDRVTITC RASQDIRNYLNWYQQKPGKGPKL LIYYTSRLHSGVPSRFSGSGSGT DFSLTISSLQPEDLATYYCQQGN SLPRTFGGGTKVEIK |
| 22 VL5 (amino acid sequence) | Artificial sequence | DIQMTQSPSSLSASVGDRVTITC RASQDIRNYLNWYQQKPGKVPKL LIYYTSRLHSGVPSRFSGSGSGT DFTLTISSLQPEDVATYYCQQGN SLPRTFGGGTKLEIK |
| 23 Human S100A4 (protein) amino acids 1 to 101 | Homo sapiens (Accession No: NP_062427.1) | MACPLEKALDVMVSTFHKYSGKE GDKFKLNKSELKELLTRELPSFL GKRTDEAAFQKLMSNLDSNRDNE VDFQEYCVFLSCIAMMCNEFFEG FPDKQPRKK |
| 24 VH1_H40Phe (amino acid sequence) | Artificial sequence | QVQLQESGPGLVKPSQTLSLTCT VSGDSFTNDYYWNWIRQFPGKGL EWIGHIGYGGNINYNPSLKNRLS MSRDTSKNQFSLKLSSVTAADTA VYYCTRESFYDGYPFDYWGQGTL VTVSS |
| 25 VH1_H43Ser (amino acid sequence) | Artificial sequence | QVQLQESGPGLVKPSQTLSLTCT VSGDSFTNDYYWNWIRQHPGSGL EWIGHIGYGGNINYNPSLKNRLS MSRDTSKNQFSLKLSSVTAADTA VYYCTRESFYDGYPFDYWGQGTL VTVSS |
| 26 VH1_H44Lys (amino acid sequence) | Artificial sequence | QVQLQESGPGLVKPSQTLSLTCT VSGDSFTNDYYWNWIRQHPGKKL EWIGHIGYGGNINYNPSLKNRLS MSRDTSKNQFSLKLSSVTAADTA VYYCTRESFYDGYPFDYWGQGTL VTVSS |
| 27 VH2_H40Phe (amino acid sequence) | Artificial sequence | QVQLQESGPGLVKPSETLSLTCS VSGDSFTNDYYWNWIRQFPGKGL EWIGHIGYGGNINYNPSLKNRVS ISIDTSRNQFSLKVTSMTAADTA VYYCTRESFYDGYPFDYWGQGTL VTVSS |
| 28 VH2_H43Ser (amino acid sequence) | Artificial sequence | QVQLQESGPGLVKPSETLSLTCS VSGDSFTNDYYWNWIRQSPGSGL EWIGHIGYGGNINYNPSLKNRVS ISIDTSRNQFSLKVTSMTAADTA VYYCTRESFYDGYPFDYWGQGTL VTVSS |
| 29 VH2_H44Lys (amino acid sequence) | Artificial sequence | QVQLQESGPGLVKPSETLSLTCS VSGDSFTNDYYWNWIRQSPGKKL EWIGHIGYGGNINYNPSLKNRVS ISIDTSRNQFSLKVTSMTAADTA VYYCTRESFYDGYPFDYWGQGTL VTVSS |
| 30 VH3_H40Phe (amino acid sequence) | Artificial sequence | EVQLLESGPGLVKPSQTLSLTCT VSGDSFTNDYYWNWIRQFPGKGL EWIGHIGYGGNINYNPSLKNRVT ISVDTSKNQFSLKLSSVTAADTA VYYCTRESFYDGYPFDYWGQGTL VTVSS |
| 31 VH3_H43Ser (amino acid sequence) | Artificial sequence | EVQLLESGPGLVKPSQTLSLTCT VSGDSFTNDYYWNWIRQHPGSGL EWIGHIGYGGNINYNPSLKNRVT |

SEQUENCE OVERVIEW

| SEQ ID NO:Description | Organism | Sequence |
|---|---|---|
| | | ISVDTSKNQFSLKLSSVTAADTA VYYCTRESFYDGYPFDYWGQTL VTVSS |
| 32 VH3_H44Lys (amino acid sequence) | Artificial sequence | EVQLLESGPGLVKPSQTLSLTCT VSGDSFTNDYYWNWIRQHPGKKL EWIGHIGYGGNINYNPSLKNRVT ISVDTSKNQFSLKLSSVTAADTA VYYCTRESFYDGYPFDYWGQTL VTVSS |
| 33 VH4_H40Phe (amino acid sequence) | Artificial sequence | QVQLQESGPGLVKPSETLSLTCT VSGDSFTNDYYWNWIRQFPGKGL EWIAHIGYGGNINYNPSLKNRVT ISIDTSKNQFSLRLRSVTASDTA VYYCTRESFYDGYPFDYWGQTL VTVSS |
| 34 VH4_H43Ser (amino acid sequence) | Artificial sequence | QVQLQESGPGLVKPSETLSLTCT VSGDSFTNDYYWNWIRQPPGGL EWIAHIGYGGNINYNPSLKNRVT ISIDTSKNQFSLRLRSVTASDTA VYYCTRESFYDGYPFDYWGQTL VTVSS |
| 35 VH4_H44Lys (amino acid sequence) | Artificial sequence | QVQLQESGPGLVKPSETLSLTCT VSGDSFTNDYYWNWIRQPPGKKL EWIAHIGYGGNINYNPSLKNRVT ISIDTSKNQFSLRLRSVTASDTA VYYCTRESFYDGYPFDYWGQTL VTVSS |
| 36 VH5_H40Phe (amino acid sequence) | Artificial sequence | QVQLQESGPGLVKPSQTLSLTCA VYGDSFTNDYYWNWIRQFPGKGL EWIGHIGYGGNINYNPSLKNRVT ISVDTSKNQFSLKLSSVTAADTA VYYCTRESFYDGYPFDYWGQTL VTVSA |
| 37 VH5_H43Ser (amino acid sequence) | Artificial sequence | QVQLQESGPGLVKPSQTLSLTCA VYGDSFTNDYYWNWIRQPPSGL EWIGHIGYGGNINYNPSLKNRVT ISVDTSKNQFSLKLSSVTAADTA VYYCTRESFYDGYPFDYWGQTL VTVSA |
| 38 VH5_H44Lys (amino acid sequence) | Artificial sequence | QVQLQESGPGLVKPSQTLSLTCA VYGDSFTNDYYWNWIRQPPGKKL EWIGHIGYGGNINYNPSLKNRVT ISVDTSKNQFSLKLSSVTAADTA VYYCTRESFYDGYPFDYWGQTL VTVSA |
| 39 VL1_L42Gly (amino acid sequence) | Artificial sequence | DIQMTQSPSSLSASVGDRVTVTC RASQDIRNYLNWYQQQPGGGAPKL LIYYTSRLHSGVPSRFSGSGSGT DFTLTISSLQPEDFATYFCQQGN SLPRTFGQGTKVEIK |
| 40 VL1_L43Thr (amino acid sequence) | Artificial sequence | DIQMTQSPSSLSASVGDRVTVTC RASQDIRNYLNWYQQQPGKTPKL LIYYTSRLHSGVPSRFSGSGSGT DFTLTISSLQPEDFATYFCQQGN SLPRTFGQGTKVEIK |
| 41 VL1_L44Leu (amino acid sequence) | Artificial sequence | DIQMTQSPSSLSASVGDRVTVTC RASQDIRNYLNWYQQQPGKALKL LIYYTSRLHSGVPSRFSGSGSGT DFTLTISSLQPEDFATYFCQQGN SLPRTFGQGTKVEIK |
| 42 VL2_L42Gly (amino acid sequence) | Artificial sequence | DIQMTQSPSSLSASVGDRVTITC RASQDIRNYLNWYQQKPGGTPKL |

| SEQ ID NO: Description | Organism | Sequence |
|---|---|---|
| | | LIYYTSRLHSGVPSRFSGSGSGT DFIFTISSLQPEDIATYYCQQGN SLPRTFGGGTKVEIK |
| 43 VL2_L43Thr (amino acid sequence) | Artificial sequence | DIQMTQSPSSLSASVGDRVTITC RASQDIRNYLNWYQQKPGKTPKL LIYYTSRLHSGVPSRFSGSGSGT DFIFTISSLQPEDIATYYCQQGN SLPRTFGGGTKVEIK |
| 44 VL2_L44Leu (amino acid sequence) | Artificial sequence | DIQMTQSPSSLSASVGDRVTITC RASQDIRNYLNWYQQKPGKTLKL LIYYTSRLHSGVPSRFSGSGSGT DFIFTISSLQPEDIATYYCQQGN SLPRTFGGGTKVEIK |
| 45 VL3_L42Gly (amino acid sequence) | Artificial sequence | DIQMTQSPSSLSASVGDRVTITC RASQDIRNYLNWYQQKPGGAPKL LLYYTSRLHSGVPSRFSGSGSGT DYTLTISSLQPEDFATYYCQQGN SLPRTFGGGTKVEIK |
| 46 VL3_L43Thr (amino acid sequence) | Artificial sequence | DIQMTQSPSSLSASVGDRVTITC RASQDIRNYLNWYQQKPGKTPKL LLYYTSRLHSGVPSRFSGSGSGT DYTLTISSLQPEDFATYYCQQGN SLPRTFGGGTKVEIK |
| 47 VL3_L44Leu (amino acid sequence) | Artificial sequence | DIQMTQSPSSLSASVGDRVTITC RASQDIRNYLNWYQQKPGKALKL LLYYTSRLHSGVPSRFSGSGSGT DYTLTISSLQPEDFATYYCQQGN SLPRTFGGGTKVEIK |
| 48 VL4_L42Gly (amino acid sequence) | Artificial sequence | DIQLTQSPSSLSASVGDRVTITC RASQDIRNYLNWYQQKPGGGPKL LIYYTSRLHSGVPSRFSGSGSGT DFSLTISSLQPEDLATYYCQQGN SLPRTFGGGTKVEIK |
| 49 VL4_L43Thr (amino acid sequence) | Artificial sequence | DIQLTQSPSSLSASVGDRVTITC RASQDIRNYLNWYQQKPGKTPKL LIYYTSRLHSGVPSRFSGSGSGT DFSLTISSLQPEDLATYYCQQGN SLPRTFGGGTKVEIK |
| 50 VL4_L44Leu (amino acid sequence) | Artificial sequence | DIQLTQSPSSLSASVGDRVTITC RASQDIRNYLNWYQQKPGKGLKL LIYYTSRLHSGVPSRFSGSGSGT DFSLTISSLQPEDLATYYCQQGN SLPRTFGGGTKVEIK |
| 51 VL5_L42Gly (amino acid sequence) | Artificial sequence | DIQMTQSPSSLSASVGDRVTITC RASQDIRNYLNWYQQKPGGVPKL LIYYTSRLHSGVPSRFSGSGSGT DFTLTISSLQPEDVATYYCQQGN SLPRTFGGGTKLEIK |
| 52 VL5_L43Thr (amino acid sequence) | Artificial sequence | DIQMTQSPSSLSASVGDRVTITC RASQDIRNYLNWYQQKPGKTPKL LIYYTSRLHSGVPSRFSGSGSGT DFTLTISSLQPEDVATYYCQQGN SLPRTFGGGTKLEIK |
| 53 VL5_L44Leu (amino acid sequence) | Artificial sequence | DIQMTQSPSSLSASVGDRVTITC RASQDIRNYLNWYQQKPGKVLKL LIYYTSRLHSGVPSRFSGSGSGT DFTLTISSLQPEDVATYYCQQGN SLPRTFGGGTKLEIK |
| 54 VH region 6B12 monoclonal antibody (amino acid sequence) | Artificial sequence | *MKVLSLLYLLTAIPGILS*DVQLQ ESGPGLVKPSQSLSLTCSVTGDS FTNDYYWNWIRQFPGSKLEWMGH |

| SEQ ID NO: | Description | Organism | Sequence |
|---|---|---|---|
|  | Leader sequence-FR1-CDR1-FR2-CDR2-FR3-CDR3-FR4 (CDRs underlined, leader sequence in italics, numbering according to the Kabat numbering scheme) |  | IGYGGNINYNPSLKNRISITRDT SKNQFFLRLTSVTTEDTATYYCT RESFYDGYPFDYWGQGTLVTVSA |
| 55 | VL region 6B12 monoclonal antibody (amino acid sequence) Leader sequence-FR1-CDR1-FR2-CDR2-FR3-CDR3-FR4 (CDRs underlined, leader sequence in italics, numbering according to the Kabat numbering scheme) | Artificial sequence | *MMSSAQFLGLLLLCFQGTR*CDIQ MTQTTSSLSASLGDRVTISC<u>RAS QDIRNYLN</u>WYQQRPGGTLKLL<u>IY YTSRLHS</u>GVPSRFSGSGSGTDYS LTISNLEQEDIATYFC<u>QQGNSLP RT</u>FGGGTKLEIK |
| 56 | IgG4 CH | Homo sapiens | ASTKGPSVFPLAPCSRSTSEST AALGCLVKDYFPEPVTVSWNSGA LTSGVHTFPAVLQSSGLYSLSSV VTVPSSSLGTKTYTCNVDHKPSN TKVDKRVESKYGPPCPPCPAPEF LGGPSVFLFPPKPKDTLMISRTP EVTCVVVDVSQEDPEVQFNWYVD GVEVHNAKTKPREEQFNSTYRVV SVLTVLHQDWLNGKEYKCKVSNK GLPSSIEKTISKAKGQPREPQVY TLPPSQEEMTKNQVSLTCLVKGF YPSDIAVEWESNGQPENNYKTTP PVLDSDGSFFLYSRLTVDKSRWQ EGNVFSCSVMHEALHNHYTQKSL SLSLG |
| 57 | κ light chain constant region (CL) | Homo sapiens | RTVAAPSVFIFPPSDEQLKSGTA SVVCLLNNFYPREAKVQWKVDNA LQSGNSQESVTEQDSKDSTYSLS STLTLSKADYEKHKVYACEVTHQ GLSSPVTKSENRGEC |
| 58 | AX-202 complete heavy chain | Artificial sequence | QVQLQESGPGLVKPSQTLSLTCT VSGDSFTNDYYWNWIRQHPGKGL EWIGHIGYGGNINYNPSLKNRLS MSRDTSKNQFSLKLSSVTAADTA VYYCTRESFYDGYPFDYWGQGTL VTVSSASTKGPSVFPLAPCSRST SESTAALGCLVKDYFPEPVTVSW NSGALTSGVHTFPAVLQSSGLYS LSSVVTVPSSSLGTKTYTCNVDH KPSNTKVDKRVESKYGPPCPPCP APEFLGGPSVFLFPPKPKDTLMI SRTPEVTCVVVDVSQEDPEVQFN WYVDGVEVHNAKTKPREEQFNST YRVVSVLTVLHQDWLNGKEYKCK VSNKGLPSSIEKTISKAKGQPRE PQVYTLPPSQEEMTKNQVSLTCL VKGFYPSDIAVEWESNGQPENNY KTTPPVLDSDGSFFLYSRLTVDK SRWQEGNVFSCSVMHEALHNHYT QKSLSLSLG |
| 59 | AX-202 complete light chain | Artificial sequence | DIQMTQSPSSLSASVGDRVTITC RASQDIRNYLNWYQQKPGKALKL LLYYTSRLHSGVPSRFSGSGSGT DYTLTISSLQPEDFATYYCQQGN SLPRTFGGGTKVEIKRTVAAPSV FIFPPSDEQLKSGTASVVCLLNN FYPREAKVQWKVDNALQSGNSQE SVTEQDSKDSTYSLSSTLTLSKA |

-continued

| SEQUENCE OVERVIEW | | |
|---|---|---|
| SEQ ID NO: Description | Organism | Sequence |
| | | DYEKHKVYACEVTHQGLSSPVTK SFNRGEC |

REFERENCES

The disclosures of all patent and scientific literature cited herein are expressly incorporated in their entirety by reference.

Ambartsumian N, Klingelhöfer J, Grigorian M. (2019). The Multifaceted S100A4 Protein in Cancer and Inflammation. *Methods Mol Biol.,* 1929:339-365. doi: 10.1007/978-1-4939-9030-6_22.

Akiyama N, Hozumi H, Isayama T, Okada J, Sugiura K, Yasui H, Suzuki Y, Kono M, Karayama M, Furuhashi K, Enomoto N, Fujisawa T, Inui N, Nakamura Y, Suda T. (2020). Clinical significance of serum S100 calcium-binding protein A4 in idiopathic pulmonary fibrosis. *Respirology.,* 25(7):743-749. doi: 10.1111/resp.13707.

Arman M, Krauel K. Human platelet IgG Fc receptor FcγRIIA in immunity and thrombosis. J Thromb Haemost. 2015; 13:893-908.0

Boye, K., Nesland, J. M., Sandstad, B., Maelandsmo, G. M., & Flatmark, K. (2010). Nuclear S100A4 is a novel prognostic marker in colorectal cancer. *European Journal of Cancer,* 46(16), 2919-2925. doi:10.1016/.ejca.2010.07.013.

Cabezon, T., Celis, J. E., Skibsh0j, I., Klingelhof er, J., Grigorian, M., Gromov, P., Rank, F., et al. (2007). Expression of S100A4 by a variety of cell types present in the tumour microenvironment of human breast cancer. *Int. J. Cancer,* 121(1), 1433-1444. doi: 10.1002/ijc.22850.

Cerezo L A, Kuncovi K, Mann H, Tomcik M, Zámecnik J, Lukanidin E, Neidhart M, Gay S, Grigorian M, Vencovsky J, Senolt L. (2011). The metastasis promoting protein S100A4 is increased in idiopathic inflammatory myopathies. *Rheumatology (Oxford).,* 50(10):1766-72. doi: 10.1093/rheumatology/ker218.

Chow K H, Park H J, George J, Yamamoto K, Gallup A D, Graber J H, Chen Y, Jiang W, Steindler D A, Neilson E G, Kim B Y S, Yun K. (2017). S100A4 Is a Biomarker and Regulator of Glioma Stem Cells That Is Critical for Mesenchymal Transition in Glioblastoma. *Cancer Res.,* 77(19):5360-5373. doi: 10.1158/0008-5472.CAN-17-1294.

Donato, R. (2003). Intracellular and extracellular roles of S100 proteins. *Microscopy Research and Technique,* 60(6), 540-551. doi: 10.1002/jemt. 10296.

Erp E A van, Luytjes W, Ferwerda G, Kasteren P B van. Fc-Mediated Antibody Effector Functions During Respiratory Syncytial Virus Infection and Disease. Front Immunol. 2019; 10:548.

Fei F, Qu J, Li C, Wang X, Li Y, Zhang S. (2017). Role of metastasis-induced protein S100A4 in human non-tumor pathophysiologies. *Cell Biosci.,* 25; 7:64. doi: 10.1186/s13578-017-0191-1

Grum-Schwensen, B., Klingelhof er, J., Berg, C. H., E L Naaman, C, Grigorian, M., Lukanidin, E., & Ambartsumian, N. (2005). Suppression of tumour development and metastasis formation in mice lacking the S100A4 (mts1) gene. *Cancer Research,* 65(9), 3772-3780. doi:10.1158/0008-5472. CAN-04-4510.

Grum-Schwensen, B., Klingelhofer, J., Grigorian, M., Almholt, K., Nielsen, B. S., Lukanidin, E., & Ambartsumian, N. (2010). Lung metastasis fails in MMTV-PyMT oncomice lacking S100A4 due to a T-cell deficiency in primary tumours. *Cancer research,* 70(3), 936-947. doi:10.1158/0008-5472. CAN-09-3220.

Helfman, D. M., Kim, E. J., Lukanidin, E., & Grigorian, M. (2005). The metastasis associated protein S100A4: role in tumour progression and metastasis. *British journal of cancer,* 92(11), 1955-1958. doi:10.1038/sj.bjc.6602.613.

Kalluri R, Zeisberg M. Fibroblasts in cancer. (2006). *Nat Rev Cancer,* 6(5):392-401. doi: 10.1038/nrc1877.

Klingelhöfer J, Senolt L, Baslund B, Nielsen G H, Skibshoj I, Pavelka K, Neidhart M, Gay S, Ambartsumian N, Hansen B S, Petersen J, Lukanidin E, Grigorian M. (2007). Up-regulation of metastasis-promoting S100A4 (Mts-1) in rheumatoid arthritis: putative involvement in the pathogenesis of rheumatoid arthritis. *Arthritis Rheum.,* 56(3):779-89. doi: 10.1002/art.22398.

Klingelhöfer, Jörg et al. "Anti-S100A4 antibody suppresses metastasis formation by blocking stroma cell invasion." *Neoplasia* (New York, N.Y.) vol. 14, 12 (2012): 1260-8. doi:10.1593/neo.121554

Lo, J. F., Yu, C. C., Chiou, S. H., Huang, C. Y., Jan, C. I., Lin, S. C., Liu, C. J., Hu, W. Y. & Yu, Y. H. (2011). The epithelial-mesenchymal transition mediator S100A4 maintains cancer-initiating cells in head and neck cancers. *Cancer Research,* 71(5), 1912-1923.

Maelandsmo, G. M., Florenes, V. A., Nguyen, M. T. P., Flatmark, K., & Davidson, B. (2009). Different expression and clinical role of S100A4 in serous ovarian carcinoma at different anatomic sites. *Tumour biology: the journal of the International Society for Oncodevelopmental Biology and Medicine,* 30(1), 15-25. doi:10.1159/000199447.

Mishra, S. K., Siddique, H. R., & Saleem, M. (2011). S100A4 calcium-binding protein is key player in tumour progression and metastasis: preclinical and clinical evidence. *Cancer metastasis reviews,* doi:10.1007/s10555-011-9338-4.

Neidhart M, Pajak A, Laskari K, Riksen N P, Joosten L A B, Netea M G, Lutgens E, Stroes E S G, Ciurea A, Distler O, Grigorian M, Karouzakis E. (2019). Oligomeric S100A4 Is Associated With Monocyte Innate Immune Memory and Bypass of Tolerance to Subsequent Stimulation With Lipopolysaccharides. *Front Immunol.;* 10:791. doi: 10.3389/fimmu.2019.00791.

Schmidt-Hansen, B., Klingelhof er, J., Grum-Schwensen, B., Christensen, A., Andresen, S., Kruse, C., Hansen, T., et al. (2004a). Functional significance of metastasis-inducing S100A4 (Mts1) in tumour-stroma interplay. *THE JOURNAL OF BIOLOGICAL CHEMISTRY,* 275(23), 24498-24504. doi: 10.1074/jbe.M400441200.

Sherbet, G. V. (2009). Metastasis promoter S100A4 is a potentially valuable molecular target for cancer therapy. *Cancer letters,* 280(1), 15-30. doi: 10.1016/j.canlet.2008.10.037.

Sun D, Popescu N I, Raisley B, Keshari R S, Dale G L, Lupu F, et al. *Bacillus anthracis* peptidoglycan activates human platelets through FcγRII and complement. Blood. 2013; 122:571-9.

Tomcik M, Palumbo-Zerr K, Zerr P, Avouac J, Dees C, Sumova B, Distler A, Beyer C, Cerezo L A, Becvar R, Distler O, Grigorian M, Schett G, Senolt L, Distler J H. (2015). S100A4 amplifies TGF-β-induced fibroblast activation in systemic sclerosis. *Ann Rheum Dis.,* 74(9):1748-55. doi: 10.1136/annrheumdis-2013-204516.

Zibert J R, Skov L, Thyssen J P, Jacobsen G K, Grigorian M. (2010) Significance of the S100A4 protein in psoriasis. *J Invest Dermatol.,* 130(1):150-60. doi: 10.1038/jid.2009.206.

---

What is claimed:

1. An isolated antibody that specifically binds S100A4, the antibody comprising a heavy chain variable region (VH) comprising the heavy chain complementarity-determining region 1 (CDR-H1), CDR-H2, and CDR-H3 amino acid sequences of the VH amino acid sequences set forth in SEQ ID NO: 13; and a light chain variable region (VL) comprising the light chain complementarity-determining region 1

(CDR-L1), CDR-L2, and CDR-L3 amino acid sequences of the VL amino acid sequence set forth in SEQ ID NO: 47, wherein the VH comprises the amino acid sequence set forth in SEQ ID NO: 13 and/or the VL comprises the amino acid sequence set forth in SEQ ID NO: 47.

2. The antibody of claim 1, wherein the antibody comprises the CDR-H1 amino acid sequence set forth in SEQ ID NO: 1 or 4, the CDR-H2 amino acid sequence set forth in SEQ ID NO: 2 or 5, and the CDR-H3 amino acid sequence set forth in SEQ ID NO: 3 or 6.

3. The antibody of claim 1, wherein the antibody comprises the CDR-L1 amino acid sequence set forth in SEQ ID NO: 7 or 10, the CDR-L2 amino acid sequence set forth in SEQ ID NO: 8 or YTS, and the CDR-L3 amino acid sequence set forth in SEQ ID NO: 9 or 12.

4. The antibody of claim 1, wherein the antibody comprises the CDR-H1 amino acid sequence set forth in SEQ ID NO: 1 or 4, the CDR-H2 amino acid sequence set forth in SEQ ID NO: 2 or 5, the CDR-H3 amino acid sequence set forth in SEQ ID NO: 3 or 6, the CDR-L1 amino acid sequence set forth in SEQ ID NO: 7 or 10, the CDR-L2 amino acid sequence set forth in SEQ ID NO: 8 or YTS, and the CDR-L3 amino acid sequence set forth in SEQ ID NO: 9 or 12.

5. The antibody of claim 1, wherein the antibody comprises the CDR-H1, CDR-H2, CDR-H3, CDR-L1, CDR-L2, and CDR-L3 amino acid sequences set forth in SEQ ID NOs: 1, 2, 3, 7, 8, and 9, respectively.

6. The antibody of claim 1, wherein the antibody comprises the CDR-H1, CDR-H2, CDR-H3, CDR-L1, CDR-L2, and CDR-L3 amino acid sequences set forth in SEQ ID NOs: 4, 5, 6, 10, YTS, and SEQ ID NO: 12, respectively.

7. The antibody of claim 1, wherein the antibody comprises a heavy chain constant region, or an Fc region thereof.

8. The antibody of claim 7, wherein the heavy chain constant region is selected from the group consisting of a human IgG1, human IgG2, human IgG3, and human IgG4.

9. The antibody of claim 7, wherein the heavy chain constant region is a human IgG4.

10. The antibody of claim 9, wherein the amino acid sequence of the human IgG4 heavy chain constant region comprises a P at position 228, numbered according to the EU numbering system.

11. The antibody of claim 9, wherein the amino acid sequence of the human IgG4 heavy chain constant region comprises or consists of the amino acid sequence set forth in SEQ ID NO: 56 or a variant thereof with at least 95% sequence identity thereto.

12. The antibody of claim 1, wherein the antibody comprises a light chain constant region.

13. The antibody of claim 12, wherein the light chain constant region is a human kappa constant region.

14. The antibody of claim 13, wherein the amino acid sequence of the human kappa light chain constant region comprises or consists of the amino acid sequence set forth in SEQ ID NO: 57 or a variant thereof with at least 95% sequence identity thereto.

15. An isolated antibody that specifically binds S100A4, the antibody comprising a heavy chain variable region (VH) and a light chain variable region (VL), wherein the VH and VL comprise the amino acid sequences, respectively, set forth in SEQ ID NOs: 13 and 47.

16. The antibody of claim 15, wherein the antibody comprises a heavy chain constant region, or an Fc region thereof.

17. The antibody of claim 16, wherein the heavy chain constant region is selected from the group consisting of a human IgG1, human IgG2, human IgG3, and human IgG4.

18. The antibody of claim 16, wherein the heavy chain constant region is a human IgG4.

19. The antibody of claim 18, wherein the amino acid sequence of the human IgG4 heavy chain constant region comprises a P at position 228, numbered according to the EU numbering system.

20. The antibody of claim 15, wherein the antibody comprises a light chain constant region.

21. The antibody of claim 20, wherein the light chain constant region is a human kappa constant region.

22. An isolated antibody that specifically binds S100A4, the antibody comprising a heavy chain and a light chain, wherein the heavy chain and the light chain comprise the amino acid sequences, respectively, set forth in SEQ ID NOs: 58 and 59.

23. A composition comprising the antibody of claim 1 and a pharmaceutically acceptable diluent, carrier, and/or excipient.

24. A composition comprising the antibody of claim 15 and a pharmaceutically acceptable diluent, carrier, and/or excipient.

25. A composition comprising the antibody of claim 22 and a pharmaceutically acceptable diluent, carrier, and/or excipient.

* * * * *